United States Patent
Ramaswami et al.

(10) Patent No.: US 6,315,384 B1
(45) Date of Patent: Nov. 13, 2001

(54) THERMAL INKJET PRINTHEAD AND HIGH-EFFICIENCY POLYCRYSTALLINE SILICON RESISTOR SYSTEM FOR USE THEREIN

(75) Inventors: Ravi Ramaswami, Vancouver, WA (US); Victor Joseph, Fremont, CA (US); Min Cao, Mountain View, CA (US); Theodore I. Kamins, Palo Alto, CA (US); John P. Whitlock, Lebanon; Anil Prem, Corvallis, both of OR (US)

(73) Assignee: Hewlett-Packard Company, Palo Alto, CA (US)

( * ) Notice: Subject to any disclaimer, the term of this patent is extended or adjusted under 35 U.S.C. 154(b) by 4 days.

(21) Appl. No.: 09/604,306

(22) Filed: Jun. 26, 2000

Related U.S. Application Data

(63) Continuation-in-part of application No. 09/264,370, filed on Mar. 8, 1999, now Pat. No. 6,127,394.

(51) Int. Cl.[7] .................................................. B41J 2/05

(52) U.S. Cl. .................. 347/20; 347/64; 438/21

(58) Field of Search .................. 347/20, 62, 63, 347/64, 85, 87; 438/21, 330, 358, 383, 385, 404

(56) References Cited

U.S. PATENT DOCUMENTS

| | | | |
|---|---|---|---|
| 3,925,106 | 12/1975 | Ku et al. | 438/383 |
| 4,391,846 | 7/1983 | Raymond | 427/99 |
| 4,467,519 | 8/1984 | Glang et al. | 438/330 |
| 4,472,875 * | 9/1984 | Christian et al. | 438/21 |
| 4,500,895 | 2/1985 | Buck et al. | 347/87 |
| 4,513,298 | 4/1985 | Scheu | 347/64 |
| 4,535,343 | 8/1985 | Wright et al. | 347/64 |
| 4,567,493 * | 1/1986 | Ikeda et al. | 347/64 |
| 4,575,923 | 3/1986 | Arnold | 438/385 |
| 4,579,600 | 4/1986 | Shah et al. | 438/385 |
| 4,719,477 * | 1/1988 | Hess | 347/59 |
| 4,725,561 | 2/1988 | Haond et al. | 438/404 |
| 4,771,295 | 9/1988 | Baker et al. | 347/87 |
| 4,963,189 | 10/1990 | Hindagolla | 106/31.52 |
| 5,010,355 * | 4/1991 | Hawkins et al. | 347/64 |
| 5,081,473 | 1/1992 | Hawkins et al. | 347/59 |
| 5,122,812 | 6/1992 | Hess et al. | 347/59 |
| 5,169,806 * | 12/1992 | Hawkins et al. | 438/21 |
| 5,185,034 | 2/1993 | Webb et al. | 106/31.43 |
| 5,240,511 | 8/1993 | Kapoor | 148/33.2 |
| 5,278,584 | 1/1994 | Keefe et al. | 347/63 |
| 5,742,307 | 4/1998 | Watrobski et al. | 347/62 |
| 5,975,686 | 11/1999 | Hauck et al. | 347/85 |

OTHER PUBLICATIONS

*Hewlett–Packard Journal*, vol. 39, No. 4 (Aug. 1988).

Biegelsen, D.K., et al., "Laser–induced crystallization of silicon islands on amorphous substrates: Multilayer structures", *Appl. Phys. Lett.*, 38(3):150–152, (Feb. 1, 1981).

Colinge, J.P., et al., "Use of selective annealing for growing very large grain silicon on insulator films", *Appl. Phys. Lett.*, 41(4):346–347, (Aug. 15, 1982).

(List continued on next page.)

*Primary Examiner*—Anh T. N. Vo

(57) ABSTRACT

A highly-efficient thermal inkjet printhead. The printhead includes a primary layer of polycrystalline silicon (preferably doped) having at least one portion thereof which functions as an ink expulsion resistor. Positioned over and above the primary layer is a secondary layer of material having at least one section produced from a selected metal silicide compound and at least another section fabricated from undoped polycrystalline silicon. The metal silicide-containing section functions as an interconnect structure and is operatively connected to the resistor in the primary layer (which is positioned beneath the secondary layer). The undoped polycrystalline silicon section is at least partially aligned over and above the resistor. As a result, the resistor is "buried" beneath the secondary layer and the various portions thereof. This system provides improved reliability, greater dimensional simplicity, optimized electrical/thermal properties, and superior versatility.

20 Claims, 13 Drawing Sheets

OTHER PUBLICATIONS

Elliott, D. J., *Integrated Circuit Fabrication Technology*, McGraw–Hill Book Company, New York (1982)—(ISBN No. 0–07–019238–3), pp. 1–40, 43–85, 125–143, 165–229, and 245–286.

Hawkins, W.G., et al., "Growth of single–crystal silicon islands on bulk fused silica by $CO_2$ laser annealing", *Appl. Phys. Lett.*, 40(4):319–321, (Feb. 15, 1982).

Ku, S.M., "Boron–Implanted Silicon Resistors", *Solid State Electronics*, 20:803–812 (1977).

Ku, S.M., et al., "Some Annealing Properties of Low–Energy–Antimony—Implanted Silicon Resistors", *Solid State Electronics*, 22:719–922 (1979).

Kung, K. T–Y., et al., "Seed selection through ion channeling to modify crystallographic orientations of polycrystalline Si films on $SiO_2$: Implant angle dependence", *Appl. Phys. Lett.*, 46(7):683–685, (Apr. 1, 1985).

Kwizera, P., et al., "Solid phase epitaxial recrystallization of thin polysilicon films amorphized by silicon ion implantation", *Appl. Phys. Lett.*, 41(4):379–381, (Aug. 15, 1982).

Lam, H.W., et al., "Characteristics of MOSFETS Fabricated in Laser–Recrystallized Polysilicon Islands with a Retaining Wall Structure on an Insulating Substrate", *IEEE Electron Device Letters*, vol. EDL–1 No. 10, pp. 206–208, (Oct. 1980).

Song, H.J., et al., "Single–crystal Si islands on $SiO_2$ obtained via excimer–laser irradiation of a patterned Si film", *Appl. Phys. Lett.*, 68(22):3165–3167, (May 27, 1996).

* cited by examiner

THERMAL INKJET PRINTHEAD AND HIGH-EFFICIENCY POLYCRYSTALLINE SILICON RESISTOR SYSTEM FOR USE THEREIN

This application is a continuation-in-part of Ser. No. 09/264,370 filed Mar. 8, 1999, now U.S. Pat. No. 6,127,394.

BACKGROUND OF THE INVENTION

The present invention generally relates to ink delivery systems, and more particularly to a thermal inkjet printhead which is characterized by improved reliability, increased longevity, diminished production costs, greater versatility, cooler printhead operating temperatures, decreased energy consumption (e.g. diminished "turn-on-energy" ["TOE"] requirements), and greater overall printing efficiency. The claimed invention likewise allows the production of printhead systems having many different size characteristics including the fabrication of "wide-array" devices. These goals are accomplished through the use of a novel polycrystalline silicon resistor system which uses a minimal number of material layers that are specially treated during production to enable various portions of the layers to perform different functions. In this manner, a simple yet highly "differentiated" structure is produced. Likewise, the completed resistor elements are located in a "buried" configuration within the printhead as discussed in considerable detail below.

Substantial developments have been made in the field of electronic printing technology. A wide variety of highly-efficient printing systems currently exist which are capable of dispensing ink in a rapid and accurate manner. Thermal inkjet systems are especially important in this regard. Printing units using thermal inkjet technology basically involve an apparatus which includes at least one ink reservoir chamber in fluid communication with a substrate (preferably made of silicon [Si] and/or other comparable materials) having a plurality of thin-film heating resistors thereon. The substrate and resistors are maintained within a structure that is conventionally characterized as a "printhead". Selective activation of the resistors causes thermal excitation of the ink materials stored inside the reservoir chamber and expulsion thereof from the printhead. Representative thermal inkjet systems are discussed in U.S. Pat. No. 4,500,895 to Buck et al.; U.S. Pat. No. 4,771,295 to Baker et al.; U.S. Pat. No. 5,278,584 to Keefe et al.; and the *Hewlett-Packard Journal*, Vol. 39, No. 4 (August 1988), all of which are incorporated herein by reference.

The ink delivery systems described above (and comparable printing units using thermal inkjet technology) typically include an ink containment unit (e.g. a housing, vessel, or tank) having a self-contained supply of ink therein in order to form an ink cartridge. In a standard ink cartridge, the ink containment unit is directly attached to the remaining components of the cartridge to produce an integral and unitary structure wherein the ink supply is considered to be "on-board" as shown in, for example, U.S. Pat. No. 4,771,295 to Baker et al. However, in other cases, the ink containment unit will be provided at a remote location within the printer, with the ink containment unit being operatively connected to and in fluid communication with the printhead using one or more ink transfer conduits. These particular systems are conventionally known as "off-axis" printing units. Representative, non-limiting off-axis ink delivery systems are discussed in co-owned pending U.S. patent application No. 08/869,446 (filed on Jun. 5, 1997) entitled "AN INK CONTAINMENT SYSTEM INCLUDING A PLURAL-WALLED BAG FORMED OF INNER AND OUTER FILM LAYERS" (Olsen et al.) and U.S. Pat. No. 5,975,686 to Hauck et al. which are each incorporated herein by reference. The present invention is applicable to both on-board and off-axis systems (as well as any other types which include at least one ink containment vessel that is either directly or remotely in fluid communication with a printhead containing at least one ink-ejecting resistor therein as will become readily apparent from the discussion provided below.)

Regardless of the particular ink delivery system being employed, an important factor to consider involves the overall operating efficiency of the printhead with particular reference to the resistor elements that are used to expel ink on-demand during printhead operation. The term "operating efficiency" shall collectively encompass a number of different items including but not limited to internal temperature levels, thermal uniformity, ink delivery speed, expulsion frequency, energy requirements (e.g. current consumption), and the like. Typical and conventional resistor elements used for ink ejection in a thermal inkjet printhead are produced from a number of compositions including but not limited to a mixture of elemental tantalum [Ta] and elemental aluminum [Al] (also known as "TaAl"), as well as other comparable materials including tantalum nitride ("$Ta_2N$"). Polycrystalline silicon may likewise be employed in thermal inkjet printing devices, with the term "polycrystalline silicon" being generally used in a conventional manner to describe a silicon material which basically contains an aggregate of multiple individual crystals. Standard ink delivery resistor systems are discussed in considerable detail in U.S. Pat. No. 4,535,343 to Wright et al. and U.S. Pat. No. 5,122,812 to Hess et al. which are each incorporated herein by reference. Also of importance is a characteristic known as "production efficiency" which is generally defined herein to encompass the number of manufacturing steps, procedures, material layers, and the like which are needed to produce the desired resistor/printhead assembly.

However, the chemical and physical characteristics of the resistor elements and interconnection components associated therewith which are selected for use in a thermal inkjet printhead will directly influence the overall operating efficiency of the printhead (and can likewise affect the general degree of production efficiency). The terms "interconnection components", "interconnect components", "interconnection structures" and the like as employed herein generally involve the conductive traces and related elements which electrically connect the resistors to the printing control circuitry of the system (e.g. on-board or printer-based drive transistors and the like). The specific printing control circuitry which is chosen for use will depend on the type of printing apparatus under consideration. As discussed further below, the claimed invention shall not be restricted to any particular control systems and instead involves a novel arrangement of resistors and interconnect components designed to provide substantially improved operating/production efficiency.

In any thermal inkjet printing system, it is especially important that the resistor elements (and interconnect components associated therewith) be as energy efficient as possible and capable of operating at low current levels. Resistive compounds having high current requirements are typically characterized by numerous disadvantages including a need for high cost, high-current power supplies in the printer unit under consideration. Likewise, additional losses of electrical efficiency can occur which result from the passage of greater current levels through the electrical interconnect components/structures discussed above that are attached to the resistor(s), with such interconnect structures exhibiting "parasitic resistances". These parasitic resistances cause increased energy losses as greater current levels pass through the above-listed components, with such energy losses being reduced when current levels are diminished. Likewise, high current requirements in the resistor elements and the "parasitic resistances" mentioned above can result in (1) greater overall temperatures within the printhead (with particular reference to the substrate or "die" on which the printhead components are positioned [discussed further below]); and (2) lower printhead reliability/longevity levels.

Another important consideration in the development of an efficient thermal inkjet printhead is the avoidance of a condition conventionally known as "current crowding". This term shall be generally defined to involve a situation where current flow within a conductor or across an interface between two materials becomes highly non-uniform. As a result, current flow occurs within a small area of the conductor causing a very high current density (in amperes per unit area). Thus, in summary, "current crowding" is caused by a variation in some material property which results in the flow of current preferentially across a small area. For example, consider a situation where electrical current flows along a cylindrically-shaped conductor which will result in the heating of the conductor. If the conductor resistance decreases with increasing temperature, then the outside surface of the conductor will have a higher resistance compared with the center of the structure (because the outside surface can exchange heat more readily with the environment). In this manner, "current crowding" will occur since most of the current will try to flow near the low-resistance center of the structure.

"Current crowding" can reduce the overall reliability in a thermal inkjet resistor system. Depending on the degree to which "current crowding" occurs, a number of different problems can result. Severe current crowding can cause very high local current density and excessive heat generation. If the resulting heat is not effectively removed, the material being heated can melt. "Current crowding" can also lead to problems involving "electromigration". Specifically, in such a situation, "current crowding" causes high current density (but not enough to melt the structure under consideration) which nonetheless results in the physical movement of ions within the structure in the direction of electron flow. This situation can cause the structure of interest to deteriorate and otherwise experience a decrease in functionality. Further information regarding "current crowding" and the particular manner in which the present invention controls/minimizes this problem will be discussed further below in the Detailed Description of Preferred Embodiments section.

Another problem in printhead systems which contain metal structures (e.g. traces) that directly abut the resistor(s) is heat loss. Typically, metals such as aluminum have a very high thermal conductivity. As a result, a portion of the heat generated by the resistor(s) will be lost via heat conduction through abutting metal structures. To compensate for this heat loss, additional energy must be employed in the resistor assembly, thereby reducing operational efficiency.

A further important consideration in the development and production of highly-effective resistor-based thermal inkjet printheads is the ability to precisely control the thermal characteristics of the resistors in question with particular reference to (1) the resistances which can be generated per unit volume of resistor material; (2) the variation in resistance which can occur during production (with as little variation as possible being desirable); and (3) the employment of materials having favorable "TCR" levels, with the term "TCR" being conventionally defined herein to involve the "temperature coefficient of resistance". Desirable "TCR" levels in the thermal inkjet printhead/resistor systems discussed herein are optimally positive and as close to zero as possible (which is achievable using the present invention as outlined below). The "temperature coefficient of resistance" of a substance is generally defined to involve the change in resistivity of a substance per unit change in temperature. An additional item to be included in the above-described list of beneficial characteristics is the manufacture of resistor elements with low "TOE" ("turn-on-energy") requirements as mentioned above. The "TOE" associated with a given resistor in a thermal inkjet printhead is typically defined to involve the amount of energy that is required to cause the resistor of interest to generate sufficient heat for ink expulsion (which typically occurs at a representative and non-limiting temperature of about 300° C. or higher). Low "TOE" levels (which are beneficial) facilitate reduced energy consumption and more rapid operation (with particular reference to "cycling" between ink expulsion "pulses").

Finally, in designing a thermal inkjet printhead, the overall topography (namely, the structural surface geometry) of the resistor(s) and associated interconnect structures must be carefully considered. Printhead designs which incorporate a substantial number of non-planar, angular, and/or sloped components in direct proximity with the resistor elements can cause various problems. Specifically, printhead units which employ structures of this nature may be more difficult to effectively cover with the passivation coverings and other layers that are normally used to protect the resistor(s) and adjacent components from corrosion. As a result, these protective layers are more prone to various defects including but not limited to cracks, "pinholes", and the like. It is therefore desirable to employ a printhead design which avoids the use of material layers having sloped sidewalls and other geometrical complexities in the vicinity of the resistor elements.

In accordance with the information provided above, it is readily apparent that a number of important factors must be considered in the development of a thermal inkjet printhead having a maximum degree of operational efficiency. While prior printhead designs of the type discussed herein have functioned adequately, the foregoing disadvantages leave room for improvement. In this regard, a need remained (prior to development of the present invention) for a resistor system suitable for use in thermal inkjet printing systems which is capable of high efficiency/low current operation that avoids or otherwise minimizes the problems discussed above and likewise enables the beneficial characteristics described herein to be achieved. The present invention satisfies this need by providing a novel resistor system which represents a substantial improvement over previous designs. The claimed resistor system, its architecture, and the material layers/fabrication stages associated therewith offer numerous advantages including the following items: (1) improved overall reliability, stability, and longevity levels in connection with the printhead and resistor elements based on the improvements recited below; (2) the avoidance of heating efficiency problems which can lead to resistor "hot spots", absolute limits on resistance, and the like; (3) the ability to place more resistors within a given printhead in view of the reduced operating temperatures and other factors listed herein which facilitates the reduced-cost production of large-area printheads; (4) the ability to fabricate resistor structures having resistance values that are substantially independent of material thickness in connection with the deposited material layers (which is accomplished using the "buried resistor approach" outlined herein); (5) favorable "TCR"/"TOE" values; (6) the control/minimization of "current crowding" and other related problems as defined above, with this benefit leading to improved electrical efficiency; (7) reductions in printhead operating temperatures; (8) the general promotion of more favorable temperature conditions within the printhead (which result from reduced current requirements that correspondingly decrease current-based parasitic heat losses from the interconnect structures operatively attached to the resistors); (9) the ability to employ a simplified, substantially planar internal printhead design (with particular reference to the resistor element[s] and associated interconnection components) which enables more effective coverage of these items by one or more protective layers; and (10) generally superior long-term operating performance.

In accordance with the detailed information provided below, the present invention involves a thermal inkjet printhead having a novel resistor system which is unique in structure, arrangement, and functional capability. Also encompassed within the invention is an ink delivery system using the claimed printhead and specialized manufacturing methods for producing the printhead. Each of these developments will be outlined in considerable detail herein. Accordingly, the present invention represents a significant advance in thermal inkjet technology which ensures high levels of operating efficiency, excellent image quality, rapid throughput, and increased longevity/reliability.

SUMMARY OF THE INVENTION

It is an object of the present invention to provide a highly efficient thermal inkjet printhead which is characterized by improved operating efficiency.

It is another object of the invention to provide a highly efficient thermal inkjet printhead which employs an internal resistor system of novel design that offers superior thermal stability and reduced operating temperatures.

It is another object of the invention to provide a highly efficient thermal inkjet printhead which employs a novel resistor system that is characterized by improved electrical efficiency resulting from reduced current requirements.

It is another object of the invention to provide a highly efficient thermal inkjet printhead which employs a novel resistor system that effectively controls/minimizes "current crowding", electromigration, and the like.

It is another object of the invention to provide a highly efficient thermal inkjet printhead which employs a "buried resistor" design (discussed below) that enables the resistance of a given resistor element to be controlled independently of material layer thickness. This is accomplished using a specialized ion implantation procedure in a preferred embodiment. As a result, layer thickness is readily optimized in order to achieve low "interconnect" resistance (namely, resistance between the resistor[s] and their associated interconnection structures), as well as improved heat-sinking capacity.

It is another object of the invention to provide a highly efficient thermal inkjet printhead which employs a novel resistor system that promotes favorable temperature conditions within the printhead. These conditions provide higher-speed printing, better image quality, and the avoidance of "hot spots".

It is another object of the invention to provide a highly efficient thermal inkjet printhead which, in accordance with the benefits listed above, is able to employ increased numbers of heating resistors per unit area compared with standard systems.

It is another object of the invention to provide a highly efficient thermal inkjet printhead which is likewise characterized by the use of individual resistor elements having favorable resistance levels per unit volume along with optimized "TOE" ("turn-on-energy") and "TCR" ("temperature coefficient of resistance") values.

It is a further object of the invention to provide a highly efficient thermal inkjet printhead which is characterized by substantially improved reliability levels.

It is a further object of the invention to provide a highly efficient thermal inkjet printhead in which the improved reliability levels listed above are achieved by using a simplified, substantially planar surface topography relative to the resistors and interconnection structures associated therewith. The avoidance of geometrically-complex structures in the printhead enables passivation layers and other comparable components to be applied in a more effective manner which minimizes defect formation.

It is a further object of the invention to provide a highly efficient thermal inkjet printhead which employs a novel resistor system that is able to offer all of the foregoing benefits using resistor structures that can be configured in a number of different shapes, sizes, and orientations without limitation.

It is a further object of the invention to provide a highly efficient thermal inkjet printhead in which the beneficial features thereof yield a printing system that is characterized by rapid operation and the generation of stable printed images.

It is a further object of the invention to provide a highly efficient thermal inkjet printhead in which the claimed printhead structures are readily manufactured in an economical fashion on a mass-production scale.

It is a further object of the invention to provide a rapid and effective method for manufacturing a thermal inkjet printhead having the beneficial characteristics, features, and advantages outlined herein.

It is a further object of the invention to provide a rapid and effective method for manufacturing a thermal inkjet printhead having the beneficial characteristics, features, and advantages outlined herein which uses a minimal number of process steps and is effectively implemented using mass production fabrication techniques.

It is a still further object of the invention to provide a rapid and effective method for manufacturing a thermal inkjet printhead having the beneficial characteristics, features, and advantages outlined herein which uses a minimal number of material layers to generate the desired structures. Various sections of such layers are "differentiated" during production to yield components having dissimilar characteristics. In this manner, the number of material layers and overall complexity of the entire printhead can be reduced compared with "conventional" systems that do not employ the novel "internal differentiation" methods outlined herein.

It is an even further object of the invention to provide a specialized printhead of the type described above which is readily applicable to a wide variety of different ink delivery systems including (1) on-board cartridge-type units having a self-contained supply of ink associated therewith; and (2) off-axis systems as previously discussed in which the claimed printhead is operatively connected to a remotely-positioned ink containment vessel using one or more tubular conduits.

A novel and highly efficient thermal inkjet printhead is described below which provides numerous advantages over prior systems. As previously stated, the claimed printhead employs at least one resistor element (or, more simply, a "resistor") and a novel interconnection system associated therewith which are characterized by multiple benefits compared with conventional devices. These benefits are recited above and throughout the Detailed Description of Preferred Embodiments section.

As a preliminary point of information, the present invention shall not be restricted to any particular types, sizes, material-selections, or arrangements of internal printhead components unless otherwise stated herein. Likewise, the numerical parameters listed in this section and the other sections below constitute preferred embodiments designed to provide optimum results and shall not limit the invention in any respect. All recitations of chemical formulae and structures set forth herein are intended to generally indicate the types of materials which may be used in this invention. The listing of specific chemical compositions which fall within the general formulae and classifications presented below are offered for example purposes only and shall be considered non-limiting.

The claimed invention and its novel developments are applicable to all types of thermal inkjet printing systems which include (1) at least one support structure as discussed in the Detailed Description of Preferred Embodiments section; and (2) at least one ink-ejecting resistor element located inside the printhead which, when energized, will provide sufficient heat to cause ink materials in proximity therewith to be thermally expelled from the printhead. The claimed invention shall therefore not be considered printhead or support structure-specific and is not limited to any particular applications, uses, and ink compositions. Likewise, the terms "resistor element" and/or "resistor" shall be construed to cover one resistor or groups of multiple resistors regardless of shape, material-content, or dimensional characteristics.

It should also be understood that the claimed invention shall not be restricted to any particular construction techniques (including any given material deposition procedures) unless otherwise stated below. For example, the terms "forming", "applying", "delivering", "placing", "operatively attaching", "operatively connecting", "converting", "providing", and the like as used throughout this discussion shall broadly encompass any appropriate manufacturing procedures. These processes range from thin-film fabrication techniques and sputter deposition methods to pre-manufacturing the components in question (including the resistor elements and interconnection members) and then adhering such items to the chosen support structures using one or more adhesive compounds which are known in the art for this purpose. Also encompassed within the terms listed above are processes which selectively manipulate and otherwise alter the chemical structure of a single material layer in order to produce one or more discrete components therefrom. For example, as outlined in the Detailed Description of Preferred Embodiments section, it is possible to form the resistor elements and one or other structures from a single material layer by selectively treating various portions of the layer to achieve this goal. In this regard, the invention shall not be considered "production method specific" unless otherwise stated herein, with the recitation of any particular fabrication techniques being provided for example purposes only.

Likewise, it shall be understood that the terms "operative connection", "operative attachment", "in operative connection", "in operative attachment", "positioned on", "located on", "positioned above", and the like as used and claimed herein shall be broadly construed to encompass a variety of divergent attachment/connection arrangements including but not limited to (1) the direct attachment of one component to another component with no intervening materials therebetween; and (2) the attachment of one component to another component with one or more material layers therebetween provided that the one component being "attached" or "connected" to the other component is somehow "supported" or generally in electrical communication with the other component (notwithstanding the presence of one or more additional material layers therebetween). Any statement used herein which indicates that one layer of material is "above" another layer shall involve a situation wherein the particular layer that is "above" the other layer in question shall be the outermost of the two layers relative to the interior of the printhead, with the other layer being innermost. The opposite situation will be applicable regarding use of the term "below". The characterizations listed above shall be effective regardless of the orientation of the printhead.

As previously noted, a highly effective and durable printhead containing at least one resistor is provided for use in an ink delivery system. The term "ink delivery system" shall, without limitation, involve a wide variety of different devices including cartridge units of the "self-contained" type having a supply of ink stored therein. Also encompassed within this term are printing units of the "off-axis" variety which employ a printhead connected by one or more conduit members to a remotely-positioned ink containment unit in the form of a tank, vessel, housing, or other equivalent structure. Regardless of which ink delivery system is employed in connection with the claimed printhead, the present invention is capable of providing the benefits listed above which include more efficient, rapid, and reliable operation.

The following discussion shall constitute a brief and general overview of the invention. More specific details concerning particular embodiments, best modes, and other important features of the invention will again be recited in the Detailed Description of Preferred Embodiments section set forth below. All scientific terms used throughout this discussion shall be construed in accordance with the traditional meanings attributed thereto by individuals skilled in the art to which this invention pertains unless a special definition is provided herein.

The claimed invention involves a novel resistor-containing inkjet printhead which is characterized by improved functional abilities, namely, more efficient operation with improved reliability, the promotion of favorable temperature conditions within the printhead, the ability to generate clear and defined printed images in a rapid manner with greater overall longevity, reduced peak operating temperatures as noted above, decreased energy requirements, the ability to use greater numbers of resistors per unit area, favorable resistance/"TOE"/"TCR" levels which are controllable independently of material layer thickness, and the like. The components and novel features of this system will now be discussed.

In order to produce the claimed printhead, a support structure is initially provided on which the resistor elements and novel interconnect components of the invention reside. The terms "interconnect components" and "interconnect structures" shall be deemed equivalent and are defined above. The support structure typically comprises a substrate which is optimally manufactured from elemental silicon [Si], although the present invention shall not be exclusively restricted to this material with a number of other alternatives being outlined below. The support structure may have at least one or more layers of additional material thereon including but not limited to an electrically-insulating base layer produced from, for example, silicon dioxide [$SiO_2$]. The term "support structure" as used herein shall therefore encompass (1) the substrate by itself if no other material layers are positioned thereon; and (2) the substrate and any other material layers positioned on the substrate which form a composite structure on which the resistors reside or are otherwise positioned. In this regard, the phrase "support structure" shall generally involve the layer or layers of material (whatever they may be) on which the resistor elements and interconnection components are placed/formed.

Also provided as part of the printhead in a preferred and non-limiting embodiment is at least one layer of material which specifically comprises at least one opening or "orifice" therethrough. This orifice-containing layer of material may be characterized as an "orifice plate", "orifice structure", "top layer", and the like. Furthermore, single or multiple layers of materials may be employed for this purpose without restriction, with the terms "orifice plate", "orifice structure", etc. being defined to encompass both single and multiple layer embodiments. The resistor element (s) of the present invention are positioned between the orifice-containing layer of material and the support structure as discussed below and shown in the accompanying drawing figures. Again, more specific information regarding these components, what they are made from, how they are arranged, and the manner in which they are assembled/fabricated will be outlined below in the Detailed Description of Preferred Embodiments section.

With continued reference to the printhead components mentioned above, at least one resistor is positioned within the printhead (optimally between the support structure and the orifice-containing layer) for expelling ink on-demand from the printhead. The resistor is in fluid communication with a supply of ink as shown in the accompanying drawing figures so that effective printing can occur. Likewise, the resistor is specifically placed on the support structure in a preferred embodiment, with the terms "placed", "positioned", "located", "oriented", "operatively attached", "operatively connected", "formed", and the like relative to placement of the resistor on the support structure encompassing a situation in which (1) the resistor is secured directly on and to the upper surface of the substrate under consideration without any intervening material layers therebetween; or (2) the resistor is "supported" by the substrate in which one or more intermediate material layers (including any insulating base layer[s]) are nonetheless located between the substrate and resistor. Both of these alternatives shall be considered equivalent and encompassed within the present claims.

At this point, the novel resistor system of the present invention (and the "buried" design associated therewith) will be generally summarized. In accordance with a preferred embodiment of the invention, each resistor is formed as part of a primary layer of material preferably comprised of doped polycrystalline silicon (although undoped polycrystalline silicon can also be employed as discussed below). Specifically, the primary layer comprises at least one portion thereof which functions as a resistor element that is used to expel ink on-demand from the printhead using thermal inkjet technology. The term "polycrystalline silicon" shall be construed in accordance with the conventional definition thereof and basically involves a silicon material containing an aggregate of multiple crystals. Doping of the polycrystalline silicon is likewise undertaken in a standard manner as discussed below, with the term "doping" involving a situation in which selected "impurities" (e.g. ions) are added to a material in order to alter its chemical, physical, and/or electrical characteristics. In a preferred embodiment designed to provide optimum results, representative and non-limiting doped polycrystalline silicon compositions which are suitable for use in the primary layer include but are not limited to phosphorous-doped polycrystalline silicon (preferred), boron-doped polycrystalline silicon, arsenic-doped polycrystalline silicon, antimony-doped polycrystalline silicon, and mixtures thereof. The manner in which doping is accomplished will again be outlined below in the Detailed Description of Preferred Embodiments section.

Next, the claimed resistor system employs a secondary layer of material which is positioned above the primary layer discussed above. In a preferred embodiment, the secondary layer is directly applied to the top of the primary layer so that the secondary layer is operatively attached to the primary layer, with the term "operatively attached" being previously defined. At least one section or portion of the secondary layer is comprised of a selected metal silicide compound which is operatively connected to and in electrical communication with the resistor element. This section of the secondary layer functions as an interconnect structure which links the resistor to a signal source. In a preferred embodiment, dual metal silicide-containing sections are provided as part of the secondary layer which are spaced apart from each other. These structures are again in operative/electrical communication with the resistor and on opposite sides thereof.

A number of different metal silicide compounds may be used in connection with the above-listed section(s) of the secondary layer, with the following non-limiting, representative examples being applicable: titanium silicide ($TiS_2$) which is preferred, cobalt silicide ($CoSi_2$), tungsten silicide ($WSi_2$), platinum silicide (PtSi), palladium silicide ($Pd_2Si$), molybdenum silicide ($MoSi_2$), tantalum silicide ($TaSi_2$), and mixtures thereof.

At this point and in accordance with the further information outlined below, the claimed printhead will contain (1) the primary layer of material produced from polycrystalline silicon (preferably doped) in which at least one portion thereof will function as a resistor element in the printhead; and (2) the secondary layer of material recited above which comprises at least one portion of metal silicide which is operatively and electrically connected to the resistor. Also included as part of the secondary layer is an intermediate section made of polycrystalline silicon (preferably undoped). The polycrystalline silicon-containing intermediate section is at least partially aligned over and above the resistor element. There may also be one or more additional material layers located between the primary and secondary layers discussed herein. These additional layers (which perform a number of important protective functions and are present as a consequence of the preferred fabrication process outlined below) include (A) a layer of silicon oxide material optimally derived from the decomposition/conversion of tetraethyl orthosilicate (also characterized herein as "TEOS") positioned at least partially over and above the resistor element in the primary layer; and (B) a layer of silicon nitride positioned at least partially over and above the layer of silicon oxide material. The term "silicon oxide material" as used herein relative to the foregoing layer shall be defined in considerable detail later in the Detailed Description of Preferred Embodiments section. Again, the current summary is designed to provide a brief overview of the invention from a structural standpoint. More detailed information and explanatory data will be presented below concerning the components listed above.

In accordance with the design features recited herein, the resulting printhead basically involves a dual layer structure in which various regions thereof are "differentiated" by one or more selectively-applied chemical or physical processes. This internal differentiation enables a product to be generated in which the completed resistor element is "buried" beneath an upper layer of material. This upper layer again involves at least one section preferably comprised of undoped polycrystalline silicon (which is located at least partially over and above the resistor) and at least one section preferably produced from a chosen metal silicide. In an optimum and representative embodiment, dual portions of metal silicide are again provided and spaced apart from each other, with the above-described section of polycrystalline silicon (preferably undoped) being positioned between the metal silicide-containing sections. It should also be noted that each of the metal silicide-containing sections of the secondary layer will optimally have a substantially planar upper face. Likewise, the particular section of the secondary layer which is comprised of polycrystalline silicon will have a substantially planar top surface. In accordance with this design, the top surface and the upper face of both structures are substantially coplanar relative to each other. The term "coplanar" as employed herein shall involve a relationship in which the upper face of each metal silicide-containing section and the top surface of the polycrystalline silicon-containing section are both in the same plane and predominantly level with each other. The word "substantially" as used in connection with "coplanar" is employed herein to account for slight allowable deviations from exact coplanarity which are always possible in view of permitted production tolerances and other related factors. Further information regarding this aspect of the claimed invention will be presented below in the Detailed Description of Preferred Embodiments section.

The coplanar structure listed above is substantially devoid of sharp edges, angles, slopes and the like in order to create a flat/planar configuration (in direct contrast to the "sloped" topography employed in prior systems). This design is especially well-suited to the placement of one or more protective passivation layers thereon which are not subject to defect formation in the same manner associated with conventional systems which incorporate "sloped" structures. Specifically, the placement of protective passivation layers on printhead structures with sharp angles, slopes, and the like creates a situation in which the layers that cover these topographical features are subject to various defects including cracks, pinholes, and the like. As a result, ineffective coverage and protection of the underlying structures (including the resistor[s]) occurs. These problems are substantially avoided in the present invention which is again characterized by a flat, non-sloped topography in the various regions of the printhead surrounding the resistor element(s), with this topography being ideally suited to passivation layer formation.

Furthermore, one or more layers of electrically conductive material designed to perform a passivation and/or electrical conductivity function are preferably positioned over and above at least part of the section(s) of the secondary layer which are made from the chosen metal silicide compound. In this manner, rapid, reliable, and effective electrical communication is ensured between the resistor elements and electrical impulse sources which are used to "fire" the resistors and eject ink from the printhead.

In accordance with the present invention, an "ink delivery system" is likewise provided in which an ink containment vessel is operatively connected to and in fluid communication with the printheads described herein, with all of the information provided above regarding the claimed printhead designs being incorporated by reference in this section. As further discussed below, the term "operatively connected" relative to a given printhead and ink containment vessel shall involve a number of different situations including but not limited to (1) cartridge units of the "self-contained" type in which the ink containment vessel is directly attached to the printhead to produce a system having an "on-board" ink supply; and (2) printing units of the "off-axis" variety which employ a printhead connected by one or more conduit members (or similar structures) to a remotely-positioned ink containment unit in the form of a tank, vessel, housing, or other equivalent structure. The novel printhead structures of the present invention shall not be limited to use with any particular ink containment vessels, the proximity of these vessels to the printheads, and the means by which the vessels and printheads are attached to each other.

Finally, the present invention shall also encompass one or more methods for producing the novel printhead structures described above. It shall be understood that the invention is not limited to any particular printhead fabrication techniques, with a number of different methods being applicable. The manufacturing steps which are generally used for this purpose involve the materials and components recited above, with the previously-described summary of these items being incorporated by reference in this discussion. As a general and non-limiting overview designed to summarize the basic features of this invention from a method standpoint, the process of primary interest involves the steps of: (A) providing at least one primary layer of doped polycrystalline silicon (or undoped polycrystalline silicon although doped materials are preferred), with the primary layer including at least one section thereof which functions as an ink expulsion resistor; (B) operatively attaching at least one secondary layer of material (optimally polycrystalline silicon) in position above the primary layer; and (C) converting at least one section of the secondary layer to a metal silicide compound in order to produce a metal silicide-containing section and an unreacted polycrystalline silicon-containing section (which is ideally undoped). The metal silicide-containing section is operatively connected to and in electrical communication with the resistor in the system, with the polycrystalline silicon-containing section being at least partially aligned over and above the resistor. A number of variations to this general process are possible within the scope of the invention as claimed.

In the procedure discussed above, if doped polycrystalline silicon is employed in the primary layer (which is preferred), this material is optimally selected from the group consisting of phosphorous-doped polycrystalline silicon (preferred), boron-doped polycrystalline silicon, arsenic-doped polycrystalline silicon, antimony-doped polycrystalline silicon, and mixtures thereof without limitation. Likewise, in a representative and non-limiting embodiment, the chosen metal silicide compound is selected from the group consisting of titanium silicide (preferred), cobalt silicide, tungsten silicide, platinum silicide, molybdenum suicide, tantalum silicide, palladium silicide, and mixtures thereof.

It should also be noted that an additional step employed in a preferred version of the claimed process will involve doping at least one section of the secondary layer of polycrystalline silicon, with the doped section thereafter being converted to the chosen metal silicide compound as previously stated. This procedure ultimately produces the interconnect sections made of metal silicide illustrated in the drawing figures. The dopant composition which may be used for this purpose is optimally selected from the group consisting of phosphorous [P] (preferred), boron [B], arsenic [As], antimony [Sb], and mixtures thereof. Finally, the claimed method preferably involves operatively attaching at least one layer of electrically conductive material over and above at least part of the metal silicide-containing section(s) of the secondary layer as illustrated in the drawing figures.

To summarize the claimed method, it generally involves the steps of (1) providing at least one resistor optimally comprised of doped polycrystalline silicon which is used to expel an ink composition on-demand from the completed printhead; and (2) operatively attaching at least one layer of material in position above the resistor, with the layer of material having at least one section thereof that is produced from a metal silicide compound, with such section being operatively connected to and in electrical communication with the resistor. The above-listed layer of material further includes another section which is preferably made of undoped polycrystalline silicon. This additional section is at least partially aligned over and above the resistor. The foregoing methods are novel, unique, and offer the many advantages expressed herein.

It shall be understood that the terms "forming", "fabricating", "producing", "operatively attaching", "operatively connecting", "converting", and the like regarding the techniques which are used to assemble the claimed components in all of the embodiments of this invention shall be defined to include: (A) creating the layer or component in question directly from materials which are present or otherwise reside in the printhead on an in situ basis; (B) fabricating the layer or component under consideration using one or more material deposition processes (e.g. sputtering, plasma-enhanced chemical vapor deposition [PECVD], and the like) that are known in the art and discussed in considerable detail below; and (C) pre-manufacturing the layer or component in question and thereafter securing it in position within the printhead using chemical or physical attachment means (soldering, adhesive affixation, and the like).

In conclusion regarding the novel methods of the claimed invention, a very special procedure is provided which facilitates the production of a "buried" resistor system using a minimal number of material layers. In accordance with this process, a unique printhead is generated which includes all of the benefits listed above ranging from a substantially flat/planar topography to the control of resistance levels independently from layer thickness.

The completed printheads described herein are designed to generate a printed image from an ink supply in response to a plurality of successive electrical impulses delivered to the resistors. The novel features discussed above individually and collectively constitute a significant advance in the art of thermal inkjet technology and the generation of high-quality images with improved reliability, speed, longevity, stability, and electrical/thermal efficiency. In particular, the unique structures, components, and methods summarized above offer many important benefits compared with prior systems including but not limited to: (1) improved overall reliability, stability, and longevity levels in connection with the printhead and resistor elements based on the improvements recited herein; (2) the avoidance of heating efficiency problems which can lead to resistor "hot spots", absolute limits on resistance, and the like; (3) the ability to place more resistors within a given printhead in view of the reduced operating temperatures and other factors listed herein which facilitates the reduced-cost production of large-area printheads; (4) the ability to fabricate resistor structures having resistance values that are substantially independent of material thickness in connection with the deposited layers (which is accomplished using the "buried resistor approach" outlined above); (5) favorable "TCR"/"TOE" values; (6) the control/minimization of "current crowding" and other related problems as defined herein, with this benefit leading to improved electrical efficiency; (7) reductions in printhead operating temperatures; (8) the general promotion of more favorable temperature conditions within the printhead (which result from reduced current requirements that correspondingly decrease current-based parasitic heat losses from the interconnect structures operatively attached to the resistors); (9) the ability to employ a simplified, substantially planar internal printhead design (with particular reference to the resistor element[s] and associated interconnection components) which enables more effective coverage of these items by one or more protective layers; and (10) generally superior long-term operating performance. Of particular importance in this invention is item (4) listed above regarding layer thickness. Implementation of the claimed invention will again enable resistor values to be controlled independently of material layer thickness. This benefit will allow layer thickness in the printhead to be readily optimized in order to achieve low "interconnect resistance" (namely, resistance between the resistor[s] under consideration and their associated interconnection structures) and improved heat-sinking capacity. These and other benefits, objects, features, and advantages of the invention will become readily apparent from the following Brief Description of the Drawings and Detailed Description of Preferred Embodiments.

BRIEF DESCRIPTION OF THE DRAWINGS

The drawing figures provided below are schematic, representative, and not necessarily drawn to scale. They shall not limit the scope of the invention in any respect. Reference numbers which are carried over from one figure to another shall constitute common subject matter in the figures under consideration. Likewise, the cross-hatching shown in the drawing figures is provided for example purposes only and shall not restrict the invention to any particular construction materials. In addition, the illustration of any given number of elements, components, layers, and other structural features shall be considered representative only and shall not limit the invention in any respect unless otherwise expressly stated herein.

DETAILED DESCRIPTION OF PREFERRED EMBODIMENTS

Figure 1:
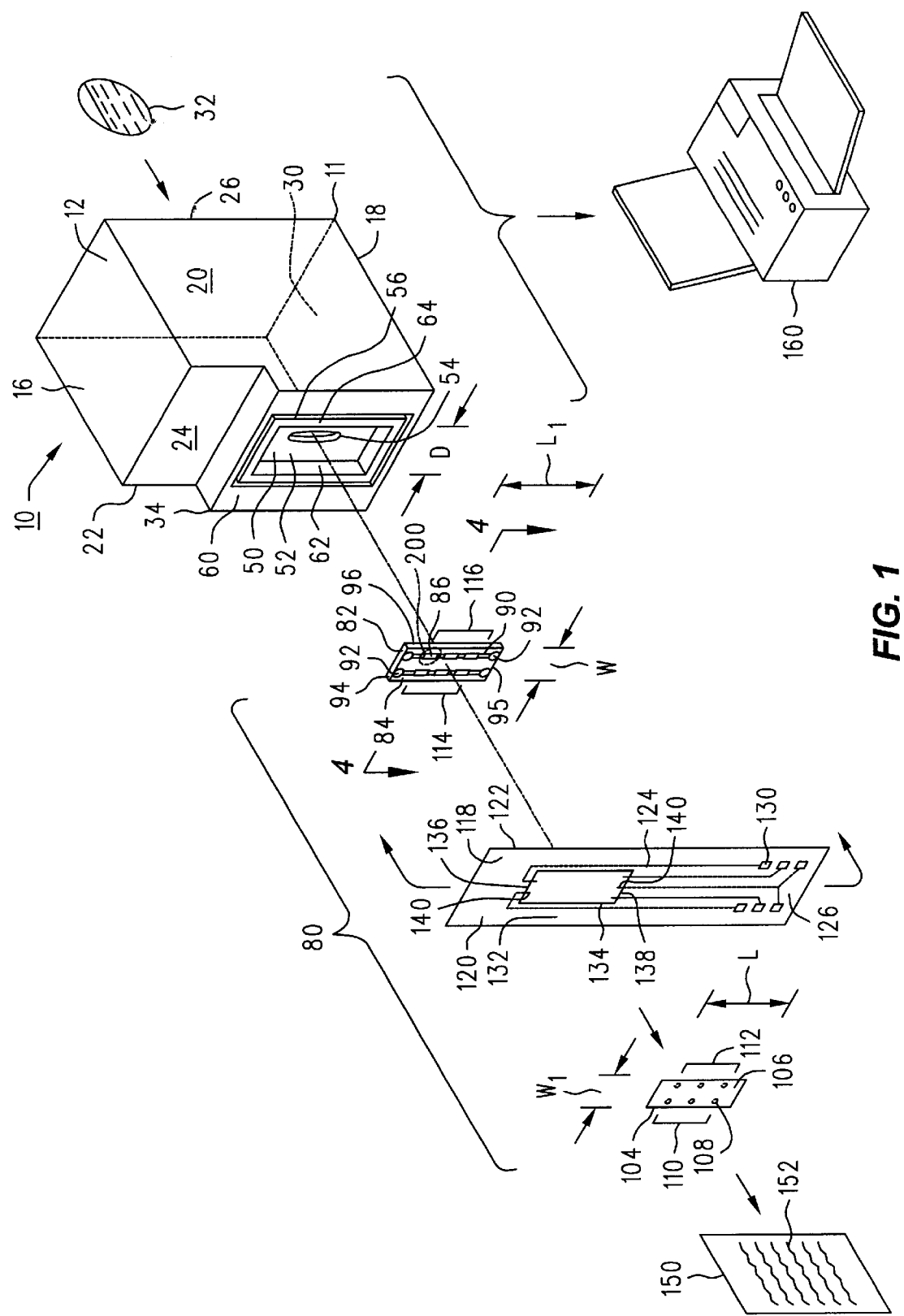
FIG. 1 is a schematically-illustrated, exploded perspective view of a representative ink delivery system in the form of an ink cartridge which is suitable for use with the components and methods of the present invention. The ink cartridge of FIG. 1 has an ink containment vessel directly attached to the printhead of the claimed invention so that an "on-board" ink supply is provided.

In accordance with the present invention, a high-efficiency thermal inkjet printhead for an ink delivery system is disclosed having improved energy efficiency, optimized thermal qualities, highly-controllable internal resistance values, and substantially increased reliability. The novel printhead is characterized by many important features including reduced internal temperatures, minimized current requirements which enable lower-cost power supplies to be employed, decreased energy losses in the system, a high degree of versatility, reduced production costs, the attainment of ideal "TOE" and "TCR" levels in a rapid and effective manner, and improved reliability over prolonged time periods. All of these benefits are directly attributable to the specialized arrangement of components in the claimed printhead structure with particular reference to the distinctive manner in which the resistor elements are oriented, fabricated, and otherwise configured. Specifically, using the dual layer "buried" design discussed herein, the resistor elements can be produced in a novel fashion, with the completed resistors being characterized by high resistance capabilities, substantially planar topographical features (which contribute to improved reliability), and the other benefits listed above. In addition, the manufacturing techniques and basic resistor designs outlined herein again enable a reduction in overall production costs since (1) only a minimal number of material layers are involved; and (2) the claimed production methods allow the resistor elements and other microelectronic structures associated with the printhead (including MOSFET ["metal oxide semiconductor field effect transistor"] gates) to be fabricated at substantially the same time. Incidentally, the recitation of any specific benefits herein shall not be construed to exclude any other benefits either recognized or unrecognized now or in the future.

Accordingly, the resistor system described herein (with the term "resistor system" involving the selected resistor[s] and associated interconnect structure[s]) offers numerous advantages over conventional designs. The term "thermal inkjet printhead" as used in this discussion shall be broadly construed to encompass, without restriction, any type of printhead having at least one heating resistor therein which is designed to thermally excite ink materials for delivery to a print media material (paper, metal, plastic, and the like). In this regard, the invention shall not be limited to any particular thermal inkjet printhead designs and resistor shapes/configurations with many different structures and internal component arrangements being possible provided that they include the resistor structures described herein which expel ink on-demand using thermal processes.

Likewise, as previously noted, the claimed printhead is prospectively applicable to many different ink delivery systems including (1) on-board cartridge-type units having a self-contained supply of ink therein which is operatively connected to and in fluid communication with the printhead; and (2) "off-axis" units which employ a remotely-positioned ink containment vessel that is operatively connected to and in fluid communication with the printhead using one or more fluid transfer conduits. The printhead of the present invention shall therefore not be considered "system specific" relative to the ink storage devices associated therewith. To provide a clear and complete understanding of the invention, the following detailed description will be divided into four sections, namely, (1) "A. A General Overview of Thermal Inkjet Technology"; (2) "B. A General Review of the Resistor Elements and Associated Structures within a Conventional Printhead"; (3) "C. The Novel Resistor Systems of the Present Invention and Representative Fabrication Methods Associated Therewith"; and (4) "D. Ink Delivery Systems using the Printheads of the Present Invention".

A. A General Overview of Thermal Inkjet Technology

The present invention is again applicable to a wide variety of ink delivery systems which include (1) a printhead; (2) at least one heating resistor associated with the printhead; and (3) an ink containment vessel having a supply of ink therein that is operatively connected to and in fluid communication with the printhead. The ink containment vessel may be directly attached to the printhead or remotely connected thereto in an "off-axis" system as previously discussed using one or more ink transfer conduits. The phrase "operatively connected" as it applies to the printhead and ink containment vessel shall encompass both of these variants and equivalent structures.

To facilitate a complete understanding of the claimed invention, an overview of thermal inkjet technology will now be provided. A representative ink delivery system in the form of a thermal inkjet cartridge unit is illustrated in FIG. 1 at reference number 10. It shall be understood that cartridge 10 is presented herein for example purposes only and is non-limiting. Cartridge 10 is shown in schematic format in FIG. 1, with more detailed information regarding cartridge 10 and its various features (as well as similar systems) being provided in U.S. Pat. No. 4,500,895 to Buck et al.; U.S. Pat. No. 4,771,295 to Baker et al.; U.S. Pat. No. 5,278,584 to Keefe et al.; and the *Hewlett-Packard Journal*, Vol. 39, No. 4 (August 1988), all of which are incorporated herein by reference.

With continued reference to FIG. 1, the cartridge 10 first includes an ink containment vessel 11 in the form of a housing 12. As noted above, the housing 12 shall constitute the ink storage unit of the invention, with the terms "ink containment unit", "ink storage unit", "housing", "vessel", and "tank" all being considered equivalent from a functional and structural standpoint. The housing 12 further comprises a top wall 16, a bottom wall 18, a first side panel 20, and a second side panel 22. In the embodiment of FIG. 1, the top wall 16 and the bottom wall 18 are substantially parallel to each other. Likewise, the first side panel 20 and the second side panel 22 are also substantially parallel to each other.

The housing 12 additionally includes a front wall 24 and a rear wall 26 which is optimally parallel to the front wall 24 as illustrated. Surrounded by the front wall 24, rear wall 26, top wall 16, bottom wall 18, first side panel 20, and second side panel 22 is an interior chamber or compartment 30 within the housing 12 (shown in phantom lines in FIG. 1) which is designed to retain a supply of an ink composition 32 therein that is either in unconstrained (e.g. "free-flowing") form or retained within a multicellular foam-type structure. Many different materials may be employed in connection with the ink composition 32 without limitation. The claimed invention is therefore not "ink-specific". The ink composition 32 will first contain at least one coloring agent. Again, this invention shall not be restricted to any particular coloring agents or mixtures thereof. While many different materials may be encompassed within the term "coloring agent", this discussion will focus on both colored and black dye products. Exemplary black dyes that are suitable for use in the ink compositions of interest are listed in U.S. Pat. No. 4,963,189 to Hindagolla which is incorporated herein by reference. Representative colored dye materials are described in the Color Index, Vol. 4, 3rd ed., published by The Society of Dyers and Colourists, Yorkshire, England (1971) which is also incorporated herein by reference and is a standard text that is well known in the art. Exemplary chemical dyes listed in the Color Index, supra, that are suitable for use herein include but are not limited to the following compositions: C.I. Direct Yellow 11, C.I. Direct Yellow 86, C.I. Direct Yellow 132, C.I. Direct Yellow 142, C.I. Direct Red 9, C.I. Direct Red 24, C.I. Direct Red 227, C.I. Direct Red 239, C.I. Direct Blue 9, C.I. Direct Blue 86, C.I. Direct Blue 189, C.I. Direct Blue 199, C.I. Direct Black 19, C.I. Direct Black 22, C.I. Direct Black 51, C.I. Direct Black 163, C.I. Direct Black 169, C.I. Acid Yellow 3, C.I. Acid Yellow 17, C.I. Acid Yellow 23, C.I. Acid Yellow 73, C.I. Acid Red 18, C.I. Acid Red 33, C.I. Acid Red 52, C.I. Acid Red 289, C.I. Acid Blue 9, C.I. Acid Blue 61:1, C.I. Acid Blue 72, C.I. Acid Black 1, C.I. Acid Black 2, C.I. Acid Black 194, C.I. Reactive Yellow 58, C.I. Reactive Yellow 162, C.I. Reactive Yellow 163, C.I. Reactive Red 21, C.I. Reactive Red 159, C.I. Reactive Red 180, C.I. Reactive Blue 79, C.I. Reactive Blue 216, C.I. Reactive Blue 227, C.I. Reactive Black 5, C.I. Reactive Black 31, C.I. Basic Yellow 13, C.I. Basic Yellow 60, C.I. Basic Yellow 82, C.I. Basic Blue 124, C.I. Basic Blue 140, C.I. Basic Blue 154, C.I. Basic Red 14, C.I. Basic Red 46, C.I. Basic Red 51, C.I. Basic Black 11, and mixtures thereof. These materials are commercially available from many sources including but not limited to the Sandoz Corporation of East Hanover, N.J. (USA), Ciba-Geigy of Ardsley, N.Y. (USA), and others.

The term "coloring agent" shall also encompass pigment dispersions known in the art which basically involve a water-insoluble colorant (namely, a pigment) which is rendered soluble through association with a dispersant (e.g. an acrylic compound). Specific pigments which may be employed to produce pigment dispersions are known in the art, and the present invention shall not be limited to any particular chemical compositions in this regard. Examples of such pigments involve the following compounds which are listed in the Color Index, supra: C.I. Pigment Black 7, C.I. Pigment Blue 15, and C.I. Pigment Red 2. Dispersant materials suitable for combination with these and other pigments include monomers and polymers which are also known in the art. An exemplary commercial dispersant consists of a product sold by W. R. Grace and Co. of Lexington, Mass. (USA) under the trademark DAXAD.

In a preferred and non-limiting embodiment, the ink compositions of interest will contain about 2–7% by weight total coloring agent therein (whether a single coloring agent or combined coloring agents are used). However, the amount of coloring agent to be employed may be varied as needed, depending on the ultimate purpose for which the ink composition is intended and the other ingredients in the ink.

The ink compositions suitable for use in this invention will also include an ink "vehicle" which essentially functions as a carrier medium and main solvent for the other ink components. Many different materials may be used as the ink vehicle, with the present invention not being limited to any particular products for this purpose. A preferred ink vehicle will consist of water combined with other ingredients (e.g. organic solvents and the like). These organic solvents include but are not limited to 2-pyrrolidone, 1,5-pentanediol, N-methyl pyrrolidone, 2-propanol, ethoxylated glycerol, 2-ethyl-2-hydroxymethyl-1,3-propanediol, cyclohexanol, and others known in the art for solvent and/or humectant purposes. All of these compounds may be used in various combinations as determined by preliminary pilot studies on the ink compositions of concern. However, in a preferred embodiment, the ink formulations will contain about 70–80% by weight total combined ink vehicle, wherein at least about 30% by weight of the total ink vehicle will typically consist of water (with the balance comprising any one of the above-listed organic solvents alone or combined). An exemplary ink vehicle will contain about 60–80% by weight water and about 10–30% by weight of one or more organic solvents.

The ink compositions may also include a number of optional ingredients in varying amounts. For example, an optional biocide may be added to prevent any microbial growth in the final ink product. Exemplary biocides suitable for this purpose include proprietary products sold under the trademarks PROXEL GXL by Imperial Chemical Industries of Manchester, England; UCARCID by Union Carbide of Danbury, Conn. (USA); and NUOSEPT by Huls America, Inc. of Piscataway, N.J. (USA). In a preferred embodiment, if a biocide is used, the final ink composition will typically include about 0.05–0.5% by weight biocide, with about 0.30% by weight being preferred.

Another optional ingredient to be employed in the ink compositions will involve one or more buffering agents. The use of a selected buffering agent or multiple (combined) buffering agents is designed to stabilize the pH of the ink formulations if needed and desired. In a preferred embodiment, the optimum pH of the ink compositions will range from about 4–9. Exemplary buffering agents suitable for this purpose include sodium borate, boric acid, and phosphate buffering materials known in the art for pH control. The selection of any particular buffering agents and the amount of buffering agents to be used (as well as the decision to use buffering agents in general) will be determined in accordance with preliminary pilot studies on the particular ink compositions of concern. Additional ingredients (e.g. surfactants) may also be present in the ink compositions if necessary. Again, many other ink materials may be employed as the ink composition 32 including those recited in U.S. Pat. No. 5,185,034 which is also incorporated herein by reference.

Referring back to FIG. 1, the front wall 24 also includes an externally-positioned, outwardly-extending printhead support structure 34 which comprises a substantially rectangular central cavity 50. The central cavity 50 includes a bottom wall 52 shown in FIG. 1 with an ink outlet port 54 therein. The ink outlet port 54 passes entirely through the housing 12 and, as a result, communicates with the compartment 30 inside the housing 12 so that ink materials can flow outwardly from the compartment 30 through the ink outlet port 54. Also positioned within the central cavity 50 is a rectangular, upwardly-extending mounting frame 56, the function of which will be discussed below. As schematically shown in FIG. 1, the mounting frame 56 is substantially even (flush) with the front face 60 of the printhead support structure 34. The mounting frame 56 specifically includes dual, elongate side walls 62, 64.

With continued reference to FIG. 1, fixedly secured to the housing 12 of the ink cartridge 10 (e.g. attached to the outwardly-extending printhead support structure 34) is a printhead generally designated in FIG. 1 at reference number 80. While the novel features of the printhead 80 will be specifically discussed in the next section, a brief overview of the printhead 80 will now be provided for background information purposes. In accordance with conventional terminology, the printhead 80 actually comprises two main components fixedly secured together (with certain sub-components positioned therebetween which are also of considerable importance). The first main component used to produce the printhead 80 consists of a substrate 82 (which functions as a "support structure" for the resistor elements as discussed further below). The substrate 82 is preferably manufactured from a number of materials without limitation including silicon [Si], silicon nitride [$Si_3N_4$] having a layer of silicon carbide [SiC] thereon, alumina [$Al_2O_3$], various metals (e.g. elemental aluminum [Al]), and the like. Secured to the upper surface 84 of the substrate 82 in the conventional printhead 80 of FIG. 1 using standard thin film fabrication techniques is at least one and preferably a plurality of individually-energizable thin-film resistors 86 (also designated herein as "resistor elements") which function as "ink ejectors". Alternatively, the resistors 86 may be affixed to at least one insulating layer which is pre-formed on the substrate 82 as discussed in the next section (Section "B") and illustrated in FIG. 4. However, for the sake of clarity and convenience in this section of the current discussion, the resistors 86 will be shown directly on the substrate 82 in FIG. 1.

In accordance with conventional thermal inkjet technology, the resistors 86 may be fabricated from a number of different materials including but not limited to undoped or doped polycrystalline silicon [Si], tantalum nitride [$Ta_2N$], nichrome [NiCr], hafnium bromide [$HfBr_4$], elemental niobium [Nb], elemental vanadium [V], elemental hafnium [Hf], elemental titanium [Ti], elemental zirconium [Zr], elemental yttrium [Y], mixtures thereof, or other comparable materials. However, as will become readily apparent from the information provided below, the present invention is primarily concerned with the use of doped polycrystalline silicon to fabricate the resistors 86 in view of its highly resistive character, cost-effectiveness, and other related factors.

Only a small number of resistors 86 are shown in the schematic representation of FIG. 1, with the resistors 86 being presented in enlarged format for the sake of clarity. A number of important material layers may likewise be present above and below the resistors 86 which shall be fully described in Section "B". Also provided on the upper surface 84 of the substrate 82 using standard photolithographic thin-film techniques is a plurality of metallic conductive traces 90 typically produced from copper [Cu], aluminum [Al], gold [Au], mixtures/alloys thereof, or other comparable materials. The conductive traces 90 (which are likewise schematically illustrated in enlarged format in FIG. 1) are also designated herein as "bus members", "elongate conductive circuit elements", "interconnect structures", "interconnect components", or simply "circuit elements" which electrically communicate with the resistors 86. In the conventional embodiment of FIG. 1, the circuit elements 90 likewise communicate with multiple metallic pad-like contact regions 92 positioned at the ends 94, 95 of the substrate 82 on the upper surface 84 which may be made from the same materials as the circuit elements 90 identified above. Alternatively, as discussed in U.S. Pat. No. 5,122,812 to Hess et al. the pad-like contact regions may be operatively connected to drive elements (e.g. transistors of the MOSFET ["metal oxide semiconductor field effect transistor"] variety or other types) which are directly located on the substrate 82. In this regard, the present invention shall not be restricted to any particular components or drive/control systems which may be attached to the interconnect structures (e.g. circuit elements 90) at the ends thereof opposite the resistors 86. The function of all these components which, in combination, are collectively designated herein as a "resistor assembly" 96 will be summarized further below. However, it should be noted that only a small number of circuit elements 90 are illustrated in the schematic representation of FIG. 1 which are again presented in enlarged format for the sake of clarity. Likewise, while the resistors 86 are shown schematically in a simplified "square" configuration in all of the accompanying drawing figures, it shall be understood that they may be formed in many different shapes, sizes, and designs ranging from those presented in FIG. 1 to "split", elongate, and/or "snake-like" structures. This configurational diversity shall likewise be applicable to the resistors of the present invention which, as previously noted, will be discussed extensively in Section "C".

Many different materials and design configurations can be used to construct the resistor assembly 96, with the present invention not being restricted to any particular elements, materials, and structures for this purpose unless otherwise indicated herein (e.g. see Section "C"). However, in a preferred, representative, and non-limiting embodiment, the resistor assembly 96 will be approximately 0.5 inches long, and will likewise contain about 300 resistors 86 thus enabling a resolution of about 600 dots per inch ("DPI"). These values may be varied in a non-limiting fashion, with the novel resistor systems of the present invention described herein enabling the production of a printhead having about 600–1200 resistors or more therein, with a print resolution of about 1200 dpi (e.g. a "true" 1200 dpi or at least two or more rows of 600 dpi resistors set at a 1200 dpi pitch in a representative embodiment).

The substrate 82 containing the resistors 86 thereon will preferably have a width "W" (FIG. 1) which is less than the distance "D" between the side walls 62, 64 of the mounting frame 56. As a result, ink flow passageways are formed on both sides of the substrate 82 so that ink flowing from the ink outlet port 54 in the central cavity 50 can ultimately come in contact with the resistors 86. It should also be noted that the substrate 82 may again include a number of other components thereon (not shown) depending on the type of ink cartridge 10 under consideration. For example, the substrate 82 may likewise comprise a plurality of logic transistors for precisely controlling operation of the resistors 86, as well as a "demultiplexer" of conventional configuration as discussed in U.S. Pat. No. 5,278,584. The demultiplexer is used to demultiplex incoming multiplexed signals and thereafter distribute these signals to the various resistors 86. The use of a demultiplexer for this purpose enables a reduction in the complexity and quantity of the circuitry (e.g. contact regions 92 and circuit elements 90) formed on the substrate 82.

Securely affixed to the substrate 82 (with the resistors 86 and a number of intervening material layers therebetween including an ink barrier layer as outlined in the next section) is the second main component of the printhead 80. Specifically, an orifice plate 104 is provided as shown in FIG. 1 which is used to distribute the selected ink compositions to a designated print media material (e.g. paper). In general, the orifice plate 104 consists of a panel member 106 (illustrated schematically in FIG. 1) which is manufactured from one or more metal compositions (e.g. gold-plated nickel [Ni] and the like). In a typical and non-limiting representative embodiment, the orifice plate 104 will have a length "L" of about 5–30 mm and a width "$W_1$" of about 3–15 mm. However, the claimed invention shall not be restricted to any particular orifice plate parameters unless otherwise indicated herein.

The orifice plate 104 further comprises at least one and preferably a plurality of openings (namely, "orifices") therethrough which are designated at reference number 108. These orifices 108 are shown in enlarged format in FIG. 1. Each orifice 108 in a representative and non-limiting embodiment will have a diameter of about 0.01–0.05 mm. In the completed printhead 80, all of the components listed above are assembled so that each orifice 108 is partially or (preferably) completely in axial alignment (e.g. in substantial "registry") with at least one of the resistors 86 on the substrate 82 and vice versa. As a result, energization of a given resistor 86 will cause ink expulsion through the desired orifice 108. The claimed invention shall not be limited to any particular size, shape, or dimensional characteristics in connection with the orifice plate 104 and shall likewise not be restricted to any number or arrangement of orifices 108. In the representative embodiment presented in FIG. 1, the orifices 108 are arranged in two rows 110, 112 on the panel member 106 associated with the orifice plate 104. If this arrangement of orifices 108 is employed, the resistors 86 on the resistor assembly 96 (e.g. the substrate 82) will also be arranged in two corresponding rows 114, 116 so that the rows 114, 116 of resistors 86 are in substantial registry with the rows 110, 112 of orifices 108. Further general information concerning this type of metallic orifice plate system is provided in, for example, U.S. Pat. No. 4,500,895 to Buck et al. which is incorporated herein by reference.

It should also be noted for background purposes that, in addition to the systems discussed above which involve metal orifice plates, alternative printing units have effectively employed orifice plate structures constructed from non-metallic organic polymer compositions. These structures typically have an exemplary and non-limiting thickness of about 1.0–2.0 mils. In this context, the term "non-metallic" will encompass a product which does not contain any elemental metals, metal alloys, or metal amalgams/mixtures. The phrase "organic polymer" wherever it is used in the Detailed Description of Preferred Embodiments section shall involve a carbon-containing structure of repeating chemical subunits. A number of different polymeric compositions may be employed for orifice plate fabrication. For example, non-metallic orifice plate members can be manufactured from the following compositions: polytetrafluoroethylene (e.g. Teflon®), polyimide, polymethylmethacrylate, polycarbonate, polyester, polyamide, polyethylene terephthalate, or mixtures thereof. Likewise, a representative commercial organic polymer (e.g. polyimide-based) composition which is suitable for constructing a non-metallic organic polymer-based orifice plate member in a thermal inkjet printing system is a product sold under the trademark "KAPTON" by E.I. du Pont de Nemours & Company of Wilmington, Del. (USA). Further data regarding the use of non-metallic organic polymer orifice plate systems is provided in U.S. Pat. No. 5,278,584 (incorporated herein by reference). Likewise, other orifice-containing structures may also be employed in addition to those outlined in this section including those which use the printhead barrier layer as the orifice-containing structure. In such an embodiment, the barrier layer would constitute a layer of material having at least one opening therein that would effectively function as an orifice plate/structure.

With continued reference to FIG. 1, a film-type flexible circuit member 118 is likewise provided in connection with the cartridge 10 which is designed to "wrap around" the outwardly-extending printhead support structure 34 in the completed ink cartridge 10. Many different materials may be used to produce the circuit member 118, with non-limiting examples including polytetrafluoroethylene (e.g. Teflon®), polyimide, polymethylmethacrylate, polycarbonate, polyester, polyamide, polyethylene terephthalate, or mixtures thereof. Likewise, a representative commercial organic polymer (e.g. polyimide-based) composition which is suitable for constructing the flexible circuit member 118 is a product sold under the trademark "KAPTON" by E.I. du Pont de Nemours & Company of Wilmington, Del. (USA) as previously noted. The flexible circuit member 118 is secured to the printhead support structure 34 by adhesive affixation using conventional adhesive materials (e.g. epoxy resin compositions known in the art for this purpose). The flexible circuit member 118 enables electrical signals to be delivered and transmitted from the printer unit to the resistors 86 on the substrate 82 as discussed below. The film-type flexible circuit member 118 further includes a top surface 120 and a bottom surface 122 (FIG. 1). Formed on the bottom surface 122 of the circuit member 118 and shown in dashed lines in FIG. 1 is a plurality of metallic (e.g. gold-plated copper) circuit traces 124 which are applied to the bottom surface 122 using known metal deposition and photolithographic techniques. Many different circuit trace patterns may be employed on the bottom surface 122 of the flexible circuit member 118, with the specific pattern depending on the particular type of ink cartridge 10 and printing system under consideration. Also provided at position 126 on the top surface 120 of the circuit member 118 is a plurality of metallic (e.g. gold-plated copper) contact pads 130. The contact pads 130 communicate with the underlying circuit traces 124 on the bottom surface 122 of the circuit member 118 via openings or "vias" (not shown) through the circuit member 118. During use of the ink cartridge 10 in a printer unit, the pads 130 in the embodiment of FIG. 1 come in contact with corresponding printer electrodes in order to transmit electrical control signals or "impulses" from the printer unit to the contact pads 130 and traces 124 on the circuit member 118 for ultimate delivery to the resistor assembly 96. Electrical communication between the resistor assembly 96 and the flexible circuit member 118 will again be outlined below.

Positioned within the middle region 132 of the film-type flexible circuit member 118 is a window 134 which is sized to receive the orifice plate 104 therein. As shown schematically in FIG. 1, the window 134 includes an upper longitudinal edge 136 and a lower longitudinal edge 138. Partially positioned within the window 134 at the upper and lower longitudinal edges 136, 138 are beam-type leads 140 which, in a representative embodiment, are gold-plated copper and constitute the terminal ends (e.g. the ends opposite the contact pads 130) of the circuit traces 124 positioned on the bottom surface 122 of the flexible circuit member 118. The leads 140 are designed for electrical connection by soldering, thermocompression bonding, and the like to the contact regions 92 on the upper surface 84 of the substrate 82 associated with the resistor assembly 96. As a result, electrical communication is established from the contact pads 130 to the resistor assembly 96 via the circuit traces 124 on the flexible circuit member 118. Electrical signals or impulses from the printer unit can then travel via the elongate conductive circuit elements 90 on the substrate 82 to the resistors 86 so that on-demand heating (energization) of the resistors 86 can occur.

It is important to emphasize that the present invention shall not be restricted to the specific printhead 80 illustrated in FIG. 1 and discussed above (which is shown in abbreviated, schematic format), with many other printhead designs also being suitable for use in accordance with the invention. The printhead 80 of FIG. 1 is again provided for example purposes and shall not limit the invention in any respect. Likewise, it should also be noted that if a non-metallic organic polymer-type orifice plate system is desired, the orifice plate 104 and flexible circuit member 118 can be manufactured as a single unit as discussed in U.S. Pat. No. 5,278,584.

The last major step in producing the completed printhead 80 involves physical attachment of the orifice plate 104 in position on the underlying portions of the printhead 80 (including the ink barrier layer as discussed below) so that the orifices 108 are in partial or (preferably) complete axial alignment with the resistors 86 on the substrate 82 and vice versa. Attachment of these components may likewise be accomplished through the use of conventional adhesive materials (e.g. epoxy and/or cyanoacrylate adhesives known in the art for this purpose) as again outlined in further detail below. At this stage, construction of the ink cartridge 10 is completed. The ink composition 32 may then be delivered on-demand to a selected print media material 150 in order to generate a printed image 152 thereon. Many different compositions can be employed in connection with the print media material 150 including but not limited to paper, plastic (e.g. polyethylene terephthalate and other comparable polymeric compounds), metal, glass, and the like. Furthermore, the cartridge 10 may be deployed or otherwise positioned within a suitable printer unit 160 (FIG. 1) which delivers electrical impulses/signals to the ink cartridge 10 so that on-demand printing of the image 152 can take place. Many different printer units can be employed in connection with the ink delivery systems of the claimed invention (including cartridge 10) without restriction. However, exemplary printer units which are suitable for use with the printheads and ink delivery systems of the present invention include but are not limited to those manufactured and sold by the Hewlett-Packard Company of Palo Alto, Calif. (USA) under the following product designations: DESKJET 400C, 500C, 540C, 660C, 693C, 820C, 850C, 870C, 1200C, and 1600C.

Figure 2:
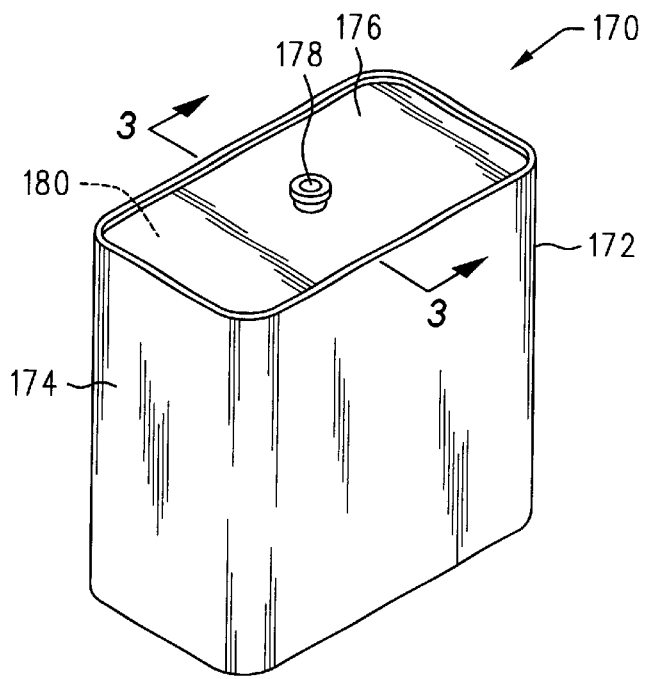
FIG. 2 is a schematically-illustrated perspective view of an ink containment vessel used in an alternative "off-axis"-type ink delivery system which may likewise be operatively connected to the printhead of the invention.
Figure 3:
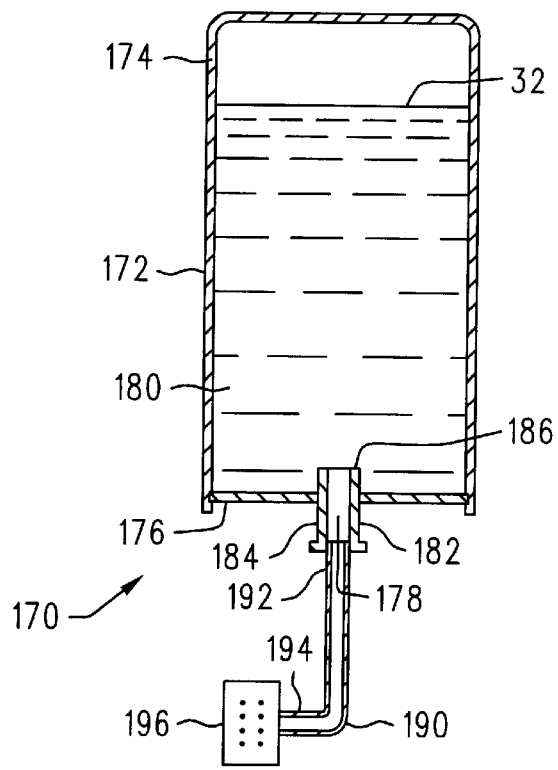
FIG. 3 is a partial cross-sectional view of the ink containment vessel shown in FIG. 2 taken along line 3—3.

The ink cartridge 10 discussed above in connection with FIG. 1 involves a "self-contained" ink delivery system which includes an "on-board" ink supply. The claimed invention may likewise be used with other systems which employ a printhead and a supply of ink stored within an ink containment vessel that is remotely spaced but operatively connected to and in fluid communication with the printhead. Fluid communication is typically accomplished using one or more tubular conduits. An example of such a system (which is known as an "off-axis" apparatus) is again disclosed in co-owned pending U.S. patent application Ser. No. 08/869,446 (filed on Jun. 5, 1997) entitled "AN INK CONTAINMENT SYSTEM INCLUDING A PLURAL-WALLED BAG FORMED OF INNER AND OUTER FILM LAYERS" (Olsen et al.) and U.S. Pat. No. 5,975,686 to Hauck et al. which are both incorporated herein by reference. As illustrated in FIGS. 2–3, a representative off-axis ink delivery system is shown which includes a tank-like ink containment vessel 170 that is designed for remote operative connection (preferably on a gravity feed or other comparable basis) to a selected thermal inkjet printhead. Again, the terms "ink containment unit", "ink storage unit", "vessel", "housing", and "tank" shall be considered equivalent in this embodiment. The ink containment vessel 170 is configured in the form of an outer shell or housing 172 which includes a main body portion 174 and a panel member 176 having an inlet/outlet port 178 passing therethrough (FIGS. 2–3). While this embodiment shall not be restricted to any particular assembly methods in connection with the housing 172, the panel member 176 is optimally produced as a separate structure from the main body portion 174. The panel member 176 is thereafter secured to the main body portion 174 as illustrated in FIG. 3 using known thermal welding processes or conventional adhesives (e.g. epoxy resin or cyanoacrylate compounds). However, the panel member 176 shall, in a preferred embodiment, be considered part of the overall ink containment vessel 170/housing 172.

With continued reference to FIG. 3, the housing 172 also has an internal chamber or cavity 180 therein for storing a supply of an ink composition 32. In addition, the housing 172 further includes an outwardly-extending tubular member 182 which passes through the panel member 176 and, in a preferred embodiment, is integrally formed therein. The term "tubular" as used throughout this description shall be defined to encompass a structure which includes at least one or more central passageways therethrough that are surrounded by an outer wall. The tubular member 182 incorporates the inlet/outlet port 178 therein as illustrated in FIG. 3 which provides access to the internal cavity 180 inside the housing 172.

The tubular member 182 positioned within the panel member 176 of the housing 172 has an outer section 184 which is located outside of the housing 172 and an inner section 186 that is located within the ink composition 32 in the internal cavity 180 (FIG. 3.) The outer section 184 of the tubular member 182 is operatively attached by adhesive materials (e.g. conventional cyanoacrylate or epoxy compounds), frictional engagement, and the like to a tubular ink transfer conduit 190 positioned within the port 178 shown schematically in FIG. 3. In the embodiment of FIG. 3, the ink transfer conduit 190 includes a first end 192 which is attached using the methods listed above to and within the port 178 in the outer section 184 of the tubular member 182. The ink transfer conduit 190 further includes a second end 194 that is operatively and remotely attached to a printhead 196 which may involve a number of different designs, configurations, and systems including those associated with printhead 80 illustrated in FIG. 1 which shall be considered equivalent to printhead 196. All of these components are appropriately mounted within a selected printer unit (including printer unit 160) at predetermined locations therein, depending on the type, size, and overall configuration of the entire ink delivery system. It should also be noted that the ink transfer conduit 190 may include at least one optional in-line pump of conventional design (not shown) for facilitating the transfer of ink.

The systems and components presented in FIGS. 1–4 are illustrative in nature. They may, in fact, include additional operating components depending on the particular devices under consideration. The information provided above shall not limit or restrict the present invention and its various embodiments. Instead, the systems of FIGS. 1–4 may be varied as needed and are presented entirely to demonstrate the applicability of the claimed invention to ink delivery units which employ many different arrangements of components. In this regard, any discussion of particular ink delivery systems, ink containment vessels, and related data shall be considered representative only. This situation also applies to the commercial sources recited above involving the various materials listed herein, with such sources being subject to change and other sources also being applicable without limitation.

B. A General Review of the Resistor Elements and Associated Structures within a Conventional Printhead This section will provide a comprehensive discussion for background information purposes of the internal portions of a typical/conventional printhead (including the printhead 80 discussed above) with particular reference to the heating resistors and the interconnect structures attached thereto. The following description shall not limit the invention in any respect and is provided for example purposes only. Likewise, it shall again be understood that the present invention as described in subsequent sections of this discussion is prospectively applicable to a wide variety of different thermal inkjet systems and printhead units provided that, at a minimum, they include a support structure and at least one resistor element thereon which is used to selectively heat ink compositions for delivery to a print media material.

Figure 4:
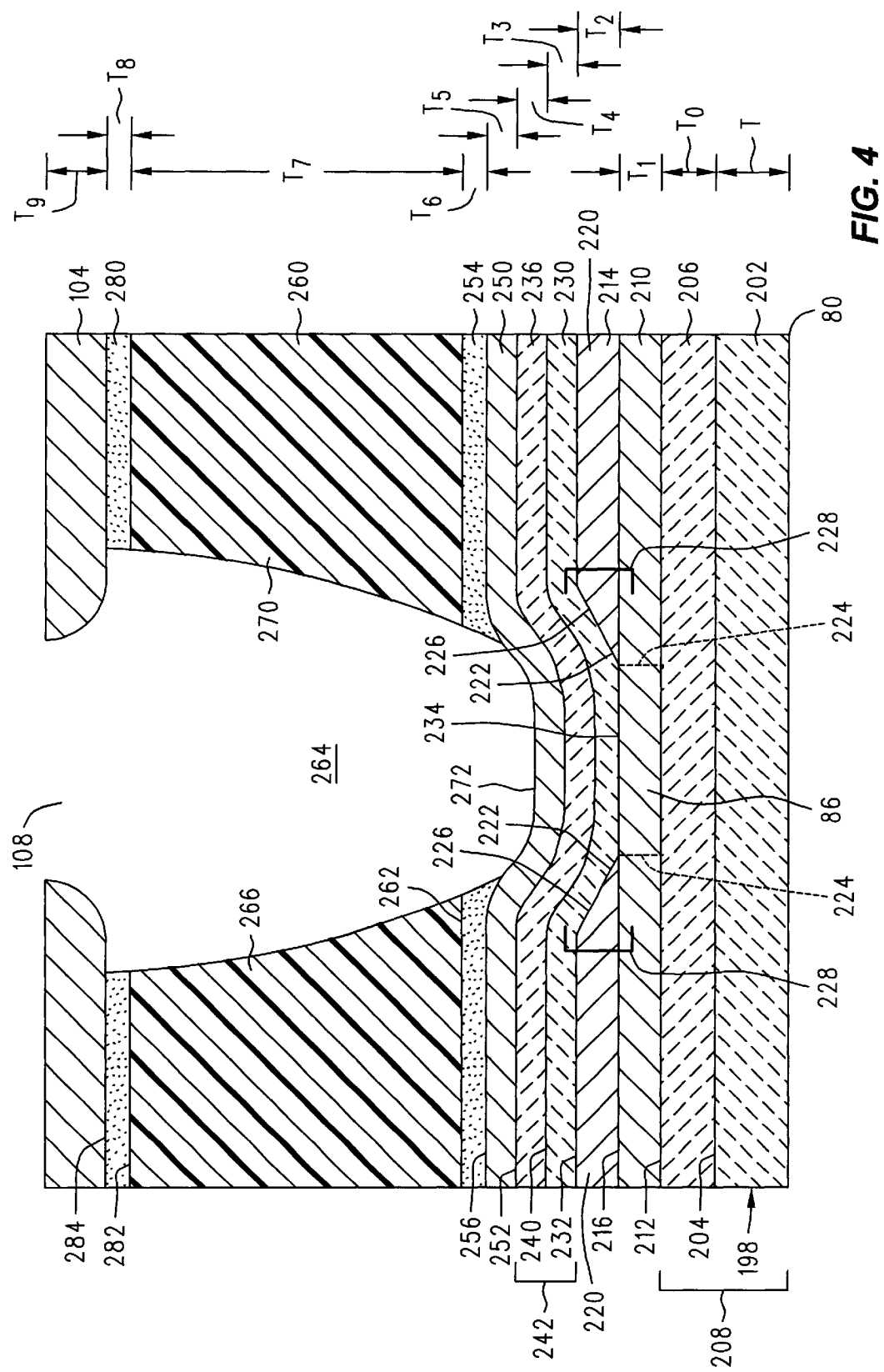
FIG. 4 is a schematically-illustrated, enlarged cross-sectional view of the circled region in FIG. 1 (in an assembled format) taken along line 4—4. This figure illustrates the components of a conventional thermal inkjet printhead system with particular reference to a selected heating resistor and the interconnect structures associated therewith.

With reference to FIG. 4, a portion 198 of the printhead 80 is cross-sectionally illustrated. For reference purposes, the portion 198 involves the components and structures encompassed within the circled region 200 presented in FIG. 1. The components illustrated in FIG. 4 are shown in an assembled configuration. Likewise, it shall be understood that the various layers provided in FIG. 4 are not necessarily drawn to scale and are enlarged for the sake of clarity. In accordance with the cross-sectional view of FIG. 4, a representative resistor 86 (also characterized herein as a "resistor element" as defined above) is schematically shown along with the various material layers which are positioned above and below the resistor 86 (including the orifice plate 104). All of these structures (and the other layers outlined in this section) are likewise illustrated and fully explained (along with applicable construction techniques) in the following patents which are incorporated herein by reference: U.S. Pat. Nos. 4,535,343 to Wright et al. and U.S. Pat. No. 5,122,812 to Hess et al. However, for the sake of clarity and in order to provide a fully enabling disclosure, the following additional information will now be presented.

With continued reference to FIG. 4, the printhead 80 (namely, portion 198) first includes a substrate 202 which is optimally produced from elemental silicon [Si]. The silicon employed for this purpose may be monocrystalline, polycrystalline, or amorphous. Other materials can be used in connection with the substrate 202 without limitation including but not limited to alumina [$Al_2O_3$], silicon nitride [$Si_3N_4$] having a layer of silicon carbide [SiC] thereon, various metals (e.g. elemental aluminum [Al]), and the like (along with mixtures of these compositions). In a preferred and representative embodiment, the substrate 202 will have a thickness "T" of about 500–925 μm, with this range (and all of the other ranges and numerical parameters presented herein) being subject to change as needed in accordance with routine preliminary testing unless otherwise noted. The size of substrate 202 may vary substantially, depending on the type of printhead system under consideration. However, in a representative embodiment (and with reference to FIG. 1), the substrate 202 will have an exemplary width "W" of about 3–15 mm and length "$L_1$" of about 5–40 mm. Incidentally, the substrate 202 in FIG. 4 is substantially equivalent to the substrate 82 discussed above in Section "A", with the substrate 82 being renumbered in this section for the sake of clarity.

Next, positioned on the upper surface 204 of the substrate 202 is an optional dielectric base layer 206 which is designed to electrically insulate the substrate 202 from the resistor 86 shown in FIG. 4. The term "dielectric" as conventionally used herein again involves a material which is an electrical insulator or in which an electric field can be maintained with minimum power dissipation.

In standard thermal inkjet systems, the base layer 206 is preferably made from silicon dioxide ($SiO_2$) which, as discussed in U.S. Pat. No. 5,122,812, was traditionally formed on the upper surface 204 of the substrate 202 when the substrate 202 was produced from silicon [Si]. The silicon dioxide used to form the base layer 206 was fabricated by heating the upper surface 204 to a temperature of about 600–1000° C. in a mixture of silane, oxygen, and argon. This process is further discussed in U.S. Pat. No. 4,513,298 to Scheu which is likewise incorporated herein by reference. Thermal oxidation processes and other basic layer formation techniques described herein including chemical vapor deposition (CVD), plasma-enhanced chemical vapor deposition (PECVD), low-pressure chemical vapor deposition (LPCVD), and masking/imaging processes used for layer definition/formation are well known in the art and described in a book entitled Elliott, D. J., *Integrated Circuit Fabrication Technology*, McGraw-Hill Book Company, New York (1982) - (ISBN No. 0-07-019238-3), pp. 1–40, 43–85, 125–143, 165–229, and 245–286 which is incorporated herein by reference for background information purposes. In a representative and non-limiting embodiment, the base layer 206 (if used) will have a thickness To (FIG. 4) of about 10,000–24,000 Å as outlined in U.S. Pat. No. 5,122,812.

At this point, it shall be understood that the substrate 202 having the base layer 206 thereon will be collectively designated as a "support structure" 208, with the term "support structure" as used herein encompassing (1) the substrate 202 by itself if no base layer 206 is employed; and (2) the substrate 202 and any other materials thereon which form a composite structure on which the resistors 86 reside or are otherwise positioned. In this regard, the term "support structure" shall generally involve the layer or layers of materials (whatever they may be) on which the resistor elements are placed.

The remainder of the layers and fabrication stages associated with the printhead 80 as illustrated in FIG. 4 are likewise conventional in nature except as noted below (e.g. see Section "C"). The conventional technology associated with these items is again discussed in U.S. Pat. No. 4,535,343 to Wright et al. and U.S. Pat. No. 5,122,812 to Hess et al. With continued reference to FIG. 4, a resistive layer 210 (also characterized herein as a "layer of resistive material") is provided which is positioned/formed on the support structure 208, namely, the upper surface 212 of the base layer 206 or directly on the upper surface 204 of the substrate 202 if the base layer 206 is not employed. In this regard, when it is stated that the resistive layer 210, the resistors 86 used in conventional systems, or the resistor elements of present invention are "positioned", "located", "placed", "oriented", "operatively attached", "affixed", "operatively connected", "formed", and otherwise secured to the support structure 208, this shall encompass a number of situations. These situations include those in which (1) the resistive layer 210/resistors 86 are secured directly on and to the upper surface 204 of the substrate 202 without any intervening material layers therebetween; or (2) the resistive layer 210/resistors 86 are supported by the substrate 202 in which one or more intermediate material layers (e.g. the base layer 206 and any others) are nonetheless located between the substrate 202 and resistive layer 210/resistors 86. Both of these alternatives shall be considered equivalent and encompassed within the present claims. The resistive layer 210 is conventionally used to create or "form" the resistors in the system (including the resistor element 86 shown in the conventional design of FIG. 4), with the steps that are employed for this purpose being described later in this section. The resistive layer 210 (and resistor elements produced therefrom including resistor 86) will have a thickness "$T_1$" of about 250–10,000 Å in a typical and conventional thermal inkjet printhead.

A number of different materials have been used to fabricate the resistive layer 210 in standard printhead systems without limitation. For example, as previously noted, a representative composition suitable for this purpose includes but is not limited to a mixture of elemental aluminum [Al] and elemental tantalum [Ta] (e.g. "TaAl") which is known in the art for thin-film resistor fabrication as discussed in U.S. Pat. No. 5,122,812. This material is typically formed by sputtering a pressed powder target of aluminum and tantalum onto the upper surface 212 of the base layer 206 in the system of FIG. 4. In a preferred embodiment, the final mixture which is again designated hereinafter as "TaAl" consists of about 40–60 atomic (At.) % tantalum (about 50 At. %=optimum) and about 40–60 atomic (At.) % aluminum (about 50 At. %=optimum).

Other compositions which have been employed as resistive materials in the resistive layer 210 include the following exemplary and non-limiting substances: undoped or doped polycrystalline silicon [Si] (with a number of "dopants" being applicable including but not limited to phosphorous [P], boron [B], arsenic [Ar], antimony [An], and the like), tantalum nitride [$Ta_2N$], nichrome [NiCr], hafnium bromide [$HfBr_4$], elemental niobium [Nb], elemental vanadium [V], elemental hafnium [Hf], elemental titanium [Ti], elemental zirconium [Zr], elemental yttrium [Y], and mixtures thereof. In accordance with the information provided below in Section "C", the claimed invention is primarily (but not exclusively) concerned with the use of resistors 86 fabricated from undoped or (preferably) doped polycrystalline silicon, with this material, the various types thereof, and details involving the doping process being discussed extensively in Section "C". The polycrystalline silicon resistors 86 and the specialized interconnection system associated therewith offers many benefits and improvements compared with the resistor assemblies employed in prior printheads (including the structure of FIG. 4 and others). These benefits include cooler and more uniform internal temperature profiles, improved reliability, greater energy efficiency, and the like.

The resistive layer 210 in a conventional thermal inkjet printhead can be applied in position using a number of different technologies (depending on the resistive materials under consideration) ranging from sputtering processes when metal compositions are involved to the various deposition procedures (including low pressure chemical vapor deposition [LPCVD] methods) which are outlined above and discussed in Elliott, D. J., *Integrated Circuit Fabrication Technology*, McGraw-Hill Book Company, New York (1982) - (ISBN No. 0-07-019238-3), pp. 1–40, 43–85, 125–143, 165–229, and 245–286 which is again incorporated herein by reference. For example, as noted in U.S. Pat. No. 5,122,812, LPCVD ("low pressure chemical vapor deposition") technology is particularly appropriate for use in applying silicon as the resistive material within printhead 80.

A typical thermal inkjet printhead will contain up to about 300 individual resistors 86 (FIG. 1) or more, depending on the type and overall capacity of the printhead being produced. However, use of the novel resistors 86 associated with the present invention can result in a printhead structure with as many as about 600–1200 resistors 86 if needed and desired. Although the particular architecture associated with the individual resistors 86 (FIG. 1) in the printhead 80 may be varied considerably as needed in accordance with the type of ink delivery system under consideration, an exemplary "square" resistor 86 (produced from the resistive layer 210) will have a non-limiting length of about 5–100 μm and a width of about 5–100 μm. However, the claimed invention shall not be restricted to any given dimensions in connection with the resistors 86 in the printhead 80. Likewise, the resistors 86 should be capable of heating the ink composition 32 to a temperature of at least about 300° C. or higher, depending on the particular apparatus under consideration and the type of ink being delivered.

With continued reference to FIG. 4, formation of an individual resistor 86 from the conventional resistive layer 210 in accordance with standard thermal inkjet technology will now be described. Specifically, a conductive layer 214 is positioned on the upper surface 216 of the resistive layer 210. The conductive layer 214 as illustrated in FIG. 4 includes dual portions 220 that are separated from each other. The inner ends 222 of each portion 220 actually form the "boundaries" of the resistor 86 as will be outlined further below. The conductive layer 214 (and portions 220 thereof) are produced from at least one conductive metal placed directly on the upper surface 216 of the resistive layer 210 and patterned thereon using conventional photolithographic, sputtering, metal deposition, and other known techniques as generally discussed in Elliott, D. J., *Integrated Circuit Fabrication Technology*, McGraw-Hill Book Company, New York (1982) - (ISBN No. 0-07-019238-3), pp. 1–40, 43–85, 125–143, 165–229, and 245–286. Representative metals (and mixtures thereof) which are suitable for producing the conductive layer 214 will be listed later in this section.

As previously noted and illustrated in FIG. 4, the conductive layer 214 (which is discussed in considerable detail in U.S. Pat. No. 5,122,812) includes dual portions 220 each having inner ends 222. The distance between the inner ends 222 defines the boundaries which create the resistor 86 shown in FIGS. 1 and 4. In particular, the resistor 86 consists of the section of resistive layer 210 that spans (e.g. is between) the inner ends 222 of the dual portions 220 of the conductive layer 214. The boundaries of the resistor 86 are shown in FIG. 4 at dashed vertical lines 224.

As stated in U.S. Pat. No. 5,122,812, the resistor 86 operates as a "conductive bridge" between the dual portions 220 of the conductive layer 214 and effectively links them together from an electrical standpoint. As a result, when electricity in the form of an electrical impulse or signal from the printer unit 160 (discussed above) passes through the "bridge" structure formed by the resistor 86, heat is generated in accordance with the resistive character of the materials which are used to fabricate the resistive layer 210/resistor 86. From a technical standpoint, the presence of the conductive layer 214 over the resistive layer 210 essentially defeats the ability of the resistive material (when covered) to generate significant amounts of heat. Specifically, the electrical current, flowing via the path of least resistance, will be confined to the conductive layer 214, thereby generating minimal thermal energy. Thus, the resistive layer 210 only effectively functions as a "resistor" (e.g. resistor 86) where it is "uncovered" between the dual portions 220 as illustrated in FIG. 4.

In addition, with continued reference to FIG. 4, the inner ends 222 of the conductive layer 214 which are produced using the conventional methods discussed above each traditionally have an angularly-sloped surface 226. This sloped surface 226 (which is directly adjacent to and in contact with the resistor 86) creates a non-planar region that is located between brackets 228 (FIG. 4) which is difficult to completely and effectively cover with the overlying protective/passivation layers in the system as outlined above. The presence of non-planar geometry within the regions of the printhead 80 adjacent the resistor 86 can increase the likelihood of defect formation in the subsequently-applied passivation layer(s) including cracks, pinholes, fissures and the like. Such defects can defeat the entire purpose of the passivation layer(s), thereby leading to undesired ink contact with the resistor 86 and chemical deterioration thereof. As discussed in considerable detail in Section "C", the present invention employs a novel interconnection system which, in a preferred embodiment, results in a substantially planar topography in the vicinity of the resistor 86 and thereover, thus avoiding the difficulties listed above.

Regarding the conventional system of FIG. 4, many different compositions can be used to fabricate the conductive layer 214 including but not limited to the following representative materials: elemental aluminum [Al], elemental gold [Au], elemental copper [Cu], elemental tungsten [W], elemental silicon [Si], and/or mixtures thereof. In addition (as outlined in U.S. Pat. No. 5,122,812), the conductive layer 214 may optionally be produced from a selected composition which is combined with various materials or "dopants" including elemental copper and/or elemental silicon (assuming that other compositions are employed as the primary component[s] in the conductive layer 214). If elemental aluminum is used as the main constituent in the conductive layer 214 (with elemental copper being added as a "dopant"), the copper is specifically designed to control problems associated with electromigration. If elemental silicon is used as an additive in an aluminum-based system (either alone or combined with copper), the silicon will effectively prevent side reactions between the aluminum and other silicon-containing layers in the system. An exemplary and preferred material which is typically used to produce the conductive layer 214 will contain about 95.5% by weight elemental aluminum, about 3.0% by weight elemental copper, and about 1.5% by weight elemental silicon. Regarding the overall thickness "$T_2$" of the conductive layer 214 (and dual portions 220 associated therewith as illustrated in the standard system of FIG. 4), a representative value suitable for this structure will be about 2000–10,000 Å. However, all of the information provided above including the preferred thickness ranges may be varied as needed in accordance with preliminary pilot testing involving the particular ink delivery system under consideration and its desired capabilities. With continued reference to FIG. 4, a number of different layers can be placed in position over the resistor 86 without limitation. Accordingly, the following description shall involve only one type of conventional printhead which is being discussed for example purposes. Positioned over and above the dual portions 220 of the conductive layer 214 and the resistor 86 is an optional first passivation layer 230. Specifically, the first passivation layer 230 is placed/deposited directly on (1) the upper surface 232 of each portion 220 associated with the conductive layer 214; and (2) the upper surface 234 of the resistor 86. The main function of the first passivation layer 230 (if used as determined by preliminary pilot testing) is to protect the resistor 86 (and the other components listed above) from the corrosive effects of the ink composition 32 used in the cartridge 10. The protective function of the first passivation layer 230 is of particular importance to the integrity of the resistor 86 since any physical damage to this structure can dramatically impair its basic operational capabilities. A number of different materials can be employed in connection with the first passivation layer 230 including but not limited to silicon dioxide [$SiO_2$], silicon nitride [$Si_3N_4$], aluminum oxide [$Al_2O_3$], and silicon carbide [SiC]. In a preferred embodiment, silicon nitride is used which is optimally applied using plasma-enhanced chemical vapor deposition (PECVD) techniques to deliver the silicon nitride to the upper surface 232 of each portion 220 associated with the conductive layer 214 and the upper surface 234 of the resistor 86. This may be accomplished by using a conventional PECVD system to apply silicon nitride resulting from the decomposition of silane mixed with ammonia at a pressure of about 2 torr and temperature of about 300–400° C. as discussed in U.S. Pat. No. 5,122,812 which is again incorporated herein by reference. While the claimed invention shall not be restricted or otherwise limited to passivation layers 230 made from any given construction materials, the compounds listed above provide best results. Likewise, an exemplary thickness "$T_3$" associated with the first passivation layer 230 is about 1000–10,000 Å. This value may nonetheless be varied in accordance with routine preliminary testing involving the particular printhead system under consideration.

Next, in a preferred embodiment designed to provide a maximum degree of protective capability, an optional second passivation layer 236 is positioned directly on the upper surface 240 of the first passivation layer 230 discussed above. The second passivation layer 236 (the use of which shall again be determined by preliminary pilot testing) is preferably manufactured from silicon carbide [SiC], although silicon nitride [$Si_3N_4$], silicon dioxide [$SiO_2$], or aluminum oxide [$Al_2O_3$] may also be employed for this purpose. While a number of different techniques can be used to deposit the second passivation layer 236 on the first passivation layer 230 (as is the case with all of the various material layers discussed herein), plasma-enhanced chemical vapor deposition techniques (PECVD) provide optimal results at this stage. If silicon carbide is involved, for example, the PECVD process is accomplished in a representative embodiment by using a combination of silane and methane at a temperature of about 300–450° C. The second passivation layer 236 is again employed to augment the protective capabilities of the first passivation layer 230 by providing an additional chemical barrier to the corrosive effects of the ink composition 32 as previously noted. While the claimed invention shall not be restricted to any particular dimensions in connection with the second passivation layer 236, a representative thickness "$T_4$" for this structure is about 1000–10,000 Å. As a result, a highly-effective "dual passivation structure" 242 is created which consists of (1) the first passivation layer 230; and (2) the second passivation layer 236.

With continued reference to FIG. 4, the next layer in the representative printhead 80 involves an optional electrically conductive anti-cavitation layer 250 which is applied to the upper surface 252 of the second passivation layer 236. The anti-cavitation layer 250 (the use of which is again determined by preliminary pilot testing) provides an even further degree of protection regarding the underlying structures in the printhead 80. Specifically, it is used to impart physical damage resistance to the layers of material beneath the anti-cavitation layer 250 in the printhead 80 including but not limited to the first and second passivation layers 230, 236 and the resistor 86 thereunder. In accordance with the protective function of the anti-cavitation layer 250, it is optimally made from a selected metal including but not limited to the following preferred materials: elemental tantalum [Ta], elemental molybdenum [Mo], elemental tungsten [W], and mixtures/alloys thereof. While a number of different techniques can be employed for depositing the anti-cavitation layer 250 in position on the upper surface 252 of the second passivation layer 236 in the embodiment of FIG. 4, this step is optimally accomplished in accordance with standard sputtering methods and/or other applicable procedures as discussed in Elliott, D. J., *Integrated Circuit Fabrication Technology*, McGraw-Hill Book Company, New York (1982) - (ISBN No. 0-07-019238-3), pp. 1–40, 43–85, 125–143, 165–229, and 245–286. Likewise, in a non-limiting exemplary embodiment designed to provide optimum results (which is subject to change in accordance with preliminary testing involving the particular structures under consideration), the anti-cavitation layer 250 has a preferred thickness "$T_5$" of about 1000–6000 Å.

At this stage, a number of additional components are employed within the printhead 80 which will now be discussed with particular reference to FIG. 4. As illustrated in FIG. 4 and outlined in U.S. Pat. No. 4,535,343, an optional first adhesive layer 254 is applied in position on the upper surface 256 of the anti-cavitation layer 250 which may involve a number of different compositions without limitation. Representative materials suitable for this purpose include but are not limited to conventional epoxy resin materials, standard cyanoacrylate adhesives, silane coupling agents, and the like. The first adhesive layer 254 is again considered to be "optional" in that a number of the materials which may be employed in connection with the overlying barrier layer (described below) will be substantially "self-adhesive" relative to the anti-cavitation layer 250. A decision to use the first adhesive layer 254 shall therefore be determined in accordance with routine preliminary testing involving the particular printhead components under consideration. If used, the first adhesive layer 254 may be applied to the upper surface 256 of the anti-cavitation layer 250 by conventional processes including but not limited to spin coating, roll coating, and other known application materials which are appropriate for this purpose. While the first adhesive layer 254 may be optional in nature, it can be employed as a "default" measure for precautionary reasons to automatically ensure that the overlying barrier layer (discussed below) is securely retained in position. If, in fact, the first adhesive layer 254 is used, it will have an exemplary thickness "$T_6$" of about 100–1000 Å.

Next, a specialized composition is provided within the printhead 80 which is characterized herein as an ink barrier layer 260. The barrier layer 260 is applied in position on the upper surface 262 of the first adhesive layer 254 (if used) or on the upper surface 256 of the anti-cavitation layer 250 if the first adhesive layer 254 is not employed. The barrier layer 260 provides a number of important functions including but not limited to additional protection of the components thereunder from the corrosive effects of the ink composition 32 and the minimization of "cross-talk" between adjacent resistors 86 in the printing system. Of particular interest is the protective function of the barrier layer 260 which electrically insulates the circuit elements 90/resistors 86 (FIG. 1) from each other and other adjacent parts of the printhead 80 so that short circuits and physical damage to these components are prevented. In particular, the barrier layer 260 functions as an electrical insulator and "sealant" which covers the circuit elements 90 and prevents them from coming in contact with the ink materials (ink composition 32 in this embodiment). The barrier layer 260 also protects the components thereunder from physical shock and abrasion damage. These benefits ensure consistent and long-term operation of the printhead 80. Likewise, the architectural features and characteristics of the barrier layer 260 illustrated in FIG. 4 facilitate the precise formation of a discrete "firing chamber" 264 in the printhead 80. The firing chamber 264 involves the particular region within the printhead 80 where ink materials (namely, ink composition 32) are heated by the resistor 86, followed by bubble nucleation and expulsion onto the print media material 150.

Many different chemical compositions may be employed in connection with the ink barrier layer 260, with high-dielectric organic compounds (e.g. polymers or monomers) being preferred. Representative organic materials which are suitable for this purpose include but are not restricted to commercially-available acrylate photoresists, photoimagable polyimides, thermoplastic adhesives, and other comparable materials that are known in the art for ink barrier layer use. For example, the following representative, non-limiting compounds suitable for fabricating the ink barrier layer 260 are as follows: (1) dry photoresist films containing half acrylol esters of bis-phenol; (2) epoxy monomers; (3) acrylic and melamine monomers [e.g. those which are sold under the trademark "Vacrel" by E. I. DuPont de Nemours and Company of Wilmington, Del. (USA)]; and (4) epoxy-acrylate monomers [e.g. those which are sold under the trademark "Parad" by E. I. DuPont de Nemours and Company of Wilmington, Del. (USA)]. Further information regarding barrier materials is provided in U.S. Pat. No. 5,278,584 which is incorporated herein by reference. The claimed invention shall not be restricted to any particular barrier compositions or methods for applying the barrier layer 260 in position. Regarding preferred application methods, the barrier layer 260 is traditionally delivered by high speed centrifugal spin coating devices, spray coating units, roller coating systems, and the like. However, the particular application method for any given situation will depend on the barrier layer 260 under consideration.

With continued reference to FIG. 4, the barrier layer 260 as cross-sectionally illustrated in this figure consists of two sections 266, 270 which are spaced apart from each other in order to form the firing chamber 264 as discussed above. Positioned at the bottom 272 of the firing chamber 264 is the resistor 86 and layers thereon (including the first passivation layer 230, the second passivation layer 236, and the anti-cavitation layer 250). Heat is imparted to the ink materials (e.g. ink composition 32) within the firing chamber 264 from the resistor 86 through the above-listed layers 230, 236, and 250. While the ultimate thickness and architecture associated with the barrier layer 260 may be varied as needed based on the type of printhead being employed, it is preferred that the barrier layer 260 have a representative, non-limiting thickness "$T_7$" of about 5–30 μm.

Next, an optional second adhesive layer 280 is provided which is positioned on the upper surface 282 of the ink barrier layer 260. Representative materials suitable for use in connection with the second adhesive layer 280 include but are not limited to conventional epoxy resin materials, standard cyanoacrylate adhesives, silane coupling agents, and the like. The second adhesive layer 280 is again considered to be "optional" in that a number of the materials which may be employed in connection with the overlying orifice plate 104 (discussed below) will be substantially "self-adhesive" relative to the barrier layer 260. A decision to use the second adhesive layer 280 shall therefore be determined in accordance with routine preliminary testing involving the particular printhead components under consideration. If used, the second adhesive layer 280 may be applied to the upper surface 282 of the barrier layer 260 by conventional processes including but not limited to spin coating, roll coating, and other known application methods which are suitable for this purpose. While the second adhesive layer 280 may be optional in nature, it can be employed as a "default" measure for precautionary reasons to automatically ensure that the overlying orifice plate 104 is securely retained in position. If, in fact, the second adhesive layer 280 is used, it will have an exemplary thickness "$T_8$" of about 100–1000 Å.

It should also be noted that the second adhesive layer 280 may, in fact, involve the use of uncured polyisoprene photoresist compounds as recited in U.S. Pat. No. 5,278,584 (incorporated herein by reference), as well as (1) polyacrylic acid; or (2) a selected silane coupling agent. The term "polyacrylic acid" shall be defined to involve a compound having the following basic chemical structure $[CH_2CH(COOH)_n]$ wherein n=25–10,000. Polyacrylic acid is commercially available from numerous sources including but not limited to the Dow Chemical Corporation of Midland, Mich. (USA). A number of silane coupling agents which are suitable for use herein include but are not limited to commercial products sold by the Dow Chemical Corporation of Midland, Mich. (USA) [product nos. 6011, 6020, 6030, and 6040], as well as OSI Specialties of Danbury, Conn. (USA) [product no. "Silquest" A-1100]. However, the above-listed materials are again provided for example purposes only and shall not limit the invention in any respect. Finally, as illustrated in FIG. 4, the orifice plate 104 is secured to the upper surface 284 of the second adhesive layer 280 or on the upper surface 282 of the barrier layer 260 if the second adhesive layer 280 is not employed. In addition to the various materials discussed above in connection with the orifice plate 104 (including the use of a structure made from gold-plated nickel [Ni]), a substantial number of additional compositions can be employed in connection with the orifice plate 104 including metallic structures made of, for example, elemental nickel [Ni] coated with elemental rhodium [Rh]. Likewise, the orifice plate 104 can be made from the polymeric compositions outlined in U.S. Pat. No. 5,278,584 (discussed above). As shown in FIG. 4 and previously noted, the orifice 108 in the orifice plate 104 is positioned above the resistor 86 and is in partial or (preferably) complete axial alignment (e.g. "registry") therewith so that ink compositions can be effectively expelled from the printhead 80. Likewise, in a preferred and non-limiting embodiment, the orifice plate 104 will have a representative thickness "$T_9$" of about 12–60 μm.

It should likewise be noted at this time that a number of different structures may be used in connection with the orifice plate 104, wherein the claimed invention shall encompass any single or multiple layers of material (made of metal, plastic, etc.) which include at least one opening or orifice therein without limitation. The orifice-containing layer (or layers) of material may be characterized as an "orifice plate", "orifice structure", "top layer", and the like. Furthermore, single or multiple layers of materials may again be employed for this purpose without restriction, with the terms "orifice plate", "orifice structure", etc. being defined to include both single and multi-layer embodiments. Thus, the term "layer" as used in connection with this structure shall encompass both the singular and plural variants thereof. One additional example of an alternative orifice structure involves a situation in which the barrier layer 260 as shown in FIG. 4 is used by itself in the absence of the orifice plate 104 and adhesive layer 280. In other words, a barrier layer 260 is selected which can function as both an ink barrier material and an orifice plate as previously noted.

Having discussed a conventional printhead 80 and its individual components, the resistor system of the claimed invention will now be reviewed in detail. Specifically, the particular features of the invention which depart from the assembly outlined above will be described with particularity.

C. The Novel Resistor Systems of the Present Invention and Representative Fabrication Methods Associated Therewith The novel features and components of the present invention which enable it to provide the benefits listed above will now be discussed. These benefits again range from the production of an interconnection system and associated resistor element(s) that are collectively characterized by a substantially planar surface topography to the ability to control resistance levels independently of layer thickness in a preferred embodiment. As a result, the thickness of the various layers in the system can be optimized to provide low interconnect resistance and improved heat sinking capacity. Likewise, implementation of this invention yields resistor systems with highly optimized "TOE" and "TCR" values as previously defined. All of these goals are achieved in an essentially "automatic" manner which is likewise compatible with the efficient manufacture of thermal inkjet printheads of varying size on a mass production scale. The claimed invention therefore constitutes a substantial advance in the art of ink printing technology which ensures high levels of operating efficiency, excellent print quality, versatility, and increased longevity.

To accomplish these goals, a novel and highly efficient resistor system is provided, with the term "resistor system" again being defined to collectively encompass the selected resistor elements and the interconnect structures associated therewith (circuit traces and the like). It shall be understood that reference numbers used in this section (Section "C") which are carried over from the other sections provided above (Sections "A"–"B") shall signify the use of common subject matter, components, and elements. Likewise, all of the information presented in the previous two sections (Sections "A"–"B") shall be incorporated by reference in the current section (Section "C") and should be considered applicable to the present invention unless otherwise stated herein. Identification of various elements below in the singular shall likewise be applicable to the use of a plurality of such elements as needed and desired. In addition, use of the term "above" regarding the position of one layer in the claimed structure relative to another layer shall signify a situation wherein the particular layer that is "above" the other layer is located at a greater outward distance away from the printhead substrate 202 (FIG. 5) than the other layer in question (which is closer to the substrate 202). The opposite situation shall apply to use of the term "below" herein. The novel subject matter associated with the present invention will be specifically identified in the current section and distinguished where appropriate from the prior system of FIG. 4. Likewise, the resistor system illustrated in the drawing figures subsequent to FIG. 4 shall be applicable to and capable of integration within the printheads 80, 196 of FIGS. 1, 3, and 4 (as well as other comparable devices) in order to provide the benefits recited herein. However, the resistor system of this invention and its associated components shall not be limited to use within printheads 80, 196 and is applicable to a wide variety of different printheads using dissimilar architectural and structural features without limitation.

Figure 34:
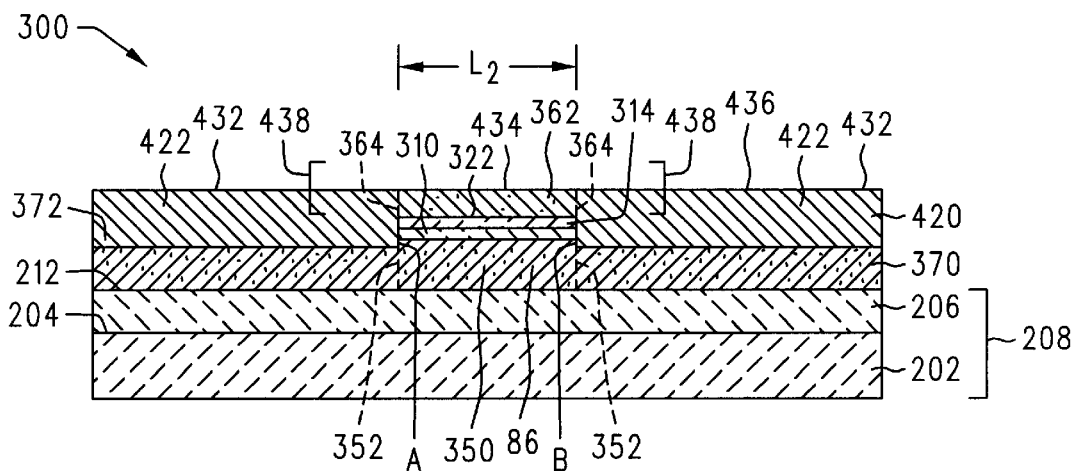
Figure 35:
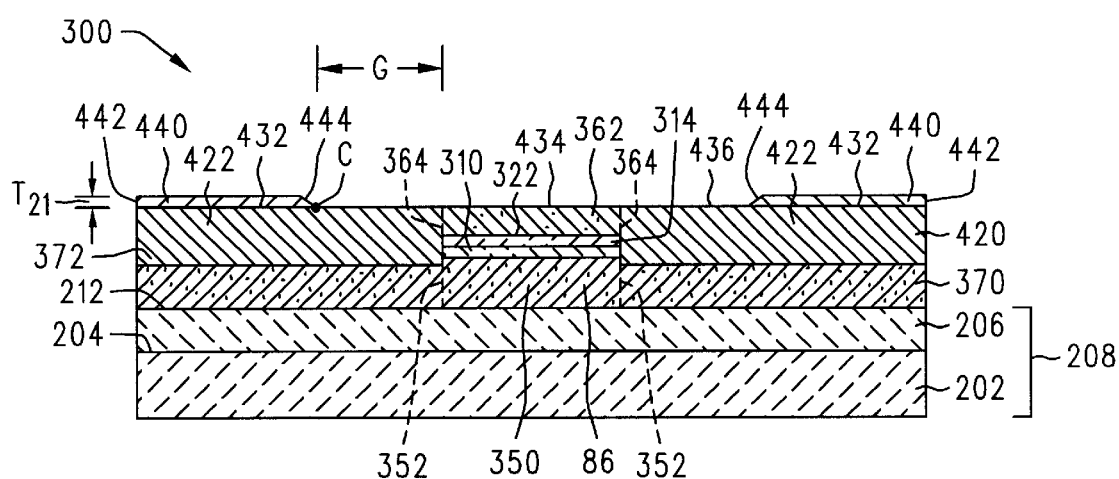

Production of the claimed resistor system shall now be described in a sequential manner leading up to completion of the final product as shown in FIGS. 34–35 at reference number 300. However, the invention discussed herein shall not be restricted to any specific manufacturing methods, with the completed resistor system 300 not being "production-method-specific". Instead, a number of different fabrication techniques can be employed without limitation provided that they produce the final resistor system 300. Representative techniques, processing methods, and other production stages will now be discussed which are provided herein for example purposes only.

Figure 5:
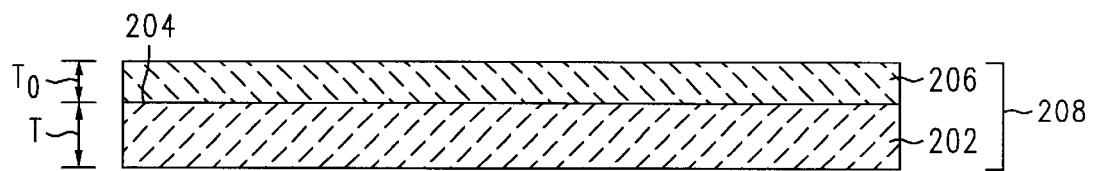
FIGS. 5–35 involve sequential, schematically-illustrated, and enlarged cross-sectional views of the various components and production stages which are used to fabricate the claimed resistor elements and interconnect structures of the present invention in a preferred and non-limiting embodiment. The completed product of FIG. 35 may be integrated into the printhead of FIG. 4 as a replacement for the conventional structures shown therein.

With reference to FIG. 5, the substrate 202 described above is again illustrated which is optimally produced from elemental silicon [Si]. The silicon employed for this purpose may be monocrystalline, polycrystalline, or amorphous. Other materials can be used in connection with the substrate 202 without limitation including but not limited to alumina [$Al_2O_3$], silicon nitride [$Si_3N_4$] having a layer of silicon carbide [SiC] thereon, various metals (e.g. elemental aluminum [Al]), and the like (along with mixtures of these compositions). In a preferred and representative embodiment, the substrate 202 will again have a thickness "T" of about 500–925 μm (FIGS. 4–5), with this range (and all of the other ranges and numerical parameters presented herein) being subject to change as needed in accordance with routine preliminary testing unless otherwise noted. The size of substrate 202 may vary substantially, depending on the type of printhead under consideration. However, in a representative embodiment (and with reference to FIG. 1), the substrate 202 will have an exemplary width "W" of about 3–15 mm and length "$L_1$" of about 5–40 mm. Incidentally, the substrate 202 illustrated in FIGS. 4–5 and beyond is equivalent to the substrate 82 discussed above in Section "A", with the substrate 82 again being renumbered in this section for the sake of clarity.

Next, positioned on the upper surface 204 of the substrate 202 is an optional dielectric base layer 206 (FIG. 5) which is designed to electrically insulate the substrate 202 from the resistor 86 in the overall system which will be discussed later in this section. The term "dielectric" is defined above. In standard thermal inkjet systems, the base layer 206 is preferably made from silicon dioxide ($SiO_2$) which, as indicated in U.S. Pat. No. 5,122,812, was traditionally formed on the upper surface 204 of the substrate 202 when the substrate 202 was produced from silicon [Si]. The silicon dioxide used to form the base layer 206 was fabricated by heating the upper surface 204 to a temperature of about 600–1000° C. in a mixture of silane, oxygen, and argon. This process is further discussed in U.S. Pat. No. 4,513,298 to Scheu which is likewise incorporated herein by reference. Thermal oxidation processes and other basic layer formation techniques that are suitable for use herein including chemical vapor deposition (CVD), plasma-enhanced chemical vapor deposition (PECVD), low-pressure chemical vapor deposition (LPCVD), and masking/imaging processes employed for layer definition/formation are well known in the art and again described in Elliott, D. J., *Integrated Circuit Fabrication Technology*, McGraw-Hill Book Company, New York (1982) - (ISBN No. 0-07-019238-3), pp. 1–40, 43–85, 125–143, 165–229, and 245–286 which is incorporated herein by reference. In a representative and non-limiting embodiment, the base layer 206 (if used) will have a thickness $T_o$ (FIG. 4) of about 10,000–24,000 Å as stated in U.S. Pat. No. 5,122,812.

At this point, it shall be understood that the substrate 202 having the base layer 206 thereon will be collectively designated in this discussion as a "support structure" 208 as previously noted, with the term "support structure" encompassing (1) the substrate 202 by itself if no base layer 206 is employed; or (2) the substrate 202 and any other materials thereon which form a composite structure on which the resistors 86 reside or are otherwise positioned. In this regard, the term "support structure" shall generally involve the layer or layers of materials (whatever they may be) on which the resistors 86 and interconnection components associated therewith are positioned.

Figure 6:
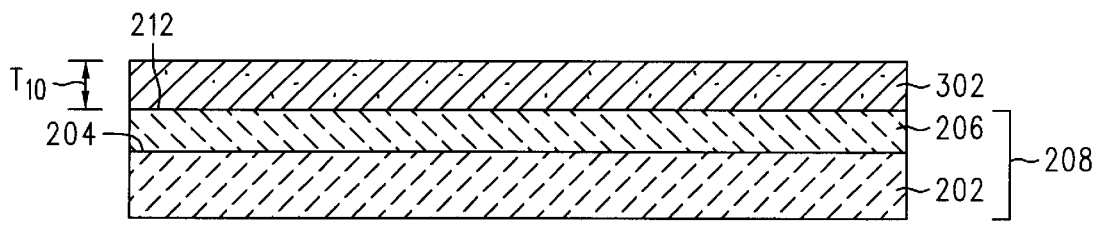

Next, as shown in FIG. 6, an initial, first, or primary layer 302 of material (silicon [Si] in this embodiment) is placed (e.g. operatively attached/applied) to the upper surface 212 of the base layer 206 (or the upper surface 204 of the substrate 202 if the base layer 206 is not employed). In a preferred embodiment which shall not limit the invention in any respect, the layer 302 of silicon shall be of an "amorphous" type which is a known silicon product that basically lacks a completely defined crystalline structure. This material may be applied in position using a number of different techniques including but not limited to chemical vapor deposition (CVD), plasma-enhanced chemical vapor deposition (PECVD), low-pressure chemical vapor deposition (LPCVD), or other comparable processes. Also employed are masking/imaging processes used for layer definition/formation that are again well known in the art and described in Elliott, D. J., *Integrated Circuit Fabrication Technology*, McGraw-Hill Book Company, New York (1982) - (ISBN No. 0-07-019238-3), pp. 1–40, 43–85, 125–143, 165–229, and 245–286. While the claimed invention is not restricted to any given dimensions and numerical parameters which shall be determined in accordance with routine preliminary pilot testing, the primary layer 302 of silicon preferably has a uniform thickness "$T_{10}$" (FIG. 6) of about 500–3000 Å. At this point, it is important to note that at least one section, portion, or region of the primary layer 302 of silicon will ultimately be employed as one or more of the resistors 86 in the completed printhead (printhead 90, 196, or other comparable structures). Likewise, the overall thickness "$T_{10}$" can be varied within the foregoing range (or outside such range as needed) to achieve a desired resistivity level. For the purposes of this invention, the term "resistivity" shall be conventionally defined herein to involve the ratio of the applied electric field to the resultant current density in accordance with the following general formula: "$E=\rho J$" wherein E=applied electric field (V/cm), J=current density (Amperes/$cm^2$), and ρ=resistivity (ohms-cm). As outlined in greater detail below, target resistivity levels in the present case relative to the resistor structures (namely, resistor[s] 86) which are ultimately produced from the primary layer 302 of silicon will be about 2000–4000 μΩ-cm. This value/range may nonetheless be varied as needed and desired in accordance with routine preliminary testing. However, the current embodiment of the claimed invention and its employment of doped polycrystalline silicon resistors in a "buried" orientation is again capable of attaining the precise control of resistor values by selective ion implantation (e.g. "doping") instead of adjusting layer thickness. As a result, layer thickness values can be independently adjusted to achieve different goals including a low degree of "interconnect resistance" (defined above) and improved heat sinking capacity as outlined in this section.

Figure 7:
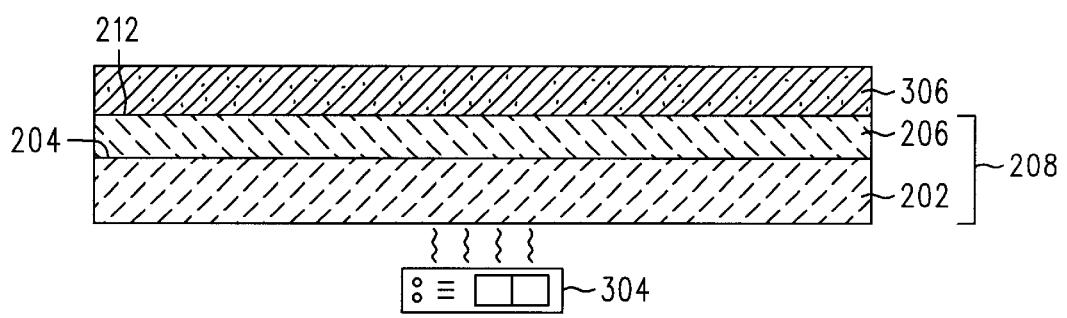

Thereafter, in accordance with FIG. 7, the primary layer 302 of silicon is "annealed" or otherwise heated preferably using a conventional furnace apparatus 304 in order to convert it into an initial, first, or primary layer 306 of polycrystalline silicon. A representative and non-limiting annealing process will involve heating the primary layer 302 of silicon at a temperature of about 550–700° C. over a time period of about 8–20 hours to effectively accomplish conversion. As a result, the primary layer 306 of polycrystalline silicon is fabricated in a process known as "solid phase epitaxy" with a smooth surface and large grain size.

Other annealing techniques which accomplish equivalent results may also be employed for this purpose including but not limited to the use of a method known as "scanning laser annealing" or "scanning laser recrystallization of amorphized polysilicon" which employs a scanning excimer laser as generally discussed in Song, H., et al., "Single-crystal Si islands on $SiO_2$ obtained via excimer-laser irradiation of a patterned Si film", *Appl. Phys. Lett.,* 68(22):3165–3167 (May 1996) which is incorporated herein by reference. This type of process is also generally discussed in, for example, Colinge, J. P., et al., "Use of Selective Annealing for Growing Very Large Grain Silicon on Insulator Films", *Appl. Phys. Lett.,* 41(4):346–347 (Aug. 15, 1982); Lam, H. W., et al., "Characteristics of MOSFETS Fabricated in Laser-Recrystallized Polysilicon Islands with a Retaining Wall Structure on an Insulating Substrate", *IEEE Electron Device Letters,* Vol. EDL-1, No. 10, pp. 206–208 (October 1980); and Biegelsen, D. K., et al., "Laser-induced Crystallization of Silicon Islands on Amorphous Substrates: Multilayer Structures", *Appl. Phys. Lett.,* 38(3):150–152 (Feb. 1, 1981) which are all incorporated herein by reference. Again, a number of different methods can be employed in connection with the annealing stages in this case (including but not limited to the processes listed above, as well as standard "rapid thermal annealing" techniques which are known in the art for this purpose.) It shall be understood that the discussion provided above regarding scanning laser annealing is general in nature with the foregoing literature citations providing additional information if needed. In this regard, the claimed process and resistor systems shall not be restricted to any particular annealing technologies as noted above, with the furnace-based system illustrated in FIG. 7 providing excellent results and being entirely suitable for use herein. For reference purposes, the term "polycrystalline silicon" traditionally involves a silicon material containing an aggregate of multiple crystals. As noted above, the ultimate goal at this stage is to fabricate a primary layer 306 of material (namely, polycrystalline silicon) having a very smooth surface and a relatively large grain/crystal size therein (with a preferred/typical grain size [diameter] of about 1–5 times the thickness of the initial layer 302 of silicon ["$T_{10}$" as noted above]). In general, polycrystalline silicon is a preferred material for use in the present invention because it is a readily available composition with stable and advantageous properties that is economical to use.

It should likewise be understood that, as an alternative to the sequential conversion process outlined above, the primary layer 306 of polycrystalline silicon could be applied in a single step using one of many techniques including but not limited to chemical vapor deposition (CVD), plasma-enhanced chemical vapor deposition (PECVD), and low-pressure chemical vapor deposition (LPCVD). Regarding any other deposition methods discussed in this section (Section "C"), the above-listed reference by Elliott, D. J. entitled *Integrated Circuit Fabrication Technology,* McGraw-Hill Book Company, New York (1982) - (ISBN No. 0-07-019238-3) may be employed for general guidance and support. However, the in situ method listed above (namely, the conversion of previously-applied material layers) is preferred and provides best results. After this step, a number of different layers are applied which will now be discussed.

Figure 8:
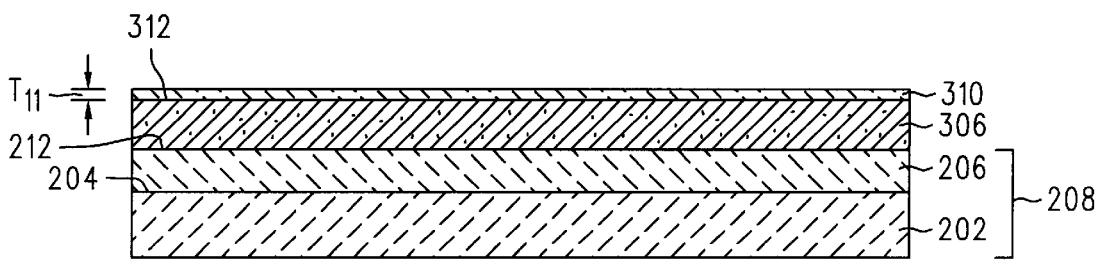

Next, as shown in FIG. 8, an initial, first, or primary layer 310 of silicon oxide material is provided which is deposited over the entire upper surface 312 of the primary layer 306 of polycrystalline silicon. The terms "silicon oxide material", "silicon oxide compound" or, more simply, "silicon oxide" (which shall all be deemed equivalent) as used herein relative to the foregoing layer 310 shall be construed to encompass both (1) silicon dioxide; and/or (2) other oxides of silicon (e.g. compounds containing silicon and oxygen atoms) including but not limited to those that contain at least some silicon atoms that are incompletely bonded to oxygen and the like which result from, for example, the low temperature processes associated with the deposition procedure(s) discussed below. Likewise, when the term "silicon dioxide" is used in connection with the layer 310, this phrase shall also be construed to encompass both silicon dioxide and other oxides of silicon including but not limited to those which contain at least some silicon atoms that are incompletely bonded to oxygen and the like.

The layer 310 of silicon oxide material is optimally formed in a preferred and non-limiting embodiment by delivering a composition known as "tetraethyl orthosilicate" (e.g. "TEOS") to the upper surface 312 of the primary layer 306 of polycrystalline silicon using conventional plasma-enhanced chemical vapor deposition (PECVD) processes. When the "TEOS" is delivered in this fashion, it decomposes/converts into silicon dioxide and/or silicon oxide. As a result, the primary layer 310 of silicon oxide material is formed at a preferred and non-limiting uniform thickness "$T_{11}$" of about 100–300 Å. It should be noted that the term "TEOS" is also conventionally understood by individuals skilled in the art to which this invention pertains to signify the silicon oxide material that is derived from tetraethyl orthosilicate as outlined herein. Accordingly, layer 310 may be identified as a layer of "TEOS", "silicon oxide material" (defined above), or "silicon oxide compound" with the understanding that all of such terms shall, in an equivalent manner, signify the use of silicon dioxide and/or silicon oxide in connection with the layer 310. From a functional standpoint, the layer 310 of silicon oxide material is used as a "stress-relief" oxide layer designed to preserve the structural integrity of the additional layers which will be subsequently applied as outlined below. It also protects the chemical integrity of the underlying primary layer 306 of polycrystalline silicon. It is likewise employed as an "etch stop" layer during subsequent silicon nitride dry etching (discussed below). Furthermore, the present invention shall not be limited to any particular methods for producing the layer 310 of silicon oxide material, with the "TEOS"-based process listed above being only one example.

Figure 9:
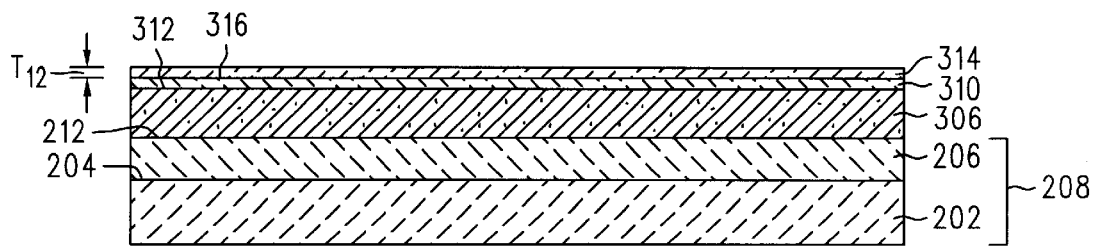

With reference to FIG. 9, the next step in the representative procedure being described in this section involves the application of an initial, first, or primary layer 314 of silicon nitride ($Si_3N_4$ or other stoichiometric variants of this formula) onto the entire upper surface 316 of the layer 310 of silicon oxide material. This step may be achieved using many different techniques including but not limited to conventional low pressure chemical vapor deposition (LPCVD) and/or plasma-enhanced chemical vapor deposition (PECVD) methods at a preferred and non-limiting uniform thickness "$T_{12}$" of about 100–300 Å. From a functional standpoint, the layer 314 of silicon nitride is employed in order to form a "mask" over the region of the structure shown in FIG. 9 which will become the resistor 86 so that it may be properly protected and retain its separate character as outlined below.

Figure 10:
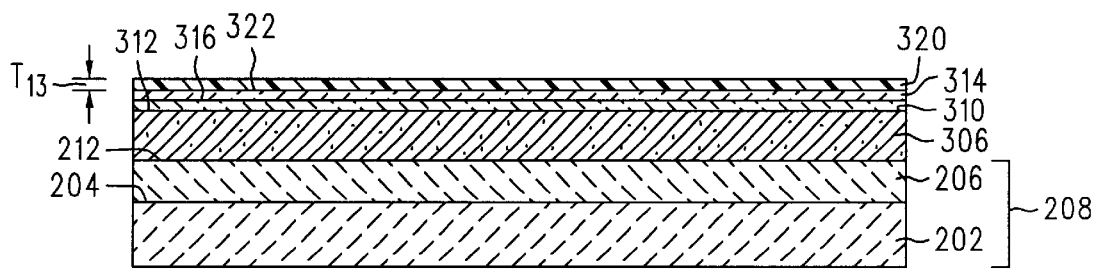

Next, as illustrated schematically in FIG. 10, a series of process steps are initiated which will define the portion, section, zone, or region of the primary layer 306 of polycrystalline silicon that is destined to become the resistor 86 in the completed structure. It shall be understood that the terms "portion", "section", "region", "zone", and the like shall all be considered substantially equivalent and interchangeable throughout this discussion. In particular, at this stage, the general size, shape, and overall geometric configuration of the specific resistor 86 under consideration is defined using standard and conventional photoresist imaging processes which are known in the art for this purpose and again discussed in Elliott, D. J., *Integrated Circuit Fabrication Technology,* McGraw-Hill Book Company, New York (1982) - (ISBN No. 0-07-019238-3), pp. 1–40, 43–85, 125–143, 165–229, and 245–286 (incorporated herein by reference). While the claimed invention shall not be restricted to any given procedure or technique for resistor definition, a representative and preferred processing method will now be presented. As shown in FIG. 10, a selected layer 320 of standard positive photoresist material is applied to the upper surface 322 of the primary layer 314 of silicon nitride. In a representative embodiment, the layer 320 of photoresist material will consist of a commercial product sold under the designation "HPR504" produced by the Olin Chemical Corp. of Norwalk, Conn. (USA) which is applied at a preferred and non-limiting uniform thickness "$T_{13}$" of about 1–2 μm.

Figure 11:
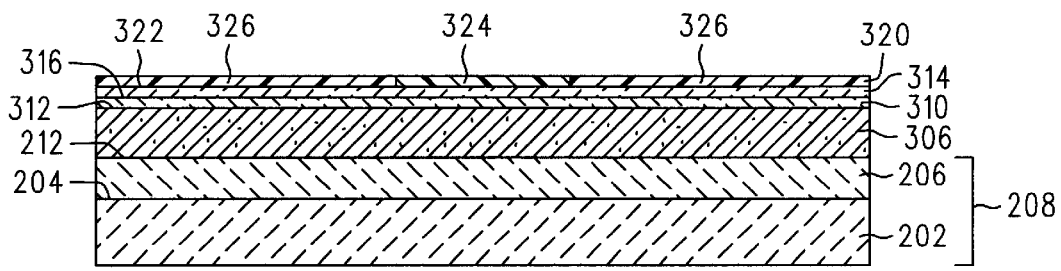

Using standard masking processes which are again well known in the art, the layer 320 of photoresist material is then imaged in a conventional fashion as discussed, for example, in the *Integrated Circuit Fabrication Technology* reference cited above to yield an unexposed region 324 (which is located over the particular portion of the polycrystalline silicon layer 306 that will ultimately become the resistor 86) and exposed regions 326 (FIG. 11). Thereafter, with reference to FIG. 12, the exposed regions 326 along with the underlying primary layers 310, 314 of silicon oxide material and silicon nitride, respectively, are etched away to yield the structure of FIG. 12. While a number of different etching techniques can be employed for this purpose, a preferred procedure involves first removing the exposed regions 326 of the photoresist-containing layer 320 by spraying or immersing the structure of FIG. 11 in a conventional resist developer (e.g., a commercial material known as "HPRD429" which is produced by the Olin Chemical Corp. of Norwalk, Conn. [USA]), followed by rinsing in deionized water. Thereafter, the underlying layer 314 of silicon nitride is removed by the conventional "dry etching" thereof in a fluorine or chlorine gaseous plasma. Finally, the underlying layer 310 of silicon oxide material may be conventionally removed by chemical etching in a hydrofluoric acid (HF) solution. Again, the foregoing procedure is provided for example purposes only and shall be considered non-limiting since various other techniques for accomplishing the above-listed goals may also be employed.

Figure 12:
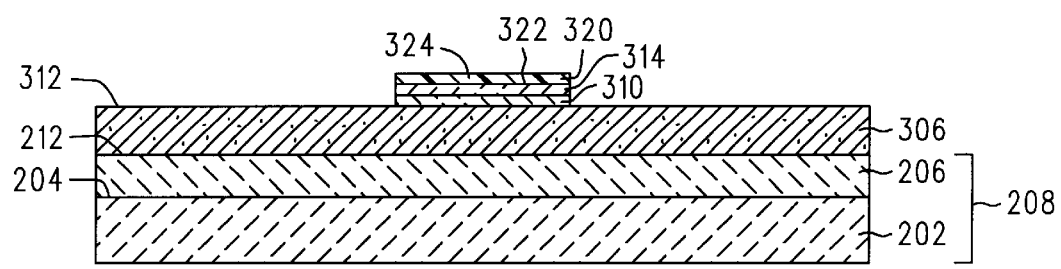
Figure 13:
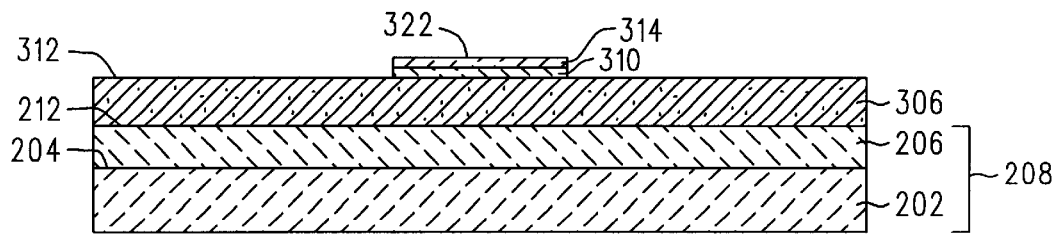

As shown in FIG. 12, the steps described above result in an overall structure wherein the upper surface 312 of the polycrystalline silicon layer 306 is "exposed" (revealed) where the regions 326 of the photoresist-containing layer 320 (and layers 310, 314 of silicon oxide material/silicon nitride thereunder) used to be. Likewise, the particular portion of the primary layer 306 of polycrystalline silicon that remains covered by the unexposed region 324 of the photoresist-containing layer 320, primary layer 314 of silicon nitride, and primary layer 310 of silicon oxide material will ultimately become the resistor 86 in the completed printhead system. Incidentally, at this stage, a number of additional procedural steps are implemented in a preferred and non-limiting embodiment which will now be summarized. First, with reference to FIG. 13, the remaining unexposed region 324 of the photoresist-containing layer 320 is preferably removed using (in a non-limiting embodiment) a two-step process first involving "dry etching" the structure of FIG. 12 in an oxygen plasma and then treating the structure using a "wet cleaning" stage employing, for example, sulfuric peroxide or other comparable materials known in the art for this purpose. Preferably after this step, a material known as "native oxide" is removed from the exposed upper surface 312 of the primary layer 306 of polycrystalline silicon. The term "native oxide" is used to describe a very thin layer of silicon dioxide ($SiO_2$) which resides on the exposed upper surface 312 of the primary layer 306 of polycrystalline silicon. This layer of native oxide (not shown in the drawing figures due to its very small size/thickness which is normally about 10–20 Å or even less) forms "naturally" when the polycrystalline silicon associated with the upper surface 312 is "exposed" to ambient air. The cleaning/removal of native oxide materials from the exposed upper surface 312 is typically accomplished in a non-limiting and representative fashion by applying to the upper surface 312 a buffered solution of hydrofluoric acid (HF). It is desirable to remove native oxide materials using this process or other comparable procedures in order to ensure proper electrical contact between the primary layer 306 of polycrystalline silicon and the material layers thereover.

Figure 14:
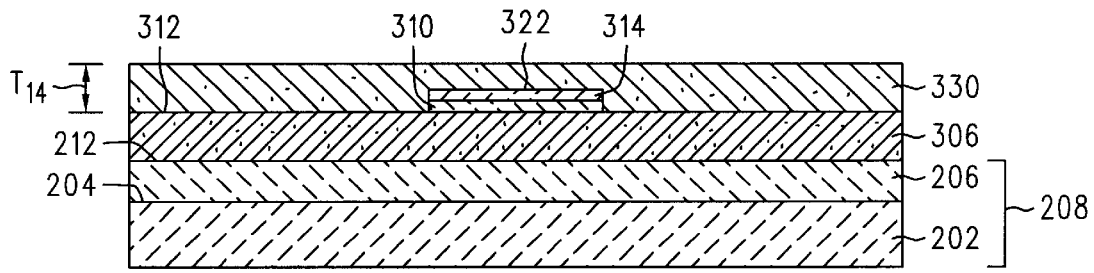

Referring back to the drawing figures, the next step in the novel printhead fabrication process of the present invention is illustrated in FIG. 14. Specifically, an additional or secondary layer 330 of material (silicon [Si] in the current preferred embodiment) is positioned over and above (e.g. operatively attached/placed on) (1) the exposed upper surface 312 of the primary layer 306 of polycrystalline silicon wherever it exists in the structure of FIG. 13; and (2) the exposed upper surface 322 of the primary layer 314 of silicon nitride illustrated in FIG. 13. In particular, the secondary layer 330 of silicon will cover the entire structure of FIG. 13 as shown in FIG. 14. In a preferred embodiment which shall not limit the invention in any respect, the secondary layer 330 of silicon is of an "amorphous" type which, as noted above, is a known silicon product that basically lacks a completely defined crystalline structure. This material may be applied in position using a number of different techniques including but not limited to chemical vapor deposition (CVD), plasma-enhanced chemical vapor deposition (PECVD), low-pressure chemical vapor deposition (LPCVD), or other comparable processes. Also employed are masking/imaging processes used for layer definition/formation that are again well known in the art and described in Elliott, D. J., *Integrated Circuit Fabrication Technology,* McGraw-Hill Book Company, New York (1982) - (ISBN No. 0-07-019238-3), pp. 1–40, 43–85, 125–143, 165–229, and 245–286. While the claimed invention shall not be restricted to any given dimensions and numerical parameters which will be determined in accordance with routine preliminary pilot testing, the secondary layer 330 of material (silicon) optimally has a uniform thickness "$T_{14}$" (FIG. 14) of about 500–3000 Å.

Figure 15:
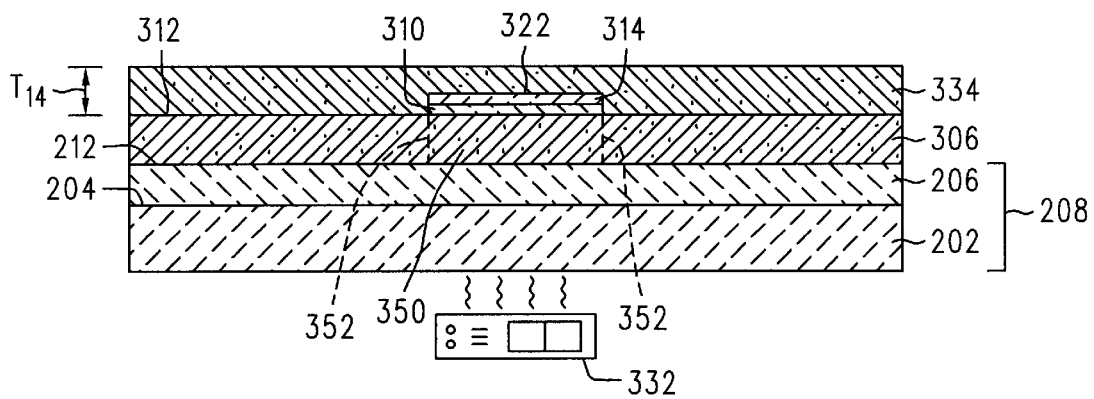

In accordance with FIG. 15, the secondary layer 330 of silicon is thereafter "annealed" or otherwise heated using a conventional furnace apparatus 332 or comparable device in order to convert the layer 330 of FIG. 14 into a secondary layer 334 of polycrystalline silicon (FIG. 15). A representative and non-limiting annealing process will involve heating the secondary layer 330 of silicon at a temperature of about 550–700° C. over a time period of about 8–20 hours to effectively accomplish conversion. As a result of this annealing step, the secondary layer 334 of polycrystalline silicon is produced in a process that is again known as "solid phase epitaxy" with a smooth surface and large grain size (with a preferred/typical grain size [diameter] of about 1–5 times the thickness of the secondary layer 330 of silicon ["$T_{14}$" as noted above]).

Other annealing processes which accomplish equivalent results may also be employed for this purpose including but not limited to the use of "scanning laser annealing" and conventional "rapid thermal annealing" procedures as previously discussed. Scanning laser annealing is again generally described in, for example, Song, H., et al., "Single-crystal Si islands on SiO$_2$ obtained via excimer-laser irradiation of a patterned Si film", *Appl. Phys. Lett.,* 68(22):3165–3167 (May 27, 1996) which is incorporated herein by reference. This type of process is also generally discussed in, for example, Colinge, J. P., et al., "Use of Selective Annealing for Growing Very Large Grain Silicon on Insulator Films", *Appl. Phys. Lett.,* 41(4):346–347 (Aug. 15, 1982); Lam, H. W., et al., "Characteristics of MOSFETS Fabricated in Laser-Recrystallized Polysilicon Islands with a Retaining Wall Structure on an Insulating Substrate", *IEEE Electron Device Letters,* Vol. EDL-1, No. 10, pp. 206–208 (October 1980); and Biegelsen, D. K., et al., "Laser-induced Crystallization of Silicon Islands on Amorphous Substrates: Multilayer Structures", *Appl. Phys. Lett.,* 38(3):150–152 (Feb. 1, 1981) which are all incorporated herein by reference. The selection of any given annealing process at this stage will be determined using routine preliminary testing, with a number of different procedures being potentially applicable.

With continued reference to FIG. 15, the "buried" resistor system associated with the present invention is illustrated in its initial stages. As is clearly shown in FIG. 15, the entire primary layer 306 of polycrystalline silicon (as well as the remaining initial layers 310, 314 of silicon oxide material and silicon nitride) are completely covered by the secondary layer 334 of material (polycrystalline silicon). Incidentally, for reference purposes, the particular portion of the "buried" primary layer 306 of polycrystalline silicon that will ultimately become the resistor 86 in the completed printhead 80, 196 (or other comparable structures) shall be identified hereinafter at reference number 350 and further defined boundary-wise by dashed lines 352.

At this point, the initiation of some additional steps which are used to further define the overall printhead structure are preferably implemented. The procedure currently being described and shown in the drawing figures is directed to the fabrication of a "buried" resistor system, with the accompanying drawings ultimately showing a representative resistor and associated interconnect components from a "length" standpoint. Regarding the "width" of the resistor 86, a number of steps can be taken at this time to define this parameter as needed and desired. While not specifically illustrated in the drawing figures for the sake of clarity, the primary and secondary layers 306, 334 of polycrystalline silicon may be suitably patterned/etched as needed and desired from a width standpoint using conventional processes including those discussed in Elliott, D. J., *Integrated Circuit Fabrication Technology,* McGraw-Hill Book Company, New York (1982) - (ISBN No. 0-07-019238-3), as noted above. Standard photoresist materials and techniques can be employed to suitably mask off various portions of the layers 306, 334 of polycrystalline silicon, followed by etching as needed and desired using, for example, gaseous materials containing chlorine and fluorine (e.g. SF$_6$ with small amounts of chlorine combined therewith) as chemical etchants for polycrystalline silicon. Nonetheless, it is again important to emphasize that this particular stage (namely, the photoimaging/etching steps that are used to define the width of the resistor element[s] in the completed printhead structure) involves conventional and standard procedures which are not considered to be part of this invention and are routine in nature.

Figure 16:
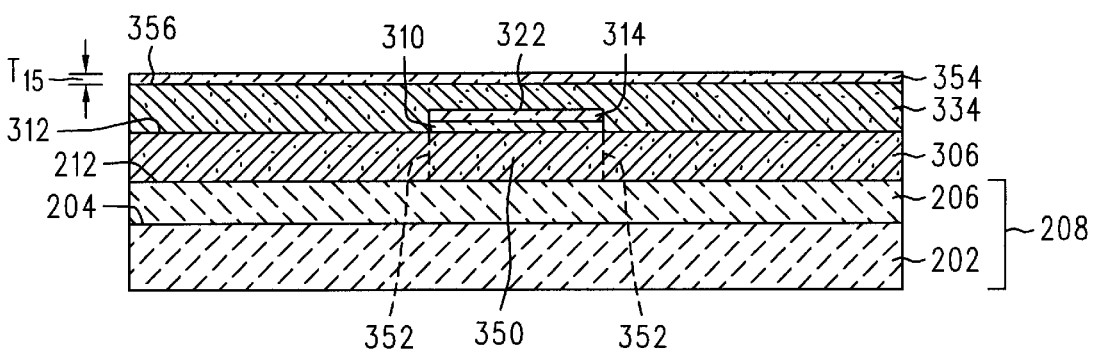

Referring back to the basic process and with reference to FIG. 16, the next step in the preferred fabrication procedure involves the placement of an additional layer 354 of silicon oxide material over the entire upper surface 356 of the secondary layer 334 of polycrystalline silicon. The term "silicon oxide material" or "silicon oxide" as used in connection with the layer 354 shall be construed and defined in the same manner recited above relative to layer 310. It should be noted that the upper surface 356 of the secondary layer 334 of polycrystalline silicon is highly planar and smooth in character based on the particular chemical nature of polycrystalline silicon, as well as the annealing process discussed above which greatly contributes to this beneficial feature of the invention (discussed further below). The additional layer 354 of silicon oxide material is optimally applied using the same techniques set forth above in connection with the initial/primary layer 310 of silicon oxide material, namely, conventional plasma-enhanced chemical vapor deposition (PECVD) of tetraethyl orthosilicate ("TEOS"). As a result, the additional layer 354 of silicon oxide material is produced at a preferred and non-limiting uniform thickness "$T_{15}$" of about 100–300 Å. This is substantially the same thickness as that associated with the primary layer 310 of silicon oxide material (see "$T_{11}$" in FIG. 8). From a functional standpoint, the additional layer 354 of silicon oxide material is again primarily designed to protect the chemical integrity of the underlying secondary layer 334 of polycrystalline silicon during later production stages as outlined below. It is likewise employed as an "etch stop" layer during subsequent silicon nitride dry etching. It should also be noted that all of the information provided above regarding the term "TEOS" as used in connection with the layer 310 of silicon oxide material is equally applicable to additional layer 354 of silicon oxide material. Likewise, the present invention shall not be limited to any particular methods for producing the additional layer 354 of silicon oxide material, with the "TEOS"-based process listed above being only one example.

Figure 17:
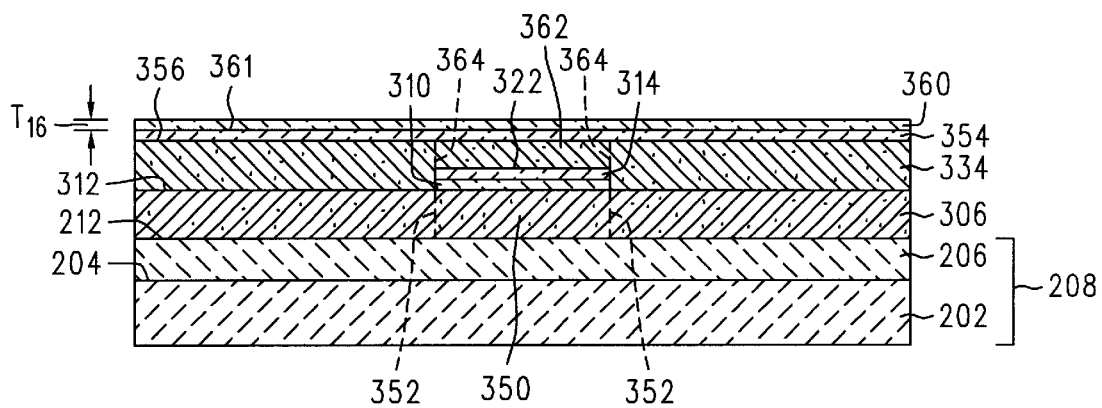

As illustrated in FIG. 17, the next step in the representative procedure being described in this section involves the application of an additional layer 360 of silicon nitride (Si$_3$N$_4$ or other stoichiometric variants of this formula) onto the entire upper surface 361 of the additional layer 354 of silicon oxide material. This step may be achieved using many different techniques including but not limited to those recited above in connection with the initial/primary layer 314 of silicon nitride, namely, conventional low pressure chemical vapor deposition (LPCVD) and/or plasma-enhanced chemical vapor deposition (PECVD) methods at a preferred and non-limiting uniform thickness "$T_{16}$" of about 100–300 Å. This is substantially the same thickness as that associated with the primary layer 314 of silicon nitride [see "$T_{12}$" in FIG. 9]). From a functional standpoint, the additional layer 360 of silicon nitride is employed in order to form a protective "mask" over (1) the particular section of the structure shown in FIG. 17 which will become the resistor 86, namely, portion 350 of the primary layer 306 of polycrystalline silicon; and (2) the particular section of the secondary layer 334 of polycrystalline silicon which is located above the remaining primary layers 310, 314 of silicon oxide material and silicon nitride. This "intermediate" section of the secondary layer 334 shall be designated hereinafter at reference number 362 and further defined boundary-wise by dashed lines 364.

Figure 18:
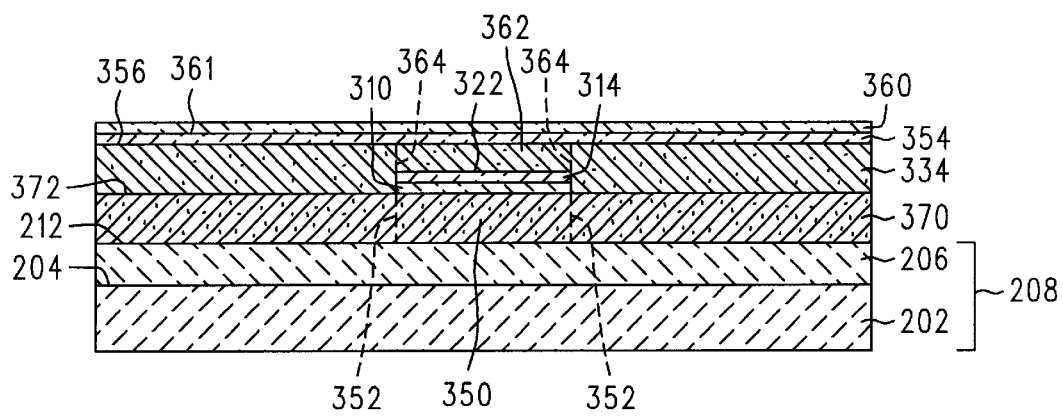

At this point, one of the two "doping" stages in the preferred embodiment of this invention is initiated. Specifically, the polycrystalline silicon in the layer 306 of FIG. 17 is doped in order to form a primary layer 370 of doped polycrystalline silicon (FIG. 18). Many different doping methods may be employed for this purpose without limitation. Likewise, a number of different doped polycrystalline silicon materials can be fabricated in connection with the primary layer 370 as previously discussed including phosphorous-doped polycrystalline silicon (preferred), boron-doped polycrystalline silicon, arsenic-doped polycrystalline silicon, antimony-doped polycrystalline silicon, and mixtures thereof. In particular, the final product associated with the primary layer 370 of doped polycrystalline silicon will depend on the dopant being employed, with representative and non-limiting dopants including phosphorous [P] (preferred), boron [B], arsenic [As], antimony [Sb], and mixtures thereof. However, for example purposes, the doping process will be described hereinafter with particular reference to phosphorous-doped polycrystalline silicon (the preferred material). Basically, doping (which is a well-known procedure) is accomplished by using a conventional ion-implantation apparatus that produces a supply of the desired ions from a selected source (e.g. phosphine if phosphorous ions are to be generated). In the present non-limiting embodiment, doping is achieved in a very specific manner so that only the "buried" primary layer 306 of polycrystalline silicon is substantially affected. In other words, it is important at this stage and in accordance with the current embodiment to provide a necessary adjustment of the appropriate doping parameters in order to effectively dope only the underlying primary layer 306 of polycrystalline silicon. This is typically accomplished by controlling the "implant penetration parameters" in this case, namely, (1) the energy level of the dopant ions being administered (of primary consequence); and (2) the "dose" of the ions as outlined further below. By selective adjustment of these parameters using the chosen implantation apparatus (which may again be conventional in nature), doping of the primary layer 306 of polycrystalline silicon will occur, with the secondary layer 334 of polycrystalline silicon remaining substantially undoped. For this purposes of this discussion, the term "substantially undoped" or "undoped" will involve a situation in which the polycrystalline silicon layer or section under consideration is at least about 95% dopant-ion free. During virtually all doping processes and in accordance with the inherent limitations of the scientific devices currently being used for these purposes, it is never possible to state that a given region or layer will remain totally "dopant ion-free" since small quantities of extraneous dopant ions can migrate or otherwise end up residing in various regions where they are not necessarily desired or intended. This situation again exists in accordance with the inherent process and equipment limitations mentioned above. However, by again selectively adjusting the implant penetration parameters described herein using routine preliminary testing and the like, various regions of the chosen component or structure (e.g. the primary layer 306 of polycrystalline silicon) can be selected to receive most or all of the desired dopant ions.

In the current non-limiting/representative embodiment (and with particular reference to the specific materials, layer thicknesses, and other values identified above), exemplary and preferred implant penetration parameters which may be used in connection with the delivery of phosphorous or the other dopant ions recited herein to the primary layer 306 of polycrystalline silicon will now be discussed. These parameters will optimally involve a dopant ion energy level of about 120–230 KeV using the selected ion-implantation apparatus, with an ion "dose" of about $1.0 \times 10^{15}$ to $3.0 \times 10^{15}$ dopant ions per $cm^2$. Ion implantation devices of conventional design may be employed in the doping processes of this invention, with such devices being used to extract ion species of interest from a source-gas or solid and thereafter accelerate the ions to the desired energy levels which are projected onto the workpiece of interest. A representative ion implantation system which employs, for example, an ion source, magnetic ion selection unit, an acceleration tube, focusing elements, traps/gates, and the like is illustrated and discussed in Elliott, D. J., *Integrated Circuit Fabrication Technology*, McGraw-Hill Book Company, New York (1982) - (ISBN No. 0-07-019238-3), p. 16 which is again incorporated herein by reference. As a result of this process, the implantation/doping procedure occurs in a "buried" fashion, namely, the ions of interest (phosphorous ions in this example) are implanted with sufficient energy to substantially by-pass the secondary (e.g. upper) layer 334 of polycrystalline silicon and instead enter the primary (e.g. lower) layer 306 of polycrystalline silicon including the portion 350 that will ultimately become the resistor 86. In particular, the primary layer 306 of polycrystalline silicon will be doped substantially along its entire length in a mostly uniform manner using the energy levels and other parameters expressed above in order to yield the primary layer 370 of doped polycrystalline silicon illustrated in FIG. 18. Again, the precise energy levels and other factors associated with doping at this stage (which is undertaken in a "buried" fashion) will be determined using routine preliminary pilot testing.

Regarding the production of other doped polycrystalline silicon materials which can be used in connection with the layer 370 as recited above, this may likewise be achieved using the methodology described herein. However, the dopant source, ion energy levels, and "doses" are changed as needed and desired in accordance with routine preliminary testing. As a result of the foregoing procedure, the desired implant material or "dopant" will be interspersed within the polycrystalline silicon structure of layer 370. A preferred and non-limiting "doping level" to be employed in this step which is applicable to all of the doped polycrystalline silicon materials used in layer 370 will involve about $10^{17}$–$10^{21}$ dopant atoms per $cm^3$. The term "doping level" is defined to encompass the number of dopant atoms which are present in the layer 370 per $cm^3$ (whether they involve phosphorous or other materials). Likewise, in accordance with the oxide-based character of the silicon oxide material which is present in the additional layer 354 and the remainder of the primary layer 310, doping may be accomplished in an effective manner directly through such layers without difficulty. A comparable situation exists regarding the additional layer 360 of silicon nitride and the remainder of the primary layer 314 thereof which will also permit dopant ions to pass therethrough in accordance with the particular chemical nature of these layers and the doping energy levels recited above.

It shall again be understood that the various doping step(s) outlined in this section can be accomplished in many different ways including the use of techniques generally discussed in Elliott, D. J., *Integrated Circuit Fabrication*

*Technology,* McGraw-Hill Book Company, New York (1982)-(ISBN No. 0-07-019238-3), pp. 13–18 (incorporated herein by reference). At this point, the ultimate goal of the foregoing procedure is to ideally achieve a resistivity associated with the primary layer 370 of doped polycrystalline silicon of about 2000–4000 $\mu\Omega$-cm with a "TCR" ("temperature coefficient of resistance") that is positive and as low as possible (e.g. close to zero), with a range of about 25–100 ppm/° C. providing effective results. However, the foregoing values are subject to change and/or modification as needed and desired in accordance with the particular printhead design under consideration. The "temperature coefficient of resistance" of a substance is generally defined to involve the change in resistivity of the substance per unit change in temperature. Low (e.g. near-zero, but positive) "TCR" values are desirable in the present invention with particular reference to the primary layer 370 of doped polycrystalline silicon because such values prevent "current crowding" (defined above) which, if not controlled, may reduce resistor reliability. Also, low-positive "TCR" values are important to ensure that energy can be delivered efficiently to the resistor(s) during printhead operation. Incidentally, the upper surface of the primary layer 370 of doped polycrystalline silicon is shown at number 372 in FIG. 18 and hereinafter for reference purposes. It should also be noted that, while doping of the primary layer 306 of polycrystalline silicon is preferred as previously discussed, it is likewise possible for the layer 306 to remain undoped (defined above) depending on a number of considerations including the desired resistivity of the final product (which will decrease as doping occurs) and other related factors. Thus, the present invention shall not be completely restricted to a situation in which the primary layer 306 of polycrystalline silicon is doped, with an undoped layer 306 also being possible. It should likewise be understood that, in a preferred and non-limiting embodiment, at least one of the primary and secondary layers 306, 334 of polycrystalline silicon should be doped and, if primary layer 306 is not doped, at least part of the secondary layer 334 should be doped and vice versa. However, under certain circumstances and in a still further alternative embodiment, both of the primary and secondary layers 306, 334 of polycrystalline silicon can remain undoped. Nonetheless, as will become readily apparent from the discussion provided below, excellent results are achieved if both layers 306, 334 are doped which shall be considered the optimum embodiment in this case.

The present invention shall also not be restricted to any order in which the doping of various layers occurs (with particular reference to the doping of primary layer 306 of polycrystalline silicon). While the "buried" doping/implant method discussed above is preferred, the doping of primary layer 306 of polycrystalline silicon could actually occur earlier in the production process. For example, the layer 306 could be doped after it was initially applied in position and annealed as discussed above and shown in FIG. 7. However, the "buried" doping technique described herein is preferred in that it serves to produce the smoothest overall surfaces and planar topography relative to the layer 306 and additional layers thereover. This consideration is important for numerous reasons as discussed in greater detail below (including the reduction and control of surface defects that can shorten overall printhead life).

Figure 19:
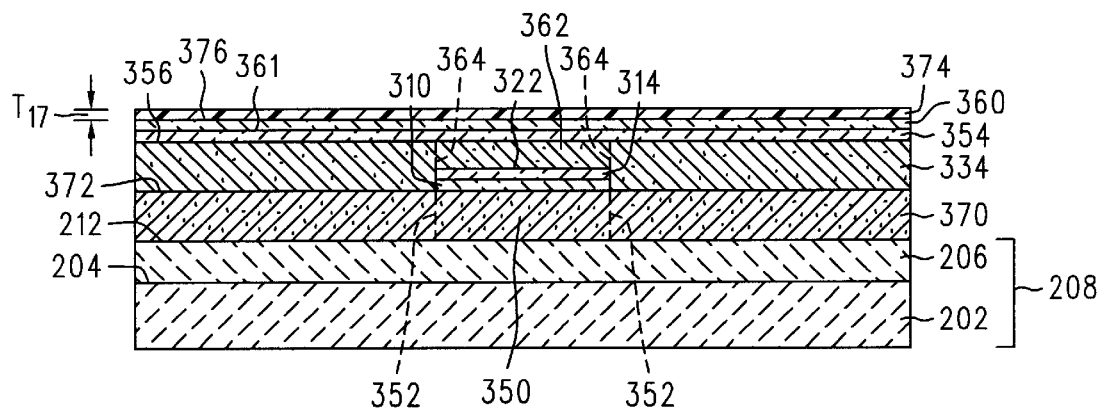

With reference to FIG. 19, the next step in the preferred and non-limiting process of the present invention involves the application of another layer 374 of standard positive photoresist material to the upper surface 376 of the additional layer 360 of silicon nitride along its entire length. In a representative and exemplary embodiment, the layer 374 of photoresist material will again consist of a commercial product sold under the designation "HPR504" produced by the Olin Chemical Corp. of Norwalk, Conn. (USA) which is applied at a preferred and non-limiting uniform thickness "$T_{17}$" of about 1–2 $\mu$m. This is the same material that was listed above in connection with the layer 320 of photoresist material that was illustrated in FIG. 10. Likewise, the thickness "$T_{17}$" is substantially the same as that associated with the initial layer 320 of photoresist (see "$T_{13}$" in FIG. 10). However, the claimed invention shall not be restricted to any particular photoresist materials or types (e.g. positive or negative), with a number of different compositions being suitable for use.

Figure 20:
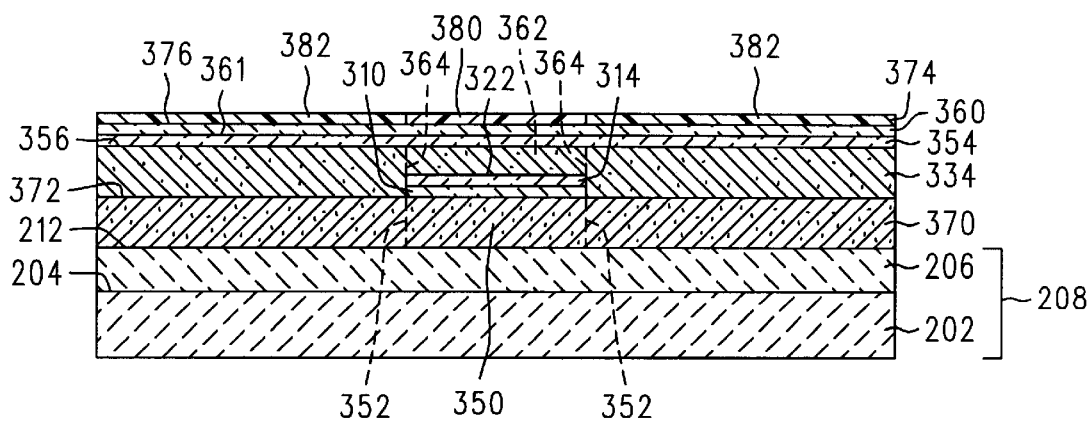

Using standard masking processes that are again well known in the art, the layer 374 of photoresist material is then imaged in a conventional fashion as discussed, for example, in the *Integrated Circuit Fabrication Technology* reference cited above. This step (as illustrated in FIG. 20) yields an unexposed region 380 of the layer 374. The unexposed region 380 is located directly over intermediate section 362 of the secondary layer of polycrystalline silicon 334 and portion 350 of the primary layer 370 of doped polycrystalline silicon [formerly the primary layer 306 of undoped polycrystalline silicon]). Also generated are exposed regions 382 of photoresist material on both sides of the unexposed region 380. As noted above, the portion 350 illustrated in FIG. 20 will ultimately become the resistor 86 in the completed printhead structure. Thereafter, the exposed regions 382 of the layer 374 of photoresist material are etched away or otherwise removed to yield the structure of FIG. 21. In this structure, various sections of the upper surface 376 of the additional layer 360 of silicon nitride are exposed as shown. While a number of different chemical removal techniques can be employed for this purpose, a preferred procedure involves removing the exposed regions 382 of the photoresist-containing layer 374 by spraying or immersing the structure of FIG. 20 in a conventional resist developer (e.g., a commercial material known as "HPRD429" which is produced by the Olin Chemical Corp. of Norwalk, Conn. [USA]), followed by rinsing in deionized water. The unexposed region 380 remains in place as shown for the reasons given below.

At this point in the preferred and non-limiting fabrication process currently being discussed, a second doping stage is implemented. It is important to emphasize that the second doping stage is optional in nature and may be omitted from the foregoing process if needed and desired as determined using routine preliminary pilot testing. In particular, this doping step (which concerns the secondary layer 334 of polycrystalline silicon) may be omitted if the primary layer 306 is doped as outlined above. However, doping at this stage is preferred in order to fabricate low-resistance, highly-efficient resistor interconnect structures from the secondary layer 334 as discussed later in this section.

Figure 21:
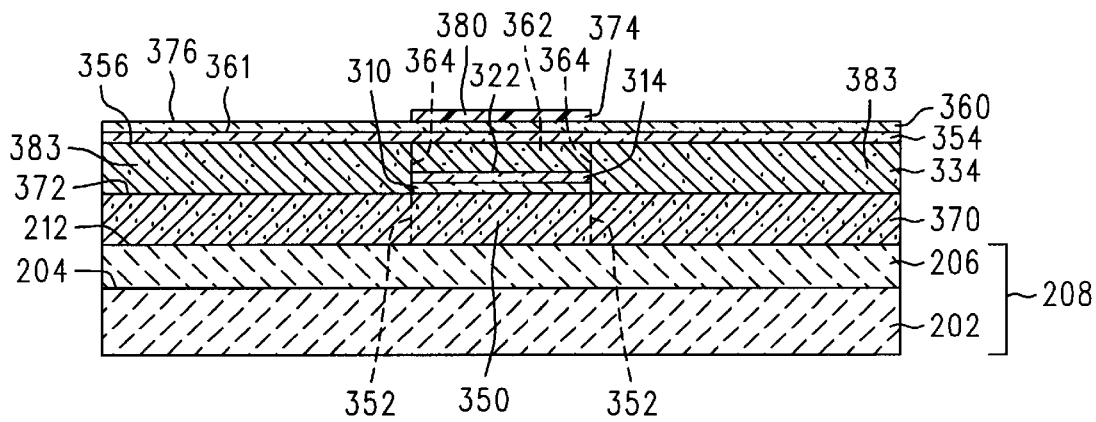

To accomplish doping of the secondary layer 334 of polycrystalline silicon, many different methods may be employed for this purpose without limitation. Likewise, a number of different doped polycrystalline silicon materials can be generated from the secondary layer 334 including but not limited to phosphorous-doped polycrystalline silicon (preferred), boron-doped polycrystalline silicon, arsenic-doped polycrystalline silicon, antimony-doped polycrystalline silicon, and mixtures thereof. In this regard, representative and non-limiting dopants which can be employed at this stage include phosphorous [P] (preferred), boron [B], arsenic [As], antimony [Sb], and mixtures thereof. However, for example purposes, the doping process will be described herein with particular reference to phosphorous-doped polycrystalline silicon (the optimum material). It should also be noted that the dopants selected for use in connection with the secondary layer 334 of polycrystalline silicon do not necessarily have to be the same as those used to produce the primary layer 370 of doped polycrystalline silicon, although the use of common dopants for both structures is preferred. Doping of the secondary layer 334 of polycrystalline silicon is accomplished in a standard fashion using a conventional ion-implantation apparatus of the same type discussed above in connection with the initial doping stage. This procedure produces a supply of the desired ions from a selected source (e.g. phosphine if phosphorous ions are to be generated). Other ion sources will be used for different dopant materials. In the present embodiment, doping is optimally undertaken so that only those portions/sections 383 of the secondary layer 334 of polycrystalline silicon that surround the intermediate section 362 as illustrated in FIG. 21 are affected (e.g. doped). Basically, this is achieved through the blocking action of the unexposed region 380 of photoresist material derived from layer 374 which remains in position as illustrated in FIG. 21. The presence of the unexposed region 380 (and its particular chemical character) substantially prevents ion implantation (e.g. doping) of the materials/regions thereunder, namely, the intermediate section 362 of the layer 334. Likewise, the doping parameters employed at this stage are appropriately and preferably adjusted in order to effectively dope only the desired regions of secondary layer 334 of polycrystalline silicon without going any deeper into, for example, the primary layer 370 of doped polycrystalline silicon. This is typically accomplished by controlling the above-listed "implant penetration parameters" in this case, namely, (1) the energy level of the ions being administered (which is of primary concern); and (2) the "dose" of the ions. By appropriately adjusting these factors using the chosen implantation apparatus (which is conventional in nature and discussed generally above), selective doping of the secondary layer 334 will occur. However, it shall be understood that some additional, inconsequential doping of the primary layer 370 of doped polycrystalline silicon may also take place. Such additional doping can occur in accordance with the inherent limitations and unpredictability of the doping process and equipment that are normally used for this purpose. Nonetheless, any further doping of the primary layer 370 of doped polycrystalline silicon will again be of minimal consequence assuming that the appropriate guidelines as expressed herein are followed to a substantial degree or routinely adjusted as needed to ensure site-specific doping into the secondary layer 334.

It should be noted that, if desired in accordance with routine preliminary pilot testing, the "implant penetration parameters" discussed above could be suitably adjusted to also provide further doping of the primary layer 370 of doped polycrystalline silicon (along with doping of the secondary layer 334 of polycrystalline silicon). This may be done to additionally reduce the resistance of the resistor interconnect structures in the final product if needed. Nonetheless, the remaining description of the claimed invention will focus on selective doping of the secondary layer 334 of polycrystalline silicon at this stage without substantial additional doping of the primary layer 370 of doped polycrystalline silicon which shall be considered a preferred embodiment.

Figure 22:
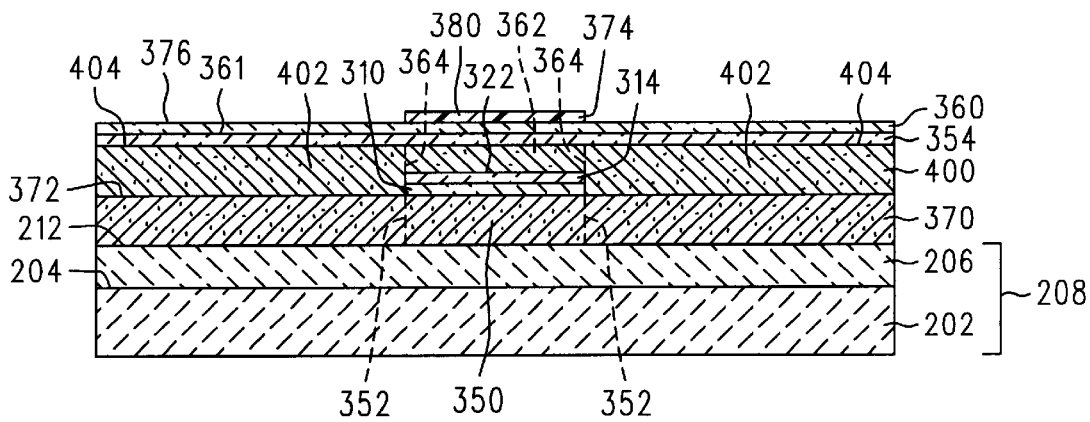

In the current non-limiting/representative embodiment (and with particular reference to the specific materials, layer thicknesses, and other values identified above), exemplary and preferred implant penetration parameters which may be used in connection with the delivery of phosphorous or the other dopant ions recited herein to the secondary layer 334 of polycrystalline silicon will now be discussed. These parameters will optimally involve a dopant ion energy level of about 30–70 KeV using the selected ion-implantation apparatus (discussed above), with an ion "dose" of about $1\times10^{15}$ to $3\times10^{15}$ ions per $cm^2$. As a result of this process, the site-specific ion implantation/doping procedure will occur in the manner discussed above. Specifically, the secondary layer 334 of polycrystalline silicon will be effectively converted to a secondary layer 400 of doped polycrystalline silicon (FIG. 22). It should, however, be understood that the intermediate section 362 will remain substantially undoped (defined above) based on the implantation penetration parameters which are used at this stage, as well as the blocking action of the unexposed region 380 of photoresist material discussed above. On each side of the intermediate section 362, dual sections 402 of doped polycrystalline silicon (FIG. 22) derived from portions/sections 383 will be present as a result of the foregoing procedure. The upper surface of each section 402 will be identified hereinafter using reference number 404 (which replaces reference number 356 that was associated with the layer 334 of undoped polycrystalline silicon). Thus, in summary, the secondary layer 400 of doped polycrystalline silicon will consist primarily of the doped sections 402 separated by the intermediate section 362 which is substantially undoped (and therefore has a much greater resistance than the sections 402). For the purposes of this discussion, the secondary layer 400 shall continue to be designated as containing doped polycrystalline silicon even though it also includes the substantially undoped section 362 therein which only occupies a very small, minority part of the overall secondary layer 400.

Regarding the production of other doped polycrystalline silicon materials which may be employed in connection with the layer 400 as listed in the present section, this may likewise be accomplished using the methodology described above except that the dopant source, ion energy levels, and "doses" are changed as needed and desired in accordance with routine preliminary testing. As a result of the doping procedure outlined above, the desired "implant" material or "dopant" will be interspersed within the polycrystalline silicon structure of layer 400 (with particular reference to the sections 402 and substantially excluding intermediate section 362). A preferred and non-limiting "doping level" to be employed in this step which is applicable to the sections 402 used in the secondary layer 400 will involve about $10^{18}$–$10^{21}$ dopant atoms per $cm^3$. The term "doping level" is again defined to encompass the number of dopant atoms which are present in the sections 402 of layer 400 per $cm^3$ thereof (whether they involve phosphorous or other materials). Likewise, in view of the oxide-based character of the silicon oxide material recited above which is present in the additional layer 354 thereof, doping may be accomplished in an effective manner directly through this layer without difficulty. A comparable situation exists regarding the additional layer 360 of silicon nitride which will also permit dopant ions to pass therethrough in accordance with the particular chemical nature of this layer and the doping energy levels recited above. It shall again be emphasized that the doping step(s) outlined in this section can be accomplished in many different ways including the use of techniques generally discussed in Elliott, D. J., *Integrated Circuit Fabrication Technology,* McGraw-Hill Book Company, New York (1982) - (ISBN No. 0-07-019238-3), pp. 13–18 (incorporated herein by reference).

Figure 23:
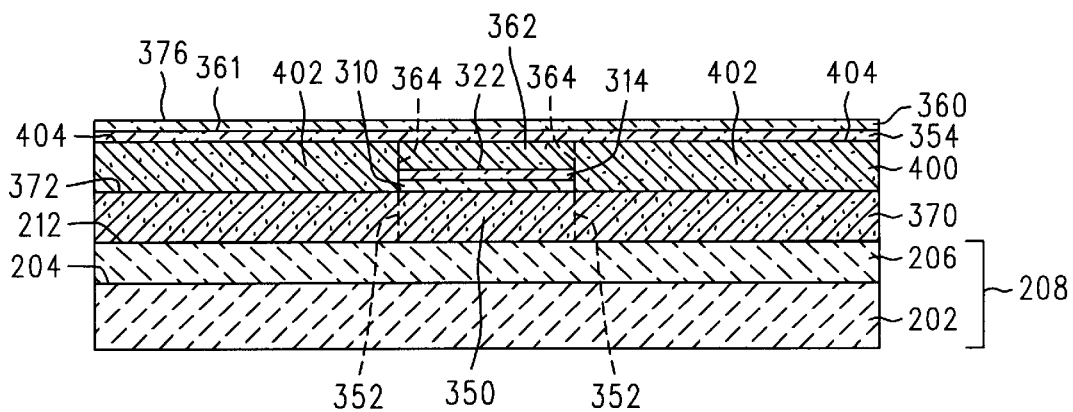

Next, with reference to FIGS. 22–23, the unexposed region 380 of the layer 374 of photoresist material is removed. This may be accomplished in many different ways without limitation. However, in a preferred embodiment, the unexposed region 380 is eliminated using a two-step process first involving "dry etching" the structure of FIG. 22 in an oxygen plasma and then treating the structure using a "wet cleaning" stage employing, for example, sulfuric peroxide or other comparable materials known in the art for this purpose.

Figure 24:
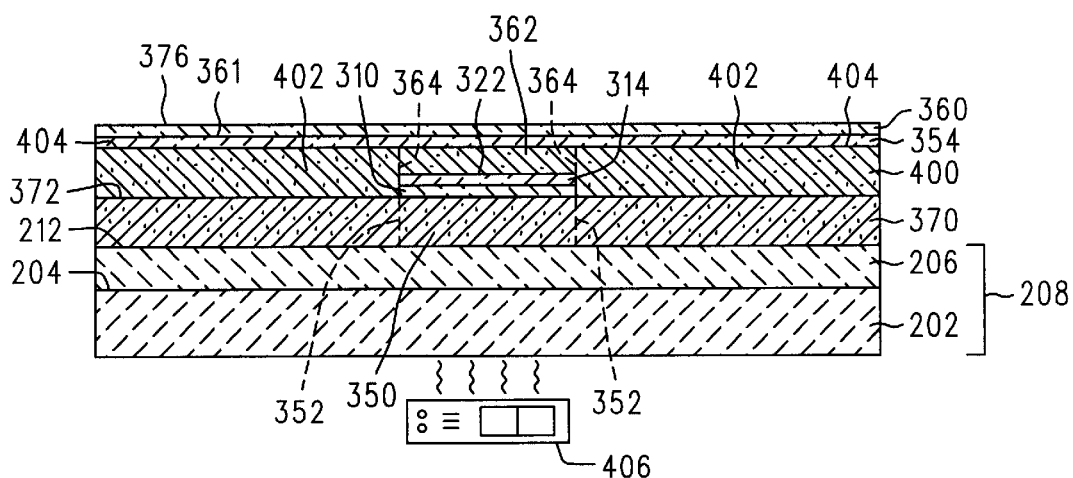

The primary and secondary layers of doped polycrystalline silicon 370, 400 (with particular reference to sections 402) are thereafter "activated" as schematically illustrated in FIG. 24. This step is undertaken in order to properly place the selected "dopant" atoms (e.g. phosphorous [P] ions or whatever other dopant is employed) in the proper crystal-lattice positions within the doped polycrystalline silicon layers 370, 400 (to "replace" silicon [Si] atoms at the appropriate locations). In this manner, a resistor 86 having the desired functional capabilities can be fabricated from the portion 350 of the primary layer 370 of doped polycrystalline silicon. Likewise, suitable resistor interconnect structures can be made from the sections 402 of the secondary layer 400 of doped polycrystalline silicon. Activation of the layers 370, 400 is optimally achieved in a representative and non-limiting embodiment by using a standard rapid thermal anneal apparatus 406 illustrated schematically in FIG. 24 (or other known heating systems/techniques including laser heating, a conventional furnace, and the like). In this manner, the entire structure of FIG. 24 (including the layers 370, 400 of doped polycrystalline silicon) may be uniformly heated to a preferred temperature of about 900–1000° C. over a time period of about 15–30 seconds. However, these parameters may again be varied as needed in accordance with routine preliminary testing taking into account a number of factors including but not limited to the type of construction materials being used and the like.

Figure 25:
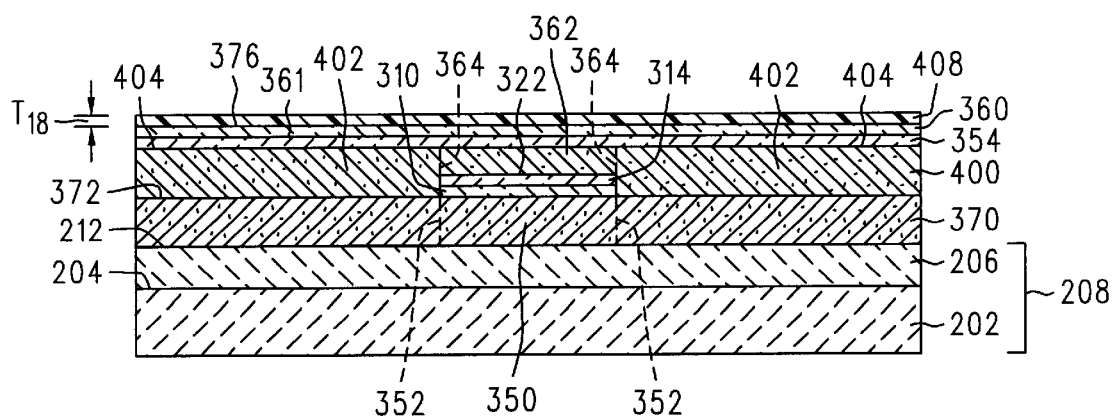

Referring now to FIG. 25, the next step in the preferred and non-limiting process being described this section involves the application of a still further layer 408 of standard positive photoresist material to the entire upper surface 376 of the additional layer 360 of silicon nitride. In a representative, exemplary embodiment, the layer 408 of photoresist material will again consist of a commercial product sold under the designation "HPR504" produced by the Olin Chemical Corp. of Norwalk, Conn. (USA) which is applied at a preferred and non-limiting uniform thickness "$T_{18}$" of about 1–2 μm. This is the same material that was listed above in connection with the layer 320 of photoresist material illustrated in FIG. 10. Likewise, the thickness "$T_{18}$" is substantially the same as that associated with the initial layer 320 of photoresist (see "$T_{13}$" in FIG. 10). However, it should again be noted that the claimed invention shall not be restricted to any particular photoresist materials or types (e.g. positive or negative), with a number of different compositions being suitable for use.

Figure 26:
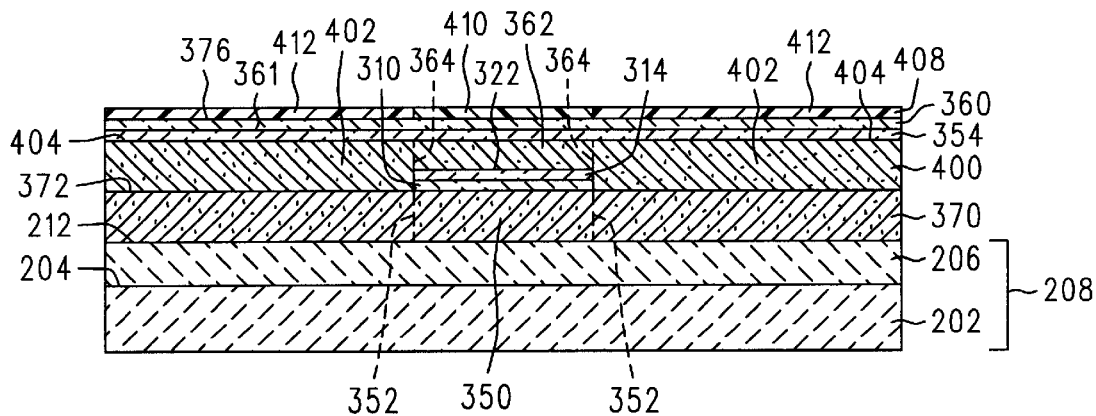

Using standard masking processes that are again well known in the art, the layer 408 of photoresist material is then imaged in a conventional fashion as discussed, for example, in the *Integrated Circuit Fabrication Technology* reference cited above. This step (as illustrated schematically in FIG. 26) yields an unexposed region 410 which is located over undoped section 362 of the secondary layer 400. Also produced are exposed regions 412 on both sides of the unexposed region 410. The exposed regions 412 in the embodiment of FIG. 26 are located over the doped sections 402 of the secondary layer 400 of doped polycrystalline silicon. Thereafter, the exposed regions 412 of the layer 408 of photoresist material are etched away to yield the structure of FIG. 27. As a result, various sections/regions of the upper surface 376 of the additional layer 360 of silicon nitride are again exposed as shown. While a number of different chemical removal techniques can be employed for this purpose, a preferred procedure involves eliminating the exposed regions 412 of the photoresist-containing layer 408 by spraying or immersing the structure of FIG. 26 in a conventional resist developer (e.g., a commercial material known as "HPRD429" which is produced by the Olin Chemical Corp. of Norwalk, Conn. [USA]), followed by rinsing in deionized water. The unexposed region 410 of the photoresist-containing layer 408 remains in place as shown in order to effectively complete the remainder of the production process as discussed below.

Figure 27:
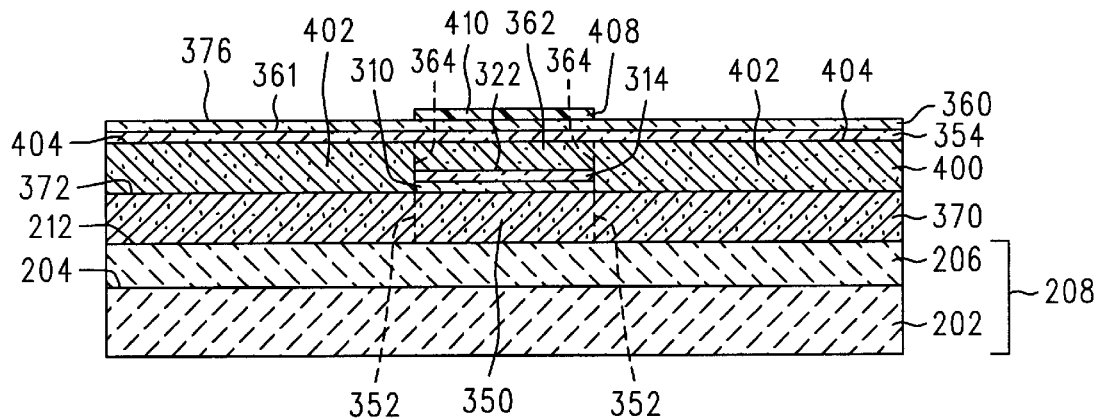
Figure 28:
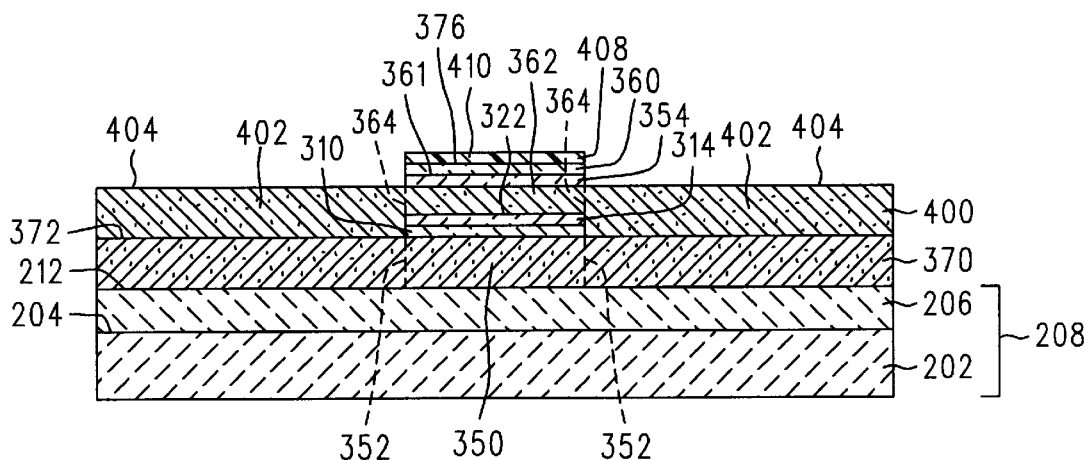

Thereafter, the particular sections of the additional layers 354, 360 of silicon oxide material and silicon nitride which were revealed after the photoresist stripping step of FIG. 27 are etched away to yield the structure of FIG. 28. While a number of different etching techniques can be employed for this purpose, a preferred procedure first involves removing the additional layer 360 of silicon nitride by the conventional "dry etching" thereof in a fluorine or chlorine gaseous plasma. Next, the layer 354 of silicon oxide material may be conventionally removed by chemical etching in a hydrofluoric acid (HF) solution. Again, the foregoing process is provided for example purposes only and shall be considered non-limiting. As shown in FIG. 28, the steps described above result in an overall structure wherein the upper surface 404 of the secondary layer 400 of doped polycrystalline silicon at sections 402 is "exposed" (revealed). The undoped polycrystalline silicon-containing intermediate section 362 of the secondary layer 400 remains covered by (1) the unexposed region 410 of the photoresist-containing layer 408; (2) the remainder of the additional layer 360 of silicon nitride; and (3) the remainder of the additional layer 354 of silicon oxide material.

Figure 29:
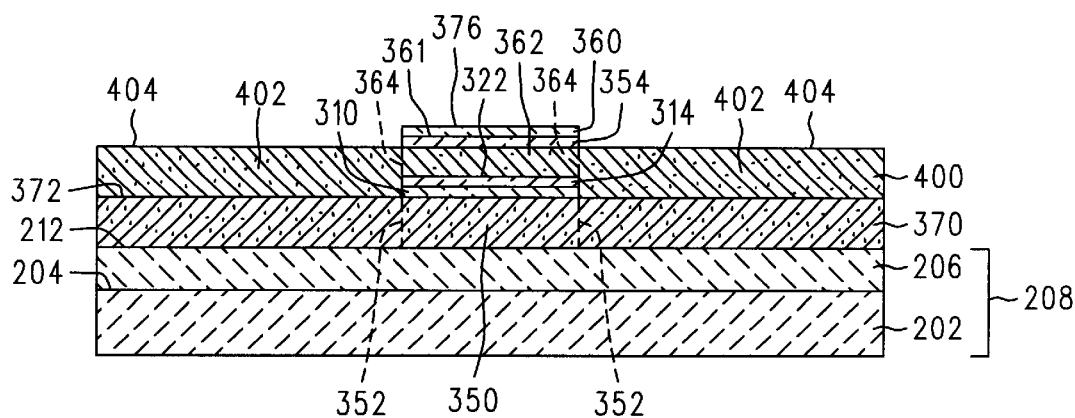

Next, in accordance with FIG. 29, the remaining unexposed region 410 of the photoresist-containing layer 408 is preferably removed using (in a non-limiting embodiment) a two-step process first involving "dry etching" the structure of FIG. 28 in an oxygen plasma and then treating the structure using a "wet cleaning" stage employing, for example, sulfuric peroxide or other comparable materials known in the art for this purpose. Thereafter, and with particular reference to FIG. 30, a layer 414 of at least one elemental metal is applied to the entire upper surface of the structure shown in FIG. 29. Specifically, the layer 414 is delivered to (A) the exposed upper surface 404 of the sections 402 associated with the secondary layer 400 of doped polycrystalline silicon; and (B) the upper surface 376 of the additional layer 360 of silicon nitride.

While the claimed invention shall not be restricted to any particular metal compositions (or mixtures thereof) in connection with the layer 414, the following elemental metals may be used: titanium [Ti] (preferred), cobalt [Co], tungsten [W], platinum [Pt], molybdenum [Mo], tantalum [Ta], palladium [Pd], and mixtures thereof. The selection of any given metal (or combinations of metals) for use in the layer 414 will, in part, involve an assessment of the particular doped polycrystalline silicon material that is chosen for use in the underlying secondary layer 400 in the present embodiment. It should also be noted that the same metals recited above in connection with layer 414 could be employed even if the previously-discussed secondary layer 334 of polycrystalline silicon was not doped (although doping is again preferred for the reasons given herein).

Figure 30:
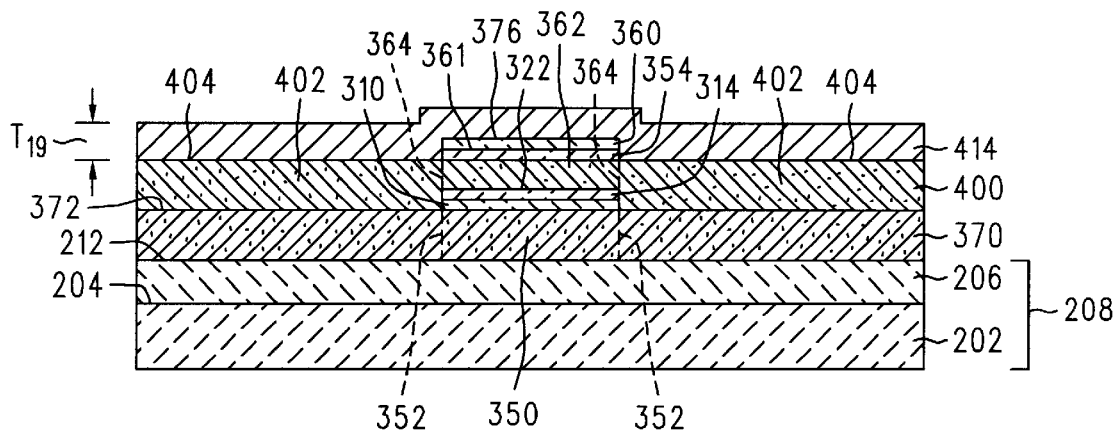

A number of different metals/polycrystalline silicon combinations are possible without limitation at this stage of the claimed process. Conventional deposition methods may be employed in order to deliver the metal-containing layer 414 in position including but not limited to known sputtering techniques, electron beam evaporation, plasma vapor deposition (PVD), or other comparable procedures. As illustrated in FIG. 30, the layer 414 is applied at a preferred and non-limiting uniform thickness "$T_{19}$" of about 300–1000 Å. Thereafter, the structure shown in FIG. 30 is heated (e.g. annealed) in a conventional fashion using a standard rapid thermal annealing apparatus 416 (FIG. 31) or other comparable device (including a traditional furnace) to a preferred, non-limiting temperature of about 550–700° C. for about 20–40 seconds. This process initiates a chemical reaction in which the metal employed in the layer 414 reacts with the sections 402 of the secondary layer 400 of doped polycrystalline silicon to yield a layer 420 of metal silicide illustrated schematically in FIG. 31. Likewise, the foregoing reaction will typically (but not necessarily) encroach to a certain extent into the primary layer 370 of doped polycrystalline silicon. This encroachment is schematically illustrated in the drawing figures. The degree of encroachment (or whether encroachment will occur at all) will depend on numerous factors determined in accordance with preliminary pilot testing including the type of metal employed in connection with the layer 414, reaction conditions, and the like. In this regard, the claimed invention shall not be limited to a situation in which encroachment occurs or to any particular levels of encroachment.

Figure 31:
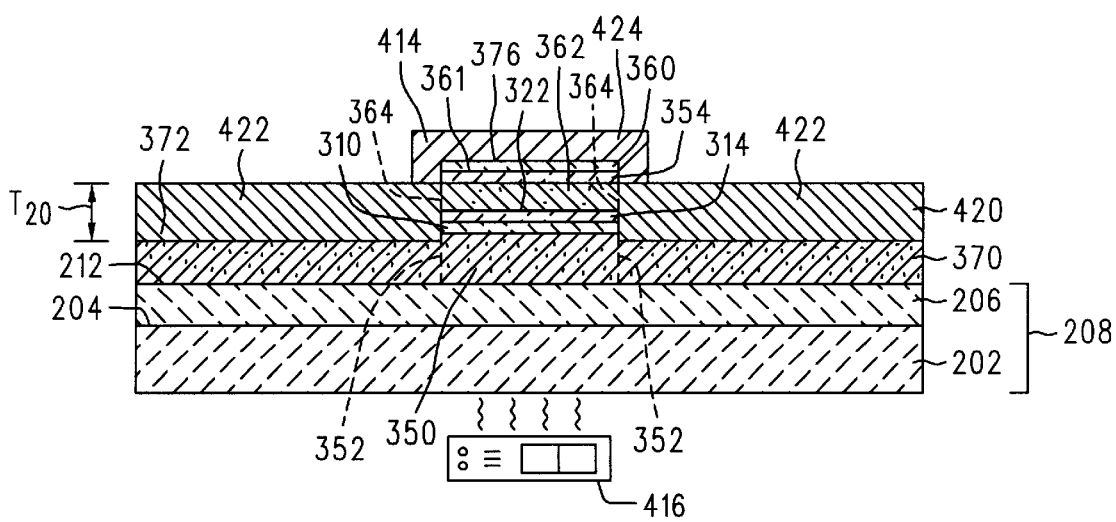

The layer 420 shall also be characterized herein as a "secondary" layer of material since it was primarily derived from the secondary layer 400 of doped polycrystalline silicon. The secondary layer 420 basically consists of (1) dual sections 422 of the desired metal silicide compound; and (2) the intermediate section 362 of undoped polycrystalline silicon which remains unaffected by the foregoing process. Regarding metal suicides which are produced in accordance with the above-listed procedure, titanium silicide [$TiSi_2$] will be generated when titanium [Ti] is employed in the layer 414 of FIG. 30. However, the specific metal silicide to be generated in the foregoing steps will depend on the particular metal(s) that are used to initially produce the layer 414. It is important to emphasize that the above-described "silicidation" reaction does not take place where the layer 414 of metal resides on or is otherwise in contact with the additional layers 354, 360 of silicon oxide material and silicon nitride as illustrated in FIG. 31. Thus, reference number 424 in FIG. 31 shall be used to refer to the particular portion of the previously-applied metal-containing layer 414 which remains unreacted. Likewise, for the purposes of this discussion, the layer 420 shall be designated as containing metal silicide compounds therein even though it also includes the substantially undoped intermediate section 362 of polycrystalline silicon which only occupies a very small, minority part of the overall layer 420.

The procedure described above effectively generates the layer 420 of metal silicide (with specific reference to sections 422) which, as previously stated, may involve many different silicide compounds depending on the composition (s) selected for use in the metal-containing layer 414. For example, taking into account the representative metals listed above in connection with layer 414, the metal silicide compound in layer 420/sections 422 could involve the following compositions: titanium silicide ($TiSi_2$) when titanium metal is used in layer 414, cobalt silicide ($CoSi_2$) when cobalt metal is employed in layer 414, tungsten silicide ($WSi_2$) when tungsten metal is present in layer 414, platinum silicide (PtSi) when the layer 414 is made from platinum, molybdenum silicide ($MoSi_2$) when the layer 414 is made from molybdenum, tantalum silicide ($TaSi_2$) when tantalum is employed within the layer 414, palladium silicide ($Pd_2Si$) when the layer 414 is produced from palladium, and mixtures thereof. Thus, the particular metal silicide to be generated in the foregoing process depends on numerous factors including but not limited to the types of materials that are used to produce the metal-containing layer 414.

As shown in FIG. 31 (which shall again be considered a schematic representation not necessarily drawn to scale), the layer 420 of metal silicide (including sections 422) is of greater thickness than the layer 414 of metal in accordance with the reaction discussed above. Specifically, metal atoms in layer 414 diffuse inwardly into the primary and secondary layers 370, 400 of doped polycrystalline silicon in a preferred and non-restrictive embodiment and thereafter chemically react with silicon to generate the metal silicide layer 420. The layer 420/sections 422 will have a representative and non-limiting thickness "$T_{20}$" about 400–2000 Å (depending on the relative thickness of the layer 414 and subject to change as needed and desired). It should be noted that FIG. 31 represents a typical embodiment of the invention which may be modified while still remaining within the scope thereof. For example, it is also possible that the layer 420 of metal silicide may be of lesser thickness than the layer 414 of metal, depending on the particular metal which is used and the desired overall thickness of the layer 420 which can be assessed in accordance with routine preliminary pilot testing.

Figure 32:
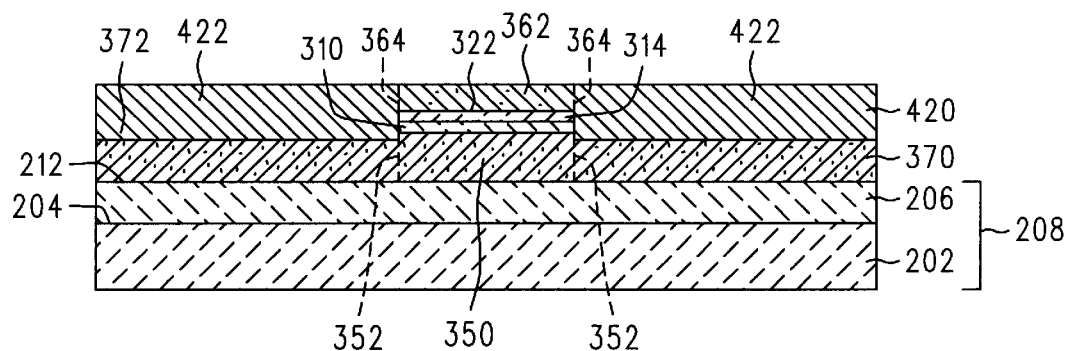

Next, with reference to FIGS. 31–32, the remaining unreacted portion 424 of the layer 414 of metal (which is present on the upper surface 376 of the additional layer 360 of silicon nitride) is stripped using, for example, a 5:1:1 stripping solution of dionized water: hydrogen peroxide [$H_2O_2$]: ammonium hydroxide [$NH_4OH$]. The additional layers 354, 360 of silicon oxide material and silicon nitride which remain in position on the intermediate section 362 of undoped polycrystalline silicon are also removed at this time. Removal of layers 354, 360 to yield the structure of FIG. 32 is accomplished by first eliminating the additional layer 360 of silicon nitride by the conventional "dry etching" thereof in a fluorine or chlorine gaseous plasma. Thereafter, the additional layer 354 of silicon oxide material may be conventionally eliminated by chemical etching in a hydrofluoric acid (HF) solution. Again, the foregoing procedure is provided for example purposes only and shall be considered non-limiting. It should likewise be noted that the additional layers 354, 360 may also be permitted to remain in place (in view of their relatively small size/thickness) if desired for protective purposes as determined in accordance with routine preliminary testing.

Figure 33:
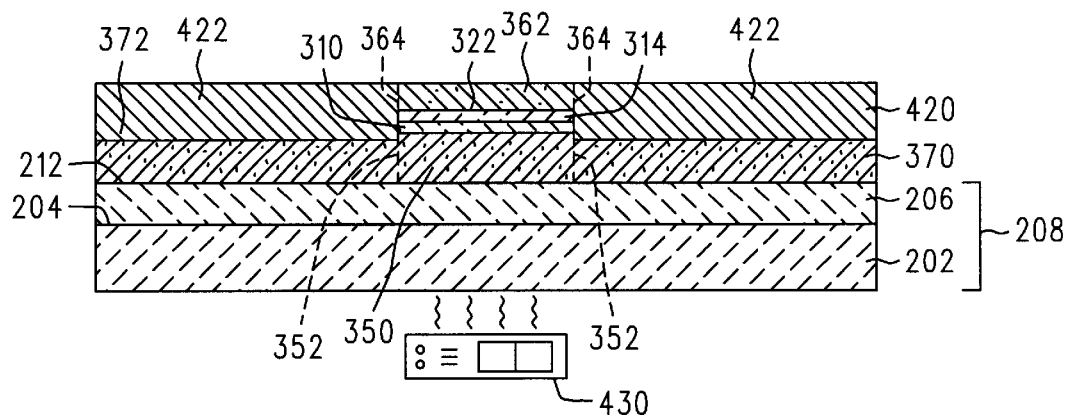

Next, in a preferred embodiment, the structure of FIG. 32 is optionally subjected to an additional annealing process using, for example, a standard rapid thermal annealing apparatus 430 or other comparable device (including a traditional furnace) as illustrated schematically in FIG. 33. This step is implemented in order to stimulate a further phase transformation involving the above-described silicide materials to ensure the lowest possible resistance in the metal silicide-containing sections 422 of the layer 420. In a representative and non-limiting embodiment, the structure of FIG. 32 is heated to a preferred temperature of about 800–900° C. for a time period of about 15–30 seconds. Thereafter, a still further optional annealing stage (not shown) may be implemented if needed and desired based on routine preliminary testing. This additional annealing stage (typically called a "forming gas anneal") preferably occurs in a nitrogen [$N_2$]/hydrogen [$H_2$] atmosphere at about 400–500° C. for about 15 minutes 1 hour using the same type of annealing system associated with apparatus 430. This extra annealing stage (which is employed in addition to the annealing step of FIG. 33 if desired) is designed to chemically "tie-up" incompletely bonded silicon atoms at grain boundaries (also known as "dangling bonds").

At this stage, formation of the resistor 86 is substantially completed, with the outer boundaries of the resistor 86 (namely, the portion 350 of the primary layer 370 of doped polycrystalline silicon) again being shown at dashed lines 352 in FIG. 34. The metal silicide-containing sections 422 of the layer 420 are in operative and electrical connection/communication with the resistor 86 as illustrated with particular reference to contact faces/surfaces "A" and "B" in FIG. 34 along the sides of the resistor 86. In this manner, electrical signals, impulses, and the like from one or more drive transistors and/or external signal sources (not shown) can be delivered to the resistor 86 via the metal silicide-containing sections 422 of the layer 420. Furthermore, the intermediate section 362 of undoped polycrystalline silicon functions as a higher-resistance barrier to the direct flow of electrical energy between the sections 422, thereby ensuring that such energy effectively passes through the resistor 86 in order to heat the ink materials (e.g. ink composition 32) which reside thereover.

In summary, the process outlined above enables at least one portion or section of a doped polycrystalline silicon-containing layer (primary layer 370 in the current embodiment) to be "formed" or "converted" into the resistor 86 in a novel "in situ" process (which constitutes a non-limiting, preferred embodiment of the invention). The resistor is then "buried" beneath another layer of material (preferably doped polycrystalline silicon as per secondary layer 400), with at least one section thereof being converted "in situ" into a conductive interconnect portion (with particular reference to metal silicide-containing sections 422). In the current embodiment, the sections 422 are again separated by the higher-resistance intermediate section 362 made from substantially undoped polycrystalline silicon which contributes to the overall effectiveness of the completed system 300. Specifically, with reference to FIG. 34, the undoped polycrystalline silicon-containing intermediate section 362 is at least partially aligned over and above the resistor 86 in order to contain and protect the resistor 86 within the printhead 80, 196, or other comparable structure.

In the novel and unique assembly of FIG. 34, the metal silicide-containing sections 422 of the layer 420 are positioned above and on both sides of the resistor 86. The sections 422 are operatively and electrically connected to the resistor 86 as previously defined. However, it is likewise possible to employ an alternative system in which a metal silicide-containing section 422 (through selective modification of the foregoing process steps) is located on only one side of the resistor 86 (either to the left or right of the resistor 86) if needed and desired. The remainder of the layer 420 would then be comprised of, for example, doped or undoped polycrystalline silicon (or other comparable material[s]). While the system of FIG. 34 is preferred, it shall nonetheless be understood that various alternatives are possible including the use of "at least one" section 422 of metal silicide located above and on either or both sides of the resistor 86.

Further information regarding the claimed resistor system 300 and its functional capabilities will now be discussed. Use of the system 300 and its "buried" resistor design provides numerous benefits including ease of manufacture, improved reliability, the control of resistance levels independently of material layer thickness, and the like. The claimed system is also characterized by the control of "current crowding" and electromigration problems as previously defined. In particular, the specific chemical and physical characteristics of the metal silicide compositions which are used within the system 300 allow the connection thereof to the resistor 86 while avoiding the difficulties recited above. Likewise, layer thicknesses can be independently "optimized" in order to provide low interconnect resistances and improved heat-sinking capabilities which lead to reduced "TOE" values.

At this stage, some additional information concerning the geometrical/topographical characteristics of the completed system 300 shown in FIG. 34 will now be presented. With continued reference to FIG. 34, the metal silicide-containing sections 422 of the layer 420 of doped polycrystalline silicon each include a substantially planar (predominantly flat) upper face 432 as illustrated. Likewise, the intermediate section 362 of undoped polycrystalline silicon associated with the layer 420 employs a top surface 434 that is substantially planar (predominantly flat). It is a preferred and novel feature of the claimed invention that the upper face 432 of each section 422 and the top surface 434 of intermediate section 362 are substantially coplanar with each other (FIG. 34) and vice versa. The term "coplanar" as used herein shall define a relationship between the foregoing components in which the upper face 432 of each metal silicide-containing section 422 and the top surface 434 of the intermediate section 362 are all in the same plane and predominantly level with each other to form a smooth and even transition from the upper face 432 to the top surface 434 and vice versa. The word "substantially" as used in connection with the term "coplanar" is employed herein to account for slight allowable deviations from exact coplanarity which are always possible in view of permitted production tolerances, manufacturing limitations, and other factors.

The coplanar relationship described above is employed in a preferred embodiment in order to create a flat, smooth, and substantially planar horizontal surface at the top of the structure illustrated in FIG. 34, with such surface being designated hereinafter at reference number 436. This type of surface 436 is ideally suited to receive additional material layers thereon including various conductive layers, passivation structures, and the like as noted above in Section "B". As will become readily apparent from the additional data provided below, the design of the present invention is clearly distinguishable from the conventional system described in Section "B" with particular reference to the inner ends 222 of the conductive layer 214 which each have a sharply angled surface 226 immediately adjacent the resistor 86. These features of the conventional system shown in FIG. 4 and outlined in Section "B" create a non-planar region/surface immediately adjacent the resistor 86 (see brackets 228 and dashed vertical lines 224 in FIG. 4) which is difficult to completely and effectively cover with the desired passivation layers. The presence of non-planar geometry within the regions of the printhead 80 immediately adjacent the resistor 86 (e.g. right next to it at dashed vertical lines 224) typically increases the likelihood of defect formation in the overlying passivation layers including cracks, pinholes, fissures and the like. Such defects can defeat the entire purpose of the passivation layers, thereby leading to undesired ink contact with the resistor 86 and possible corrosion thereof.

However, the substantially coplanar relationship between (1) the upper face 432 of each metal silicide-containing interconnect section 422; and (2) the top surface 434 of the intermediate section 362 avoids these problems by providing a predominantly flat and even surface 436 directly above the resistor 86 and locations adjacent thereto (e.g. between brackets 438 in FIG. 34). This design is particularly characterized by the absence of sharp angles, slopes, and the like. It is also important to note that, based on the novel design of the metal silicide-containing sections 422 and their ability to function as highly-effective resistor interconnect structures, the planar horizontal surface 436 associated with the preferred structure of FIG. 34 will be present in the printhead of interest even after additional metallic overlay structures are applied as illustrated in FIG. 35 (discussed below). In other words, the system 300 shown in FIG. 34 is specifically designed to enable the placement of additional conductive layers outwardly from the resistor boundaries (see dashed lines 352 in FIG. 34) which is clearly distinguishable from the conventional system of FIG. 4. As illustrated in FIG. 4 (and in direct contrast to the claimed invention), the inner ends 222 of conductive layer 214 are positioned directly at the dashed vertical lines 224 which define the boundaries of resistor 86. Again, this distinction will be summarized in greater detail below relative to FIG. 35.

The present design as described herein again provides an improved degree of longevity and reliability in the printhead 80, 196 (or other chosen printhead design). Incidentally, the desired coplanar configuration discussed above is not substantially disrupted or otherwise defeated should the additional layers 354, 360 of silicon oxide material and silicon nitride be left in position on the planar horizontal surface 436 of the structure shown in FIG. 34 in accordance with their small size and thickness characteristics which are of minimal consequence. Likewise, by allowing the primary layers 310, 314 of silicon oxide material and silicon nitride to remain "buried" within the system 300 as illustrated in FIG. 34 (e.g. between the primary and secondary layers 370, 420), various additional benefits will be provided including improved protection of the resistor 86 thereunder.

With reference to FIG. 35, some additional steps will now be presented which are used to manufacture the printhead 80, 196 (or other comparable structure). These steps are applicable to all of the embodiments and variations described herein and basically involve the delivery of one or more additional material layers to the resistor system 300. As shown in FIG. 35, positioned on (e.g. over and above) at least part of the upper face 432 of one or both metal silicide-containing interconnect sections 422 is at least one additional layer 440 of electrically conductive material. While only one layer 440 is illustrated in FIG. 35, it shall be understood that a number of additional electrically conductive layers may be employed on top of each other without restriction. Likewise, for the purposes of this discussion, the additional layer 440 will be positioned on both of the sections 422 shown in FIG. 35 with the understanding that the layer 440 can, in fact, be applied to only one of the sections 422 as needed and desired.

The additional layer 440 of electrically conductive material is placed above the layer 420/sections 422 and is operatively attached thereto. The term "operatively attached" is defined to encompass direct attachment without any intervening materials therebetween or attachment in a manner where one or more supplemental material layers are located between the additional layer 440 and the layer 420/sections 422. Many different compositions can be employed in connection with the additional layer 440 of electrically conductive material, with the use of a single elemental metal or multiple elemental metals in combination being preferred. For example, one composition of primary interest which may be used to produce the additional layer 440 involves an alloy of copper [Cu] and aluminum [Al] which will typically (but not exclusively) contain about 0.25–0.75% by weight elemental copper and about 99.25–99.75% elemental aluminum. Other compositions suitable for producing the layer 440 include layers of the following metals and metallic compounds: titanium [Ti], gold [Au], copper [Cu], tungsten [W], cobalt [Co], molybdenum [Mo], tantalum [Ta], platinum [Pt], and mixtures thereof. Again, these materials can be employed in various layers, with multiple layers being used if needed and desired in accordance with routine preliminary testing.

Each of foregoing layers will have a preferred and non-limiting uniform individual or group thickness "$T_{21}$" within a range of about 50–10,000 Å which is subject to change as needed and desired. In addition to the embodiment listed above involving a single additional layer 440 made from a copper [Cu]/aluminum [Al] alloy, another representative example would encompass the following multiple layers in combination (not shown): (1) a bottom layer made from elemental titanium [Ti] which is applied (e.g. operatively attached/connected) to the upper face 432 of one or both of the metal silicide-containing sections 422; (2) a medial layer made from titanium nitride [TiN] positioned on the bottom layer; and (3) a top layer produced from the copper [Cu]/aluminum [Al] alloy discussed above which is located on the medial layer. The titanium nitride layer would be employed in this embodiment to further control junction spiking, electromigration problems, and the like.

Regarding deposition methods which may be used to manufacture the additional layer 440 of electrically conductive material, many different metal delivery processes are applicable including those described in Elliott, D. J., *Integrated Circuit Fabrication Technology*, McGraw-Hill Book Company, New York (1982) - (ISBN No. 0-07-019238-3), pp. 1–40, 43–85, 125–143, 165–229, and 245–286 with particular reference to conventional sputtering and/or plasma vapor deposition (PVD) techniques.

As illustrated in FIG. 35, the additional layer 440 includes outer ends 442 which are designed for operative connection to one or more drive transistors (e.g. of the "MOSFET" variety) or other control components associated with the printer unit under consideration. However, the additional layer 440 of electrically conductive material terminates within the printhead 80 at inner ends 444 (on one or both sides of the resistor 86 depending on the desired printhead configuration). The inner ends 444 are preferably located in a unique position as will now be discussed. Basically, each inner end 444 in the embodiment of FIG. 35 optimally terminates at a position "C" within the printhead 80 which is spaced outwardly (e.g. laterally) and apart from the resistor 86 in order to form a gap "G" therebetween as shown in FIG. 35. In particular, each inner end 444 of the layer 440 stops short and ahead of the boundaries associated with resistor 86 (denoted by dashed lines 352). This design is again distinguishable from the conventional resistor system illustrated in FIG. 4. With reference to FIG. 4, the conductive layer 214 includes dual portions 220 having inner ends 222 which directly contact the resistor 86 at the terminal edges thereof located at dashed vertical lines 224 (which can cause "current crowding", "hot spots", and the like as previously noted). This direct engagement between a layer of material which typically employs one or more elemental metals and the resistor 86 is avoided in a preferred embodiment of the invention using the arrangement of components discussed above and presented in FIG. 35. Such arrangement again includes (1) the outwardly-spaced orientation of the inner ends 444 of the additional layer 440 relative to the resistor 86; and (2) the "buried" location of the resistor 86. As schematically illustrated in the embodiment of FIG. 35, the gap "G" is effectively "bridged" by each section 422 of metal silicide, a portion of which spans the gap "G" and thereby forms a conductive link to the underlying resistor. As a result, electrical communication is established between the additional layer 440 of electrically conductive material and the resistor 86 without placing the resistor 86 in direct physical engagement with materials that can cause the problems listed above. The unique chemical and physical properties of the metal silicide materials associated with each section 422 again assist in avoiding the difficulties described herein. Further information of a general nature regarding this feature involving a different resistor system is nonetheless discussed in co-owned and co-pending U.S. patent application Ser. No. 09/427,512 filed on Oct. 26, 1999 entitled "High Efficiency Polycrystalline Silicon Resistor System for Use in a Thermal Inkjet Printhead" which is incorporated herein by reference (Inventor: Ramaswami, R. et al.)

While the present invention shall not be restricted to any particular size parameters in connection with the gap "G", a representative, preferred, and non-limiting embodiment will involve a gap "G" size (length) of about 5–100 $\mu$m which is subject to change in accordance with routine preliminary testing. It should likewise be noted that the specialized design described above (in which each inner end 444 of the additional layer 440 is remotely spaced from the boundaries of the resistor 86) facilitates formation and maintenance of the predominantly flat and even surface 436 at the top of the structure shown in FIG. 35 and locations adjacent thereto. This design (which is characterized by the absence of sharp angles, slopes, and the like in the vicinity of the resistor 86) controls defect formation in subsequently-applied passivation and/or other material layers. Likewise, the component arrangement of FIG. 35 reduces the need to tightly control the geometrical configuration of the inner ends 444 of layer 440 since they will be positioned away from the boundaries of resistor 86 (again denoted at dashed lines 352) and are therefore of minimal effect. In addition, beneficial thermal effects (including the prevention of excessive heat losses) are achieved in the present invention by avoiding direct contact between the "buried" resistor 86 and any elemental metal-containing layers.

As a still further point of information, it should be noted that the outward orientation of the inner ends 444 of the layer 440 relative to the resistor 86 (as characterized by gap "G") is optional in nature. In an alternative embodiment (not shown), each inner end 444 of the additional layer 440 could, in fact, be positioned directly at the vertical boundaries of the resistor 86 denoted at dashed lines 352 so that the gap "G" would effectively be eliminated. However, for the reasons given above, the arrangement of components shown in FIG. 35 is optimum and preferred (but nonetheless non-limiting).

At this point, the structure of the present invention (system 300) is completed and ready for the application of additional layers thereto that are conventionally used in printhead fabrication processes (including layers 230 and higher as shown in FIG. 4 which may be applied to the structure illustrated in FIG. 35). The claimed invention shall not be limited to the placement of any particular layers above the structure of FIG. 35 with many different variations being possible. These variations include application of the layers discussed above in Section "B" (FIG. 4) which is incorporated in this section (Section "C") by reference. Accordingly, a wide variety of different passivation layers, anti-cavitation layers, barrier layers, and the like may be delivered using the conventional techniques outlined herein without limitation.

All of the steps listed above which are used to manufacture the novel resistor system 300 involve a preferred embodiment for producing this structure. The foregoing method is preferred since it employs a single (e.g. primary) layer 370 of doped or undoped polycrystalline silicon to construct the resistor 86 on an in situ basis. Likewise, the above-listed method is also desirable in that it involves the operative attachment, connection, and/or placement of another (e.g. secondary) layer of material (preferably doped or undoped polycrystalline silicon) on the primary layer. One or more portions or sections of the secondary layer are then "converted" on an in situ basis into at least one highly conductive metal silicide-containing interconnect structure (e.g. sections 422). This interconnect structure is positioned directly adjacent a higher-resistance portion of polycrystalline silicon (namely, intermediate section 362 which is optimally undoped). Thus, by selectively treating various zones or portions of the dual layer polycrystalline silicon structure of this invention, the completed system 300 can be fabricated in an economical, efficient, and topographically-desirable manner. However, it shall be understood that the terms "forming", "fabricating", "producing", "attaching", "manufacturing", "creating", "converting" and the like relative to assembly of the claimed components in the system 300 shall be defined to involve: (A) creating the layer or component of interest in situ directly from materials which are already present or otherwise reside in the printhead as discussed above and shown in the accompanying drawing figures; (B) fabricating the layer or component under consideration using one or more conventional material deposition processes (e.g. sputtering, plasma-enhanced chemical vapor deposition [PECVD], and the like); and/or (C) pre-manufacturing the layer or component in question and thereafter securing it in position within the printhead using chemical or physical attachment means (soldering, adhesive affixation, and the like). All of these techniques can be used to form, provide, or otherwise create the various components described herein without limitation.

Furthermore, the terms "operatively connected", "operatively connecting", "operatively attached", "operatively attaching", and the like are defined above and generally involve (1) the direct attachment of one component to another component with no intervening materials therebetween; and (2) the attachment of one component to another component with one or more material layers therebetween provided that the one component being "attached" or "connected" to the other component is somehow supported by the other component (notwithstanding the presence of one or more additional material layers therebetween). This aspect of the present invention is of particular importance regarding "operative connection" of the resistor 86 to the metal silicide-containing sections 422. As shown in FIG. 34 and noted above, operative connection of the resistor 86 to metal silicide-containing sections 422 is accomplished by direct communication of these components at, for example, contact faces "A" and "B" which are on opposite sides of the resistor 86. Contact faces "A" and "B" coincide with the outer boundaries of the resistor 86 designated at dashed lines 352. The resistor 86 will have a preferred length "$L_2$" of about 5–100 μm in an exemplary and non-limiting embodiment (with this value also being applicable to the width of the resistor 86). Likewise, the relative thickness of the resistor 86 will be substantially the same as the range recited above in connection with the primary layer 302 of silicon ("TI.") as shown in FIG. 6. However, it is also contemplated that "operative connection" or "operative attachment" of the resistor 86 to the sections 422 made from metal silicide could be accomplished through the placement of one or more intermediate portions of electrically conductive material positioned on either or both sides of the resistor 86 between the resistor 86 and the sections 422 under consideration. Further information of a general nature regarding this feature involving a different resistor system is nonetheless discussed in co-owned and co-pending U.S. patent application Ser. No. 09/427,512 filed on Oct. 26, 1999 entitled "High Efficiency Polycrystalline Silicon Resistor System for Use in a Thermal Inkjet Printhead" which is incorporated herein by reference (Inventor: Ramaswami, R. et al.)

The basic methods for fabricating the novel resistor system 300 of the claimed invention are discussed in detail above with particular reference to Section "C" and the drawing figures. However, as a general and non-limiting overview designed to summarize the features of this invention from a method standpoint, the process of primary interest involves the steps of: (A) providing at least one primary layer of doped polycrystalline silicon (or undoped polycrystalline silicon although doped materials are preferred), with the primary layer including at least one section thereof which functions as an ink expulsion resistor; (B) operatively attaching at least one secondary layer of material (optimally polycrystalline silicon) in position above the primary layer; and (C) converting at least one section of the secondary layer to a metal silicide compound in order to produce a metal silicide-containing section and an unreacted polycrystalline silicon-containing section (which is ideally undoped). The metal silicide-containing section is operatively connected to and in electrical connection with the resistor, with the unreacted polycrystalline silicon-containing section being at least partially aligned over and above the resistor. A number of variations to this general process are possible within the scope of the invention as claimed.

In the procedure discussed above, if doped polycrystalline silicon is employed in the primary layer (which is preferred), this material is optimally selected from the group consisting of phosphorous-doped polycrystalline silicon (preferred), boron-doped polycrystalline silicon, arsenic-doped polycrystalline silicon, antimony-doped polycrystalline silicon, and mixtures thereof without limitation. Likewise, in a representative and non-limiting embodiment, the chosen metal silicide compound is selected from the group consisting of titanium silicide (preferred), cobalt silicide, tungsten silicide, platinum silicide, molybdenum silicide, tantalum silicide, palladium silicide, and mixtures thereof.

It should also be noted that an additional step employed in a preferred version of the claimed process will involve doping at least one section of the secondary layer of polycrystalline silicon, with the doped section thereafter being converted to the chosen metal silicide compound as previously stated. This procedure ultimately produces the interconnect sections made of metal silicide illustrated in the drawing figures. The dopant composition which may be used for this purpose is optimally selected from the group consisting of phosphorous [P] (preferred), boron [B], arsenic [As], antimony [Sb], and mixtures thereof. Finally, the claimed method preferably involves operatively attaching at least one layer of electrically conductive material over and above at least part of the metal silicide-containing sections of the secondary layer as illustrated in FIG. 35 and discussed in Section "C" above.

To further summarize the claimed method, it generally involves the steps of (1)providing at least one resistor optimally comprised of doped polycrystalline silicon which is used to expel an ink composition on-demand from the completed printhead; and (2) operatively attaching at least one layer of material in position above the resistor, with the layer of material having at least one section thereof that is produced from a metal silicide compound, with such section being operatively connected to and in electrical communication with the resistor. The above-listed layer of material further includes another section which is preferably made of undoped polycrystalline silicon. This additional section is at least partially aligned over and above the resistor. The foregoing method is novel, unique, and offers the many advantages expressed herein.

D. Ink Delivery Systems using the Novel Printhead of the Present Invention

In accordance with the information provided above, a unique printhead 80 having a high degree of thermal stability, reliability, structural integrity, and efficiency is disclosed. The benefits associated with this structure (which are provided by the specialized resistor system and arrangement of interconnect components discussed above) are summarized in the previous sections. In addition to the printheads described herein, this invention shall also encompass an "ink delivery system" which is constructed using the claimed printhead designs that employ the specialized materials and structures listed in Sections "A"–"C" above. Thus, all of the data in Sections "A"–"C" shall be incorporated by reference in the present section (Section "D").

In order to produce an ink delivery system in accordance with the present invention, an ink containment vessel is provided which is operatively connected to and in fluid communication with the claimed printhead system. The term "ink containment vessel" is defined herein and can involve any type of housing, tank, or other structure designed to hold a supply of ink (including the ink composition 32). The terms "ink containment vessel", "ink storage vessel", "housing", "chamber", and "tank" shall all be considered equivalent from a functional and structural standpoint. The ink containment vessel can involve, for example, the housing 12 employed in the self-contained cartridge 10 of FIG. 1 or the housing 172 associated with the "off-axis" system of FIGS. 2–3. Likewise, the phrase "operatively connected" shall encompass a situation in which the printhead is directly attached to an ink containment vessel as shown in FIG. 1 or remotely connected to an ink containment vessel in an "off-axis" manner as illustrated in FIG. 3. Again, an example of an "on-board" system of the type presented in FIG. 1 is provided in U.S. Pat. No. 4,771,295 to Baker et al., with "off-axis" ink delivery units being described in co-owned pending U.S. patent application Ser. No. 08/869,446 (filed on Jun. 5, 1997) entitled "AN INK CONTAINMENT SYSTEM INCLUDING A PLURAL-WALLED BAG FORMED OF INNER AND OUTER FILM LAYERS" (Olsen et al.) and co-owned U.S. Pat. No. 5,975,686 to Hauck et al., which are both incorporated herein by reference. Such documents describe and support "operative connection" of the claimed printhead (e.g. printhead 80 or 196) to a suitable ink containment vessel, with the data and benefits recited in Sections "A"–"C" again being incorporated by reference in the current section (Section "D"). This data includes the materials, components, numerical parameters, and other factors associated with the claimed resistor system 300 which employs (1) a resistor 86 as part of a primary layer 370 of polycrystalline silicon (either doped as in layer 370 or undoped); and (2) a secondary layer 420 of material located over and above the primary layer 370 so that the resistor 86 is "buried" thereunder. In a preferred embodiment, the secondary layer 420 will again have one or more sections (e.g. sections 422) comprised of a selected metal silicide compound which are in operative and electrical communication with the resistor 86 and at least another section comprised of undoped polycrystalline silicon (section 362) that is at least partially aligned over and above the resistor 86.

In addition, the ink delivery system further includes at least one layer of material having at least one opening/orifice therethrough which is secured in position above the foregoing components so that the opening is in partial or (preferably) complete axial alignment (e.g. "registry") with the resistor 86 and vice versa. Again, the opening is designed to allow ink materials to pass therethrough and out of the printhead 80. Further information regarding the types of structures which can be employed in connection with the orifice-containing layer of material (namely, the orifice plate 104 having the orifices 108 therein or other equivalent structures) is recited in Section "B".

In conclusion, the present invention involves a novel printhead system which is characterized by many benefits. These benefits are discussed in detail above and constitute a substantial advance in thermal inkjet technology. Such benefits again include without limitation: (1) improved overall reliability, stability, and longevity levels in connection with the printhead and resistor elements based on the improvements recited herein; (2) the avoidance of heating efficiency problems which can lead to resistor "hot spots", absolute limits on resistance, and the like; (3) the ability to place more resistors within a given printhead in view of the reduced operating temperatures and other factors listed herein which facilitates the reduced-cost production of large-area printheads; (4) the ability to fabricate resistor structures having resistance values that are substantially independent of material thickness in connection with the deposited material layers (which is accomplished using the "buried resistor approach" outlined above); (5) favorable "TCR"/"TOE" values; (6) the control/minimization of "current crowding" and other related problems, with this benefit leading to improved electrical efficiency; (7) reductions in printhead operating temperatures; (8) the general promotion of more favorable temperature conditions within the printhead (which result from reduced current requirements that correspondingly decrease current-based parasitic heat losses from the interconnect structures operatively attached to the resistors); (9) the ability to employ a simplified, substantially planar internal printhead design (with particular reference to the resistor element[s] and associated interconnection components) which enables more effective coverage of these items by one or more protective layers; and (10) generally superior long-term operating performance.

Having herein set forth preferred embodiments of the invention, it is anticipated that various modifications may be made thereto by individuals skilled in the relevant art which nonetheless remain within the scope of the invention. For example, the invention shall not be limited to any particular ink delivery systems, operational parameters, numerical values, dimensions, ink compositions, and component orientations within the general guidelines set forth above unless otherwise stated herein. The present invention shall therefore only be construed in accordance with the following claims:

The invention that is claimed is:

1. A high efficiency ink delivery printhead comprising:
   at least one primary layer comprised of doped polycrystalline silicon, said primary layer further comprising at least one portion thereof which functions as a resistor element that is used to expel ink on-demand from said printhead; and
   at least one secondary layer of material positioned above said primary layer, said secondary layer comprising:
      at least one section thereof comprised of a metal silicide compound which is operatively connected to and in electrical communication with said resistor element; and
      at least another section thereof comprised of undoped polycrystalline silicon.

2. The printhead of claim 1 wherein said doped polycrystalline silicon is selected from the group consisting of phosphorous-doped polycrystalline silicon, boron-doped polycrystalline silicon, arsenic-doped polycrystalline silicon, antimony-doped polycrystalline silicon, and mixtures thereof.

3. The printhead of claim 1 wherein said metal silicide compound is selected from the group consisting of titanium silicide, cobalt silicide, tungsten silicide, platinum silicide, molybdenum silicide, tantalum silicide, palladium silicide, and mixtures thereof.

4. The printhead of claim 1 further comprising a plurality of additional layers located between said primary layer and said secondary layer, said plurality of additional layers comprising a layer comprised of at least one silicon oxide compound positioned at least partially over and above said resistor element and a layer comprised of silicon nitride positioned at least partially over and above said layer comprised of said silicon oxide compound.

5. The printhead of claim 1 wherein said section of said secondary layer which is comprised of said metal silicide compound further comprises a substantially planar upper face and said section of said secondary layer which is comprised of said undoped polycrystalline silicon further comprises a substantially planar top surface, said top surface and said upper face being substantially coplanar relative to each other.

6. The printhead of claim 1 further comprising at least one layer of electrically conductive material positioned over and above at least part of said section of said secondary layer which is comprised of said metal silicide compound.

7. The printhead of claim 1 wherein said section of said secondary layer which is comprised of said undoped polycrystalline silicon is at least partially aligned over and above said resistor element.

8. A high efficiency ink delivery printhead comprising:
   at least one primary layer comprised of doped polycrystalline silicon, said doped polycrystalline silicon being selected from the group consisting of phosphorous-doped polycrystalline silicon, boron-doped polycrystalline silicon, arsenic-doped polycrystalline silicon, antimony-doped polycrystalline silicon, and mixtures thereof, said primary layer further comprising at least one portion thereof which functions as a resistor element that is used to expel ink on-demand from said printhead;
   at least one secondary layer of material positioned above said primary layer, said secondary layer comprising:

at least one section thereof comprised of a metal silicide compound which is operatively connected to and in electrical communication with said resistor element, said metal silicide compound being selected from the group consisting of titanium silicide, cobalt silicide, tungsten silicide, platinum silicide, molybdenum silicide, tantalum silicide, palladium silicide, and mixtures thereof; and at least another section thereof comprised of undoped polycrystalline silicon which is at least partially aligned over and above said resistor element, said section of said secondary layer which is comprised of said undoped polycrystalline silicon further comprising a substantially planar top surface and said section of said secondary layer which is comprised of said metal silicide compound further comprising a substantially planar upper face, said top surface and said upper face being substantially coplanar relative to each other;

a plurality of additional layers located between said primary layer and said secondary layer, said plurality of additional layers comprising a layer comprised of at least one silicon oxide compound positioned at least partially over and above said resistor element and a layer comprised of silicon nitride positioned at least partially over and above said layer comprised of said silicon oxide compound; and at least one layer of electrically conductive material positioned over and above at least part of said section of said secondary layer which is comprised of said metal silicide compound.

9. A high efficiency ink delivery printhead comprising:

a resistor element comprised of polycrystalline silicon; and at least one layer of material positioned above said resistor element, said layer of material comprising:

at least one section thereof comprised of a metal silicide compound which is operatively connected to and in electrical communication with said resistor element; and at least another section thereof comprised of polycrystalline silicon.

10. An ink delivery system for use in generating printed images comprising:

a high efficiency ink delivery printhead comprising:

at least one primary layer comprised of doped polycrystalline silicon, said primary layer further comprising at least one portion thereof which functions as a resistor element that is used to expel ink on-demand from said printhead; and at least one secondary layer of material positioned above said primary layer, said secondary layer comprising at least one section thereof comprised of a metal silicide compound which is operatively connected to and in electrical communication with said resistor element, and at least another section thereof comprised of undoped polycrystalline silicon; and an ink containment vessel operatively connected to and in fluid communication with said printhead.

11. The ink delivery system of claim 10 wherein said doped polycrystalline silicon used in said printhead is selected from the group consisting of phosphorous-doped polycrystalline silicon, boron-doped polycrystalline silicon, arsenic-doped polycrystalline silicon, antimony-doped polycrystalline silicon, and mixtures thereof.

12. The ink delivery system of claim 10 wherein said section of said secondary layer in said printhead which is comprised of said undoped polycrystalline silicon is at least partially aligned over and above said resistor element.

13. The ink delivery system of claim 10 wherein said printhead further comprises a plurality of additional layers located between said primary layer and said secondary layer, said plurality of additional layers comprising a layer comprised of at least one silicon oxide compound positioned at least partially over and above said resistor element and a layer comprised of silicon nitride positioned at least partially over and above said layer comprised of said silicon oxide compound.

14. The ink delivery system of claim 10 wherein said section of said secondary layer in said printhead which is comprised of said metal silicide compound further comprises a substantially planar upper face and said section of said secondary layer which is comprised of said undoped polycrystalline silicon further comprises a substantially planar top surface, said top surface and said upper face being substantially coplanar relative to each other.

15. The ink delivery system of claim 10 wherein said printhead further comprises at least one layer of electrically conductive material positioned over and above at least part of said section of said secondary layer which is comprised of said metal silicide compound.

16. An ink delivery system for use in generating printed images comprising:

a high efficiency ink delivery printhead comprising:

at least one primary layer comprised of doped polycrystalline silicon, said doped polycrystalline silicon being selected from the group consisting of phosphorous-doped polycrystalline silicon, boron-doped polycrystalline silicon, arsenic-doped polycrystalline silicon, antimony-doped polycrystalline silicon, and mixtures thereof, said primary layer further comprising at least one portion thereof which functions as a resistor element that is used to expel ink on-demand from said printhead;

at least one secondary layer of material positioned above said primary layer, said secondary layer comprising at least one section thereof comprised of a metal silicide compound which is operatively connected to and in electrical communication with said resistor element, said metal silicide compound being selected from the group consisting of titanium silicide, cobalt silicide, tungsten silicide, platinum silicide, molybdenum silicide, tantalum silicide, palladium silicide, and mixtures thereof, said secondary layer further comprising at least another section thereof that is comprised of undoped polycrystalline silicon which is at least partially aligned over and above said resistor element, said section of said secondary layer which is comprised of said undoped polycrystalline silicon further comprising a substantially planar top surface and said section of said secondary layer which is comprised of said metal silicide compound further comprising a substantially planar upper face, said top surface and said upper face being substantially coplanar relative to each other;

a plurality of additional layers located between said primary layer and said secondary layer, said plurality of additional layers comprising a layer comprised of at least one silicon oxide compound positioned at least partially over and above said resistor element and a layer comprised of silicon nitride positioned at least partially over and above said layer comprised of said silicon oxide compound; and at least one layer of electrically conductive material positioned over and above at least part of said section of said secondary layer which is comprised of said metal silicide compound; and an ink containment vessel operatively connected to and in fluid communication with said printhead.

17. A method for producing a high efficiency ink delivery printhead comprising:

providing at least one primary layer comprised of doped polycrystalline silicon, said primary layer further comprising at least one portion thereof which functions as a resistor element that is used to expel ink on-demand from said printhead;

operatively attaching at least one secondary layer comprised of undoped polycrystalline silicon in position above said primary layer; and converting at least one portion of said secondary layer to a metal silicide compound in order to produce a metal silicide-containing section and an undoped polycrystalline silicon-containing section, said metal silicide-containing section being operatively connected to and in electrical connection with said resistor element, with said undoped polycrystalline silicon-containing section being at least partially aligned over and above said resistor element.

18. The method of claim 17 further comprising doping said portion of said secondary layer which is converted to said metal silicide compound prior to said converting thereof.

19. The method of claim 17 further comprising operatively attaching at least one layer of electrically conductive material over and above at least part of said metal silicide-containing section of said secondary layer.

20. A method for producing a high efficiency ink delivery printhead comprising:

providing at least one resistor element comprised of polycrystalline silicon which is used to expel ink on-demand from said printhead; and operatively attaching at least one layer of material in position above said resistor element, said layer of material comprising at least one section thereof which is comprised of a metal silicide compound and is operatively connected to and in electrical communication with said resistor element, said layer of material further comprising at least another section thereof which is comprised of polycrystalline silicon.

\* \* \* \* \*